United States Patent
Satou et al.

(10) Patent No.: US 10,435,382 B2
(45) Date of Patent: *Oct. 8, 2019

(54) EPOXY COMPOUND, EPOXY RESIN, CURABLE COMPOSITION, CURED PRODUCT THEREOF, SEMICONDUCTOR SEALING MATERIAL, AND PRINTED CIRCUIT BOARD

(71) Applicant: DIC Corporation, Tokyo (JP)

(72) Inventors: Yutaka Satou, Ichihara (JP); Ayumi Takahashi, Ichihara (JP)

(73) Assignee: DIC Corporation, Tokyo (JP)

( * ) Notice: Subject to any disclaimer, the term of this patent is extended or adjusted under 35 U.S.C. 154(b) by 562 days.

This patent is subject to a terminal disclaimer.

(21) Appl. No.: 14/897,363

(22) PCT Filed: Feb. 21, 2014

(86) PCT No.: PCT/JP2014/054138
§ 371 (c)(1),
(2) Date: Dec. 10, 2015

(87) PCT Pub. No.: WO2014/199660
PCT Pub. Date: Dec. 18, 2014

(65) Prior Publication Data
US 2016/0130243 A1    May 12, 2016

(30) Foreign Application Priority Data

Jun. 14, 2013  (JP) .................. 2013-125564

(51) Int. Cl.
C07D 303/30 (2006.01)
C08G 59/32 (2006.01)
(Continued)

(52) U.S. Cl.
CPC ........ C07D 303/30 (2013.01); C07D 307/92 (2013.01); C07D 407/14 (2013.01);
(Continued)

(58) Field of Classification Search
None
See application file for complete search history.

(56) References Cited

FOREIGN PATENT DOCUMENTS

JP    2004-339371 A    12/2004
JP    2007308640 A  *  11/2007
(Continued)

OTHER PUBLICATIONS

International Search Report dated May 27, 2014, issued for PCT/JP2014/054138.

Primary Examiner — Randy P Gulakowski
Assistant Examiner — Ha S Nguyen
(74) Attorney, Agent, or Firm — Locke Lord LLP; James E. Armstrong, IV; Nicholas J. DiCeglie, Jr.

(57) ABSTRACT

There is provided an epoxy compound whose melt viscosity is low and which exhibits heat resistance and flame retardancy of a cured product; an epoxy resin which includes the same; curable composition and cured product; and semiconductor sealing material. The epoxy compound has a molecular structure represented by the following Formula (I):

$$\begin{array}{c} OG \\ | \\ X \\ | \\ OG \end{array} \quad (I)$$

(Continued)

in the formula, G represents a glycidyl group, and X represents a structural site represented by the following Structural Formula (x1) or (x2);

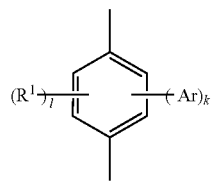

(x1)

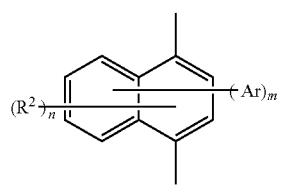

(x2)

in Formula (x1) or (x2), k represents an integer of 1 to 3, m represents 1 or 2, Ar represents a structural site represented by the following Structural Formula (Ar1) or (Ar2), and when k or m represents 2 or greater, a plurality of Ar's may be the same as or different from each other:

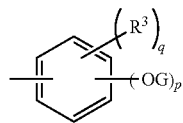

(Ar1)

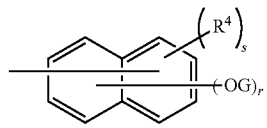

(Ar2)

in Formula (3) or (4), G represents a glycidyl group, and p and r each independently represent 1 or 2.

7 Claims, 12 Drawing Sheets

(51) Int. Cl.
| | | |
|---|---|---|
| *H05K 1/09* | (2006.01) | |
| *C07D 407/14* | (2006.01) | |
| *C07D 307/92* | (2006.01) | |
| *H05K 1/03* | (2006.01) | |
| *H01L 23/29* | (2006.01) | |

(52) U.S. Cl.
CPC ......... *C08G 59/32* (2013.01); *C08G 59/3218* (2013.01); *H01L 23/295* (2013.01); *H05K 1/0326* (2013.01); *H05K 1/0366* (2013.01); *H05K 1/09* (2013.01); *H01L 2924/0002* (2013.01); *H05K 1/0373* (2013.01); *H05K 2201/012* (2013.01)

(56) References Cited

FOREIGN PATENT DOCUMENTS

| | | | | |
|---|---|---|---|---|
| JP | 2010106150 | A | * | 5/2010 |
| JP | 2013023612 | A | * | 2/2013 |
| JP | 2013023613 | A | * | 2/2013 |

* cited by examiner

[Fig.1]
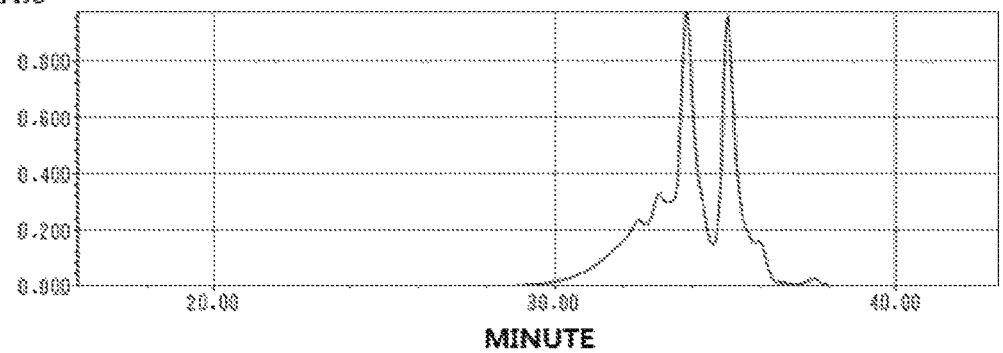
[Fig.2]
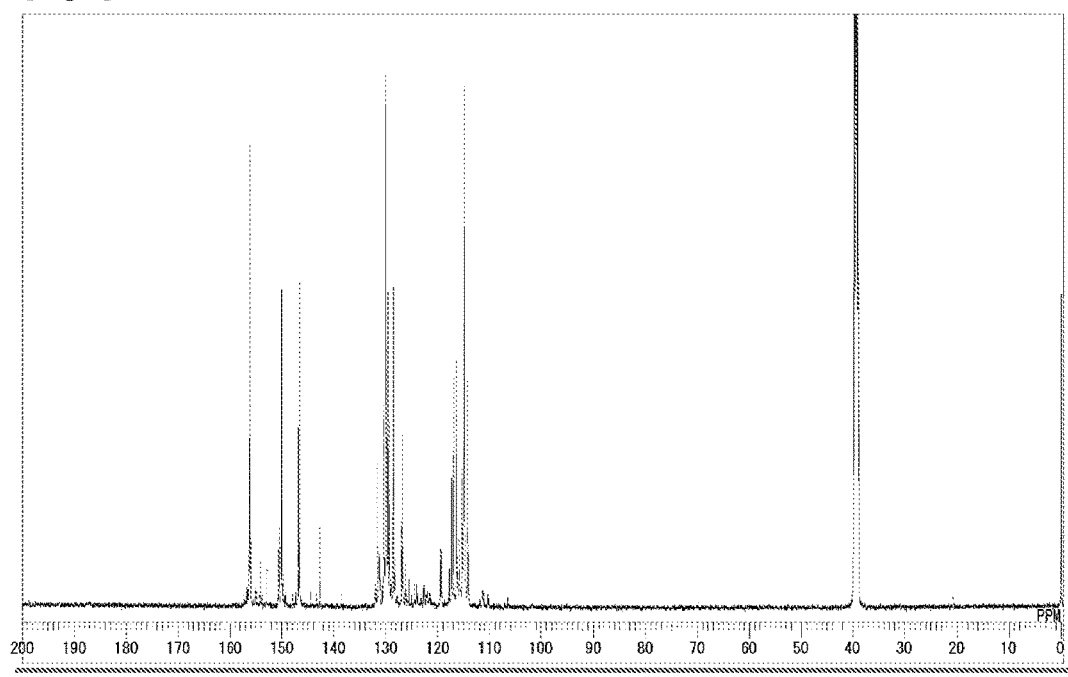

[Fig.3]
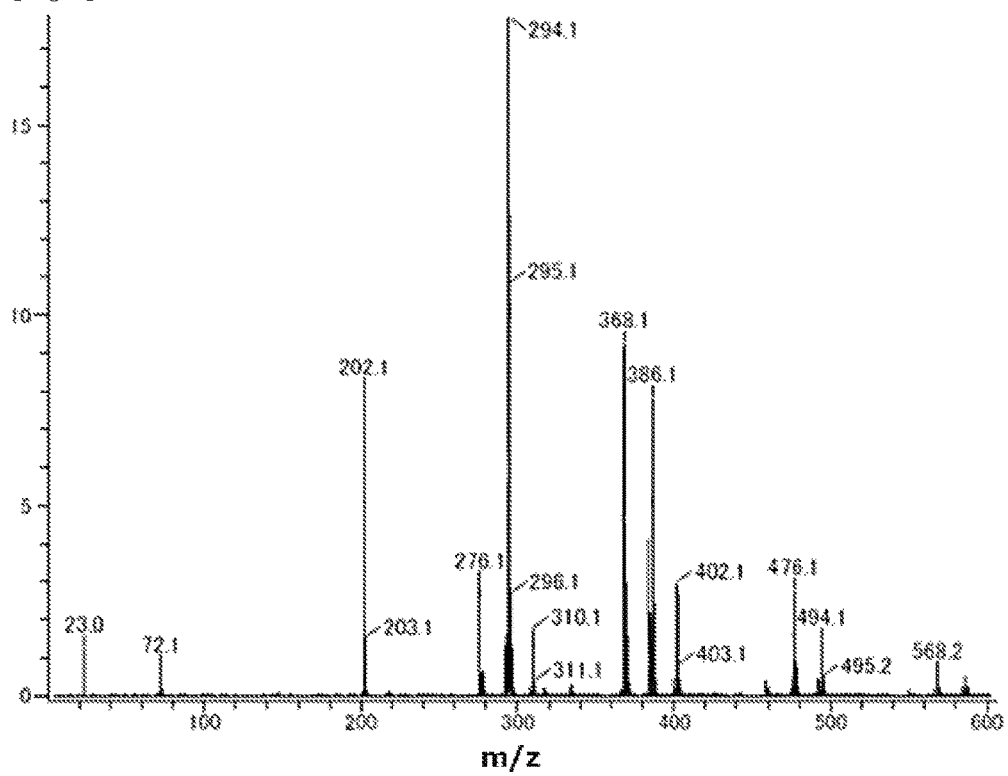
[Fig.4]
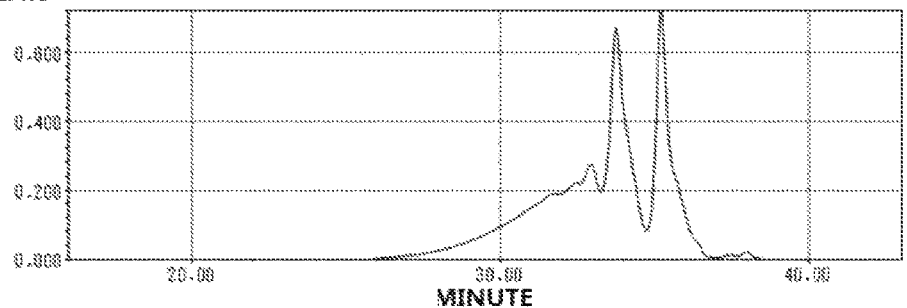
[Fig.5]
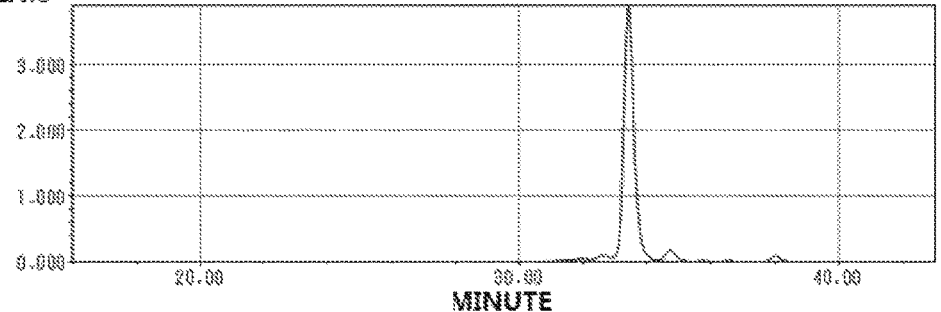

【Fig.6】
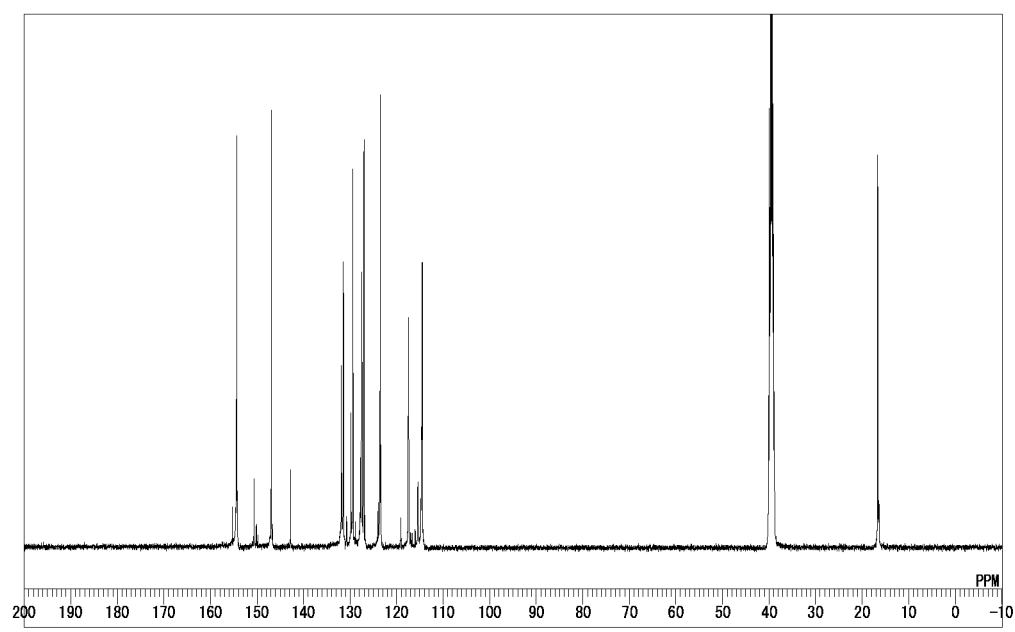

[Fig.7]
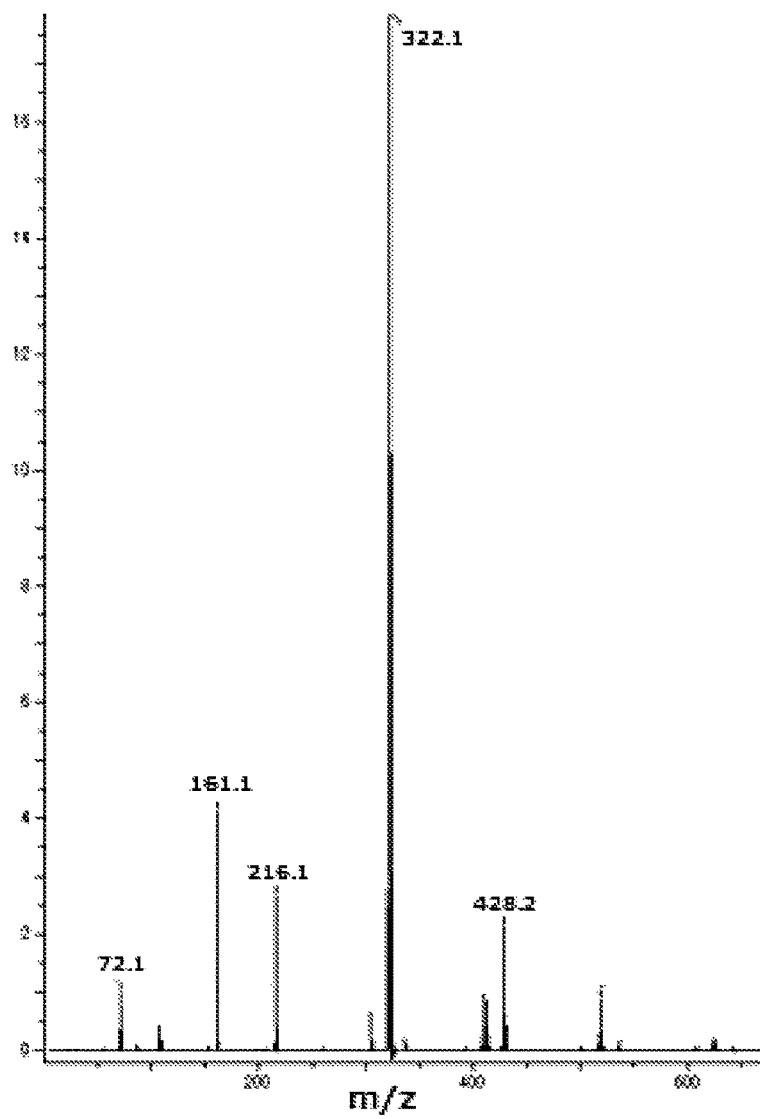
[Fig.8]
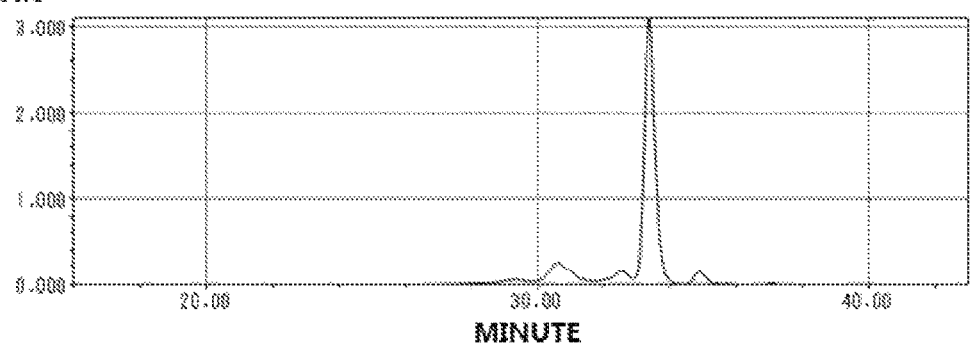

[Fig.9]
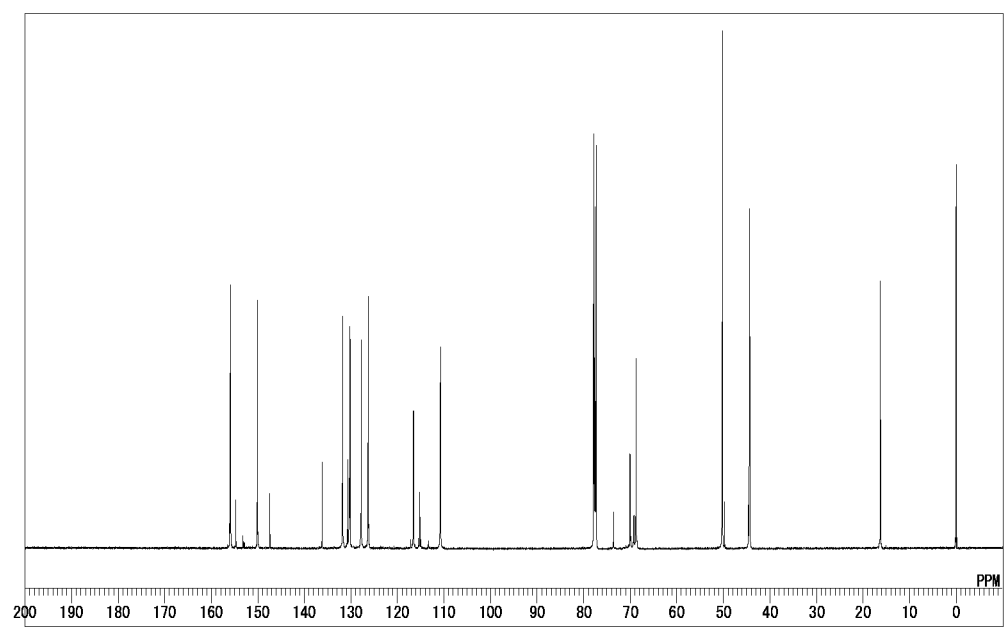

[Fig.10]
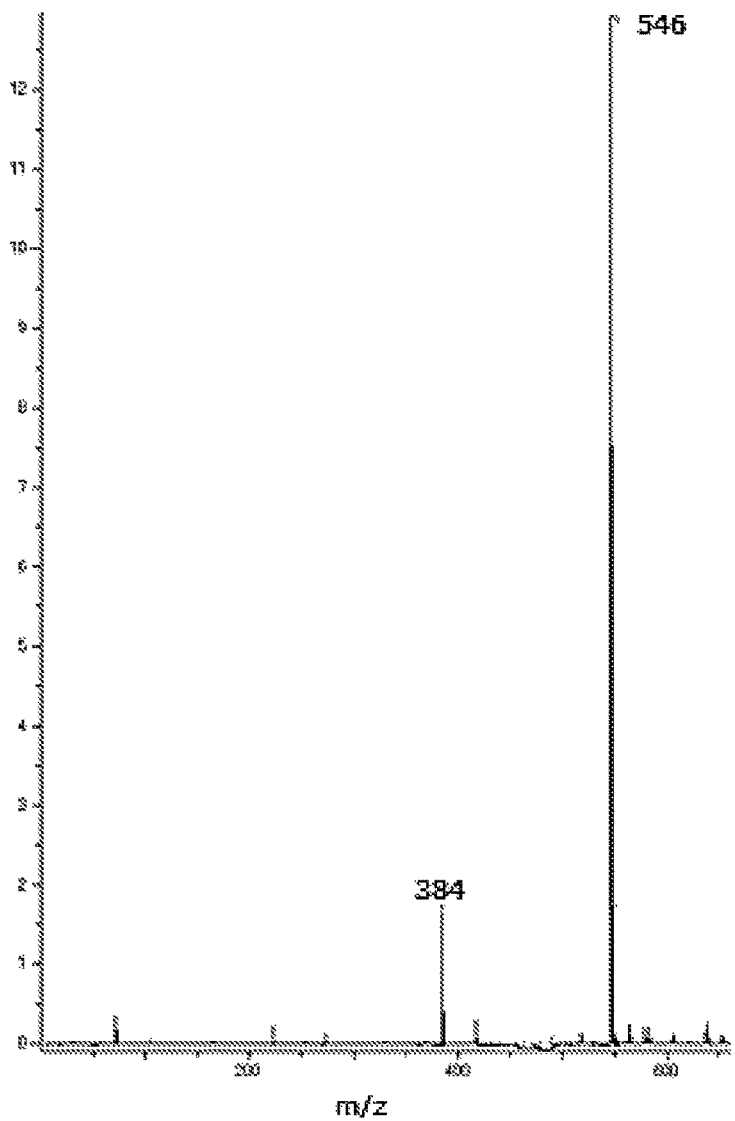
[Fig.11]
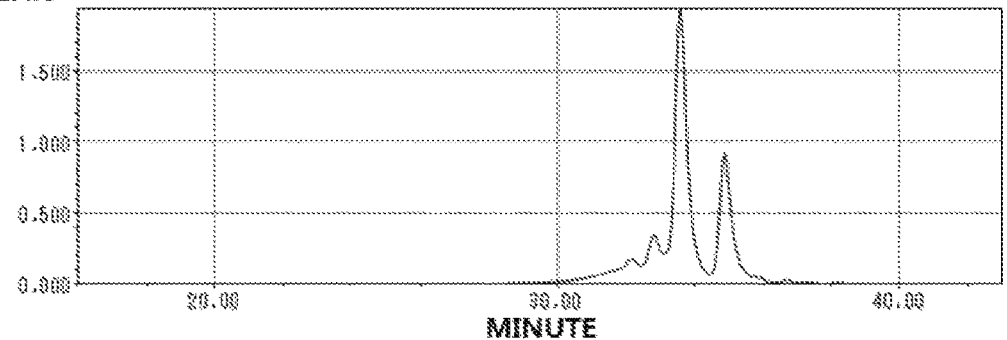

[Fig.12]
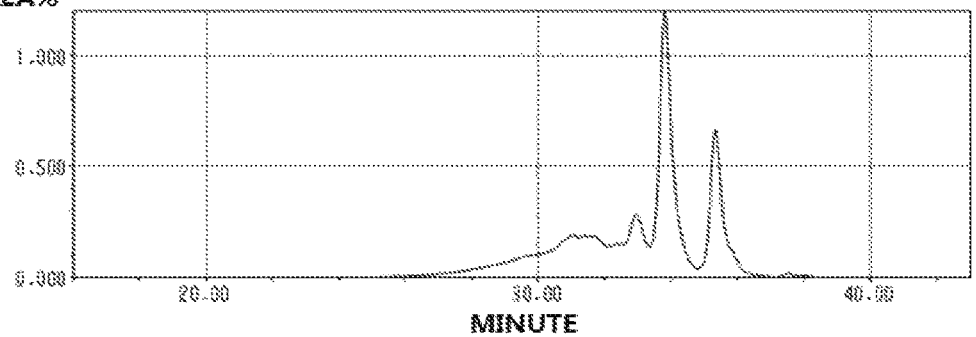
[Fig.13]
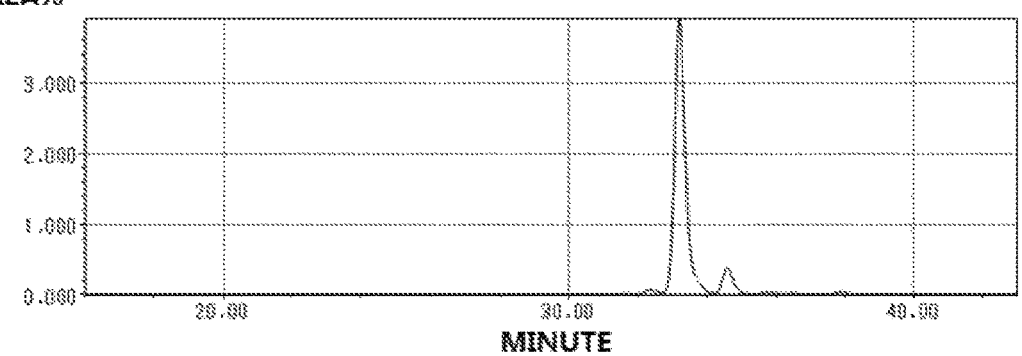
[Fig.14]
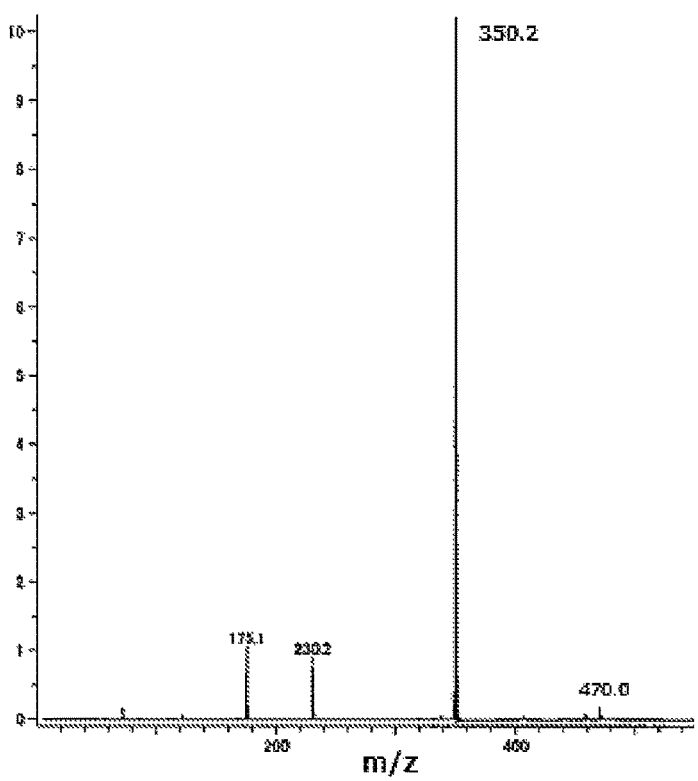

[Fig.15]
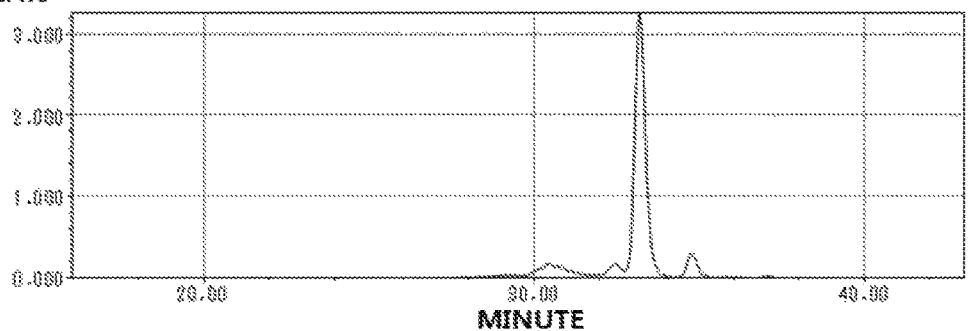
[Fig.16]
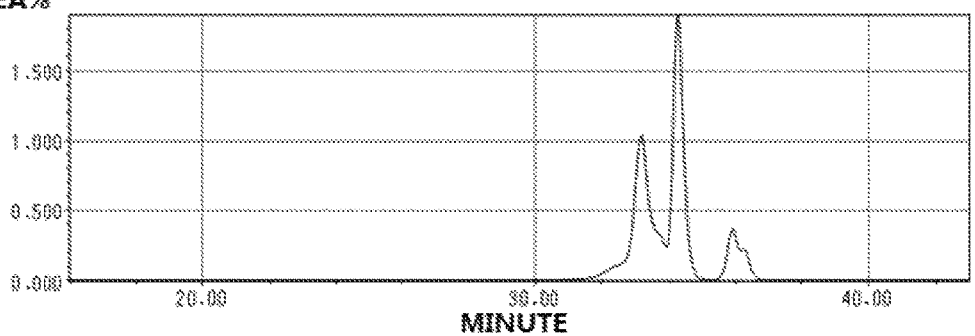
[Fig.17]
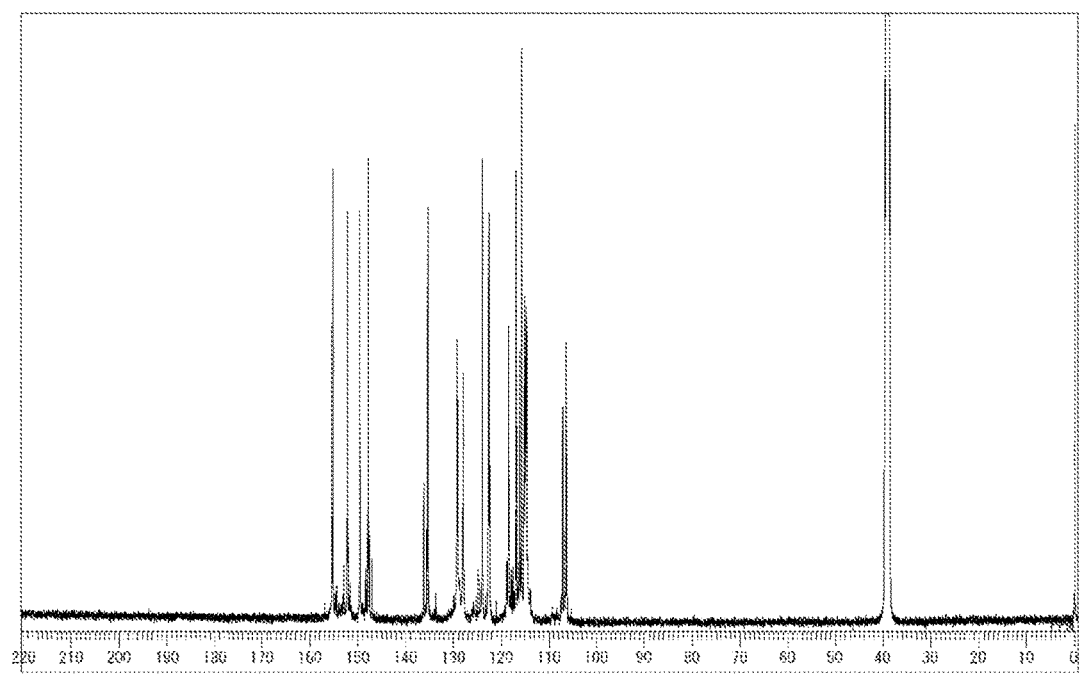

[Fig.18]
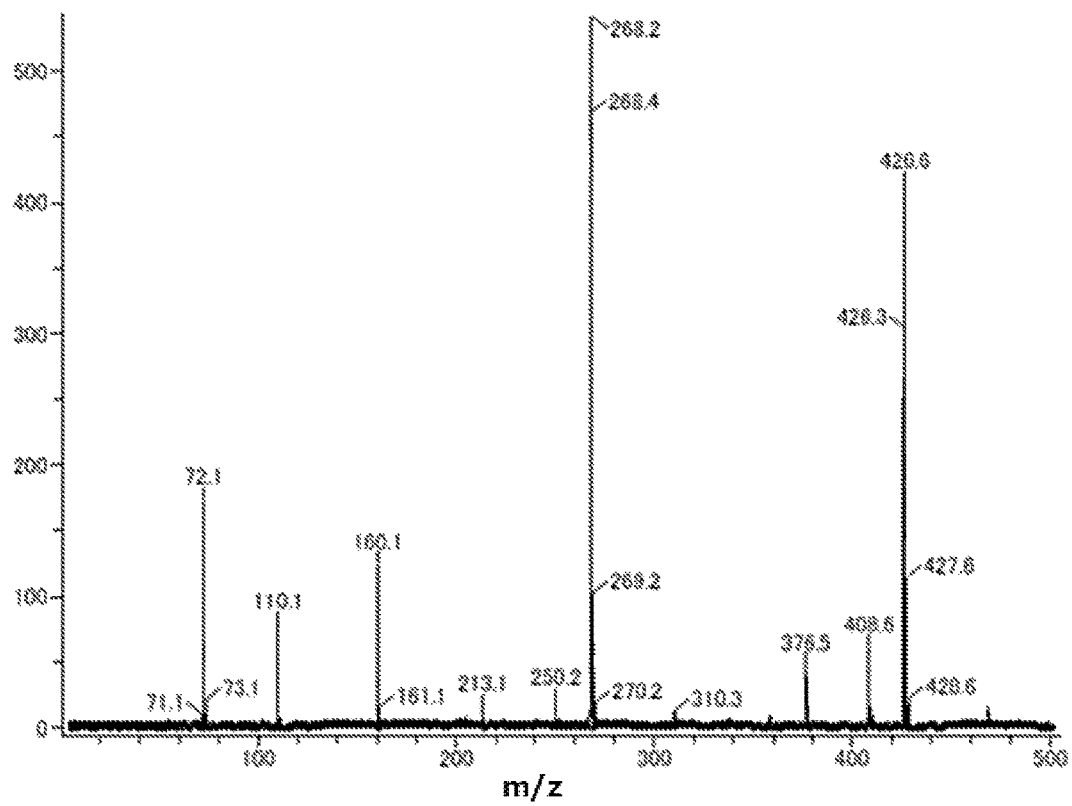
[Fig.19]
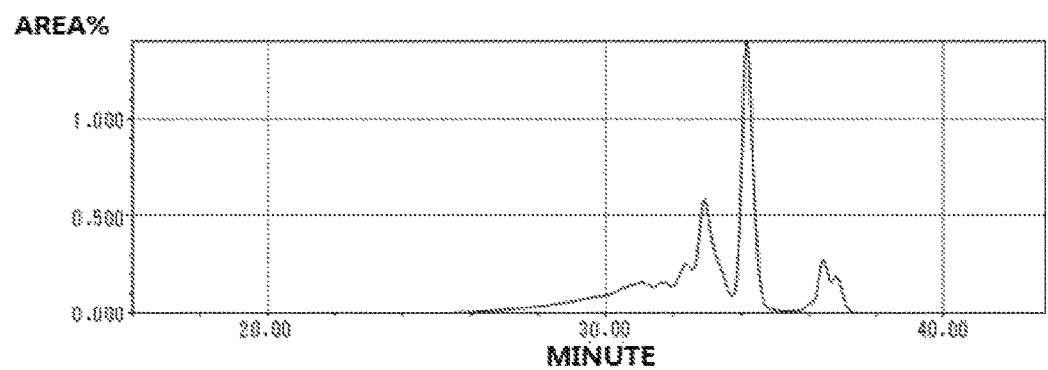

[Fig.20]
[Fig.21]
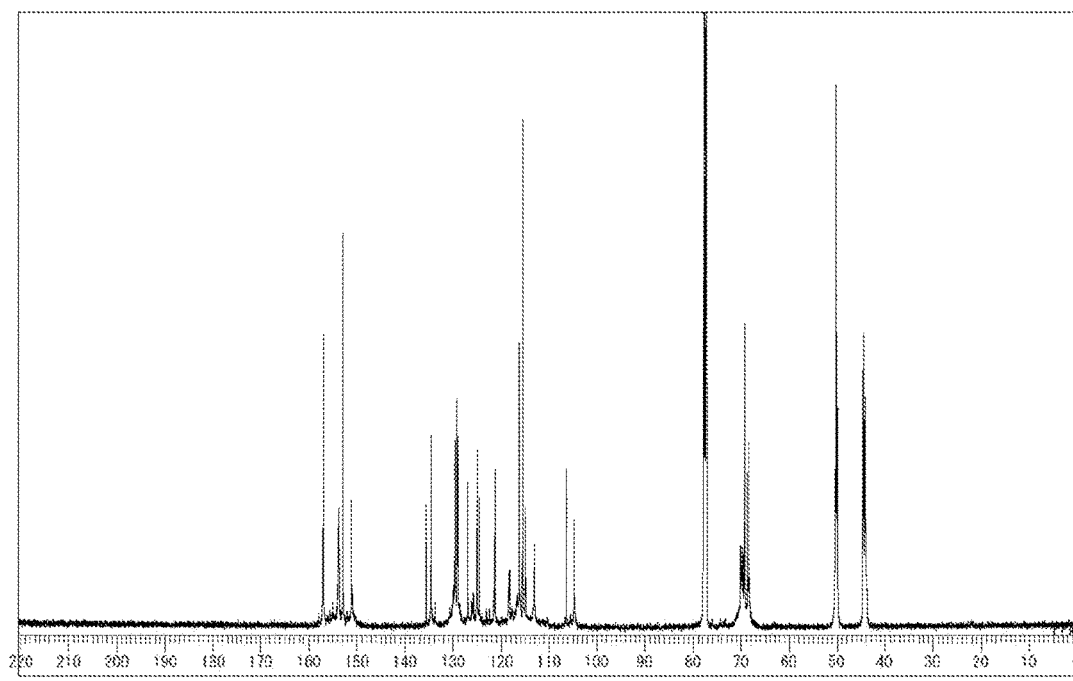

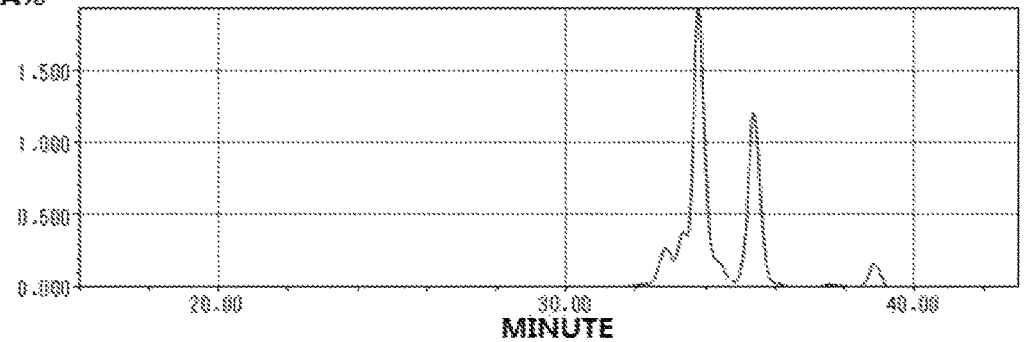
[Fig.22]
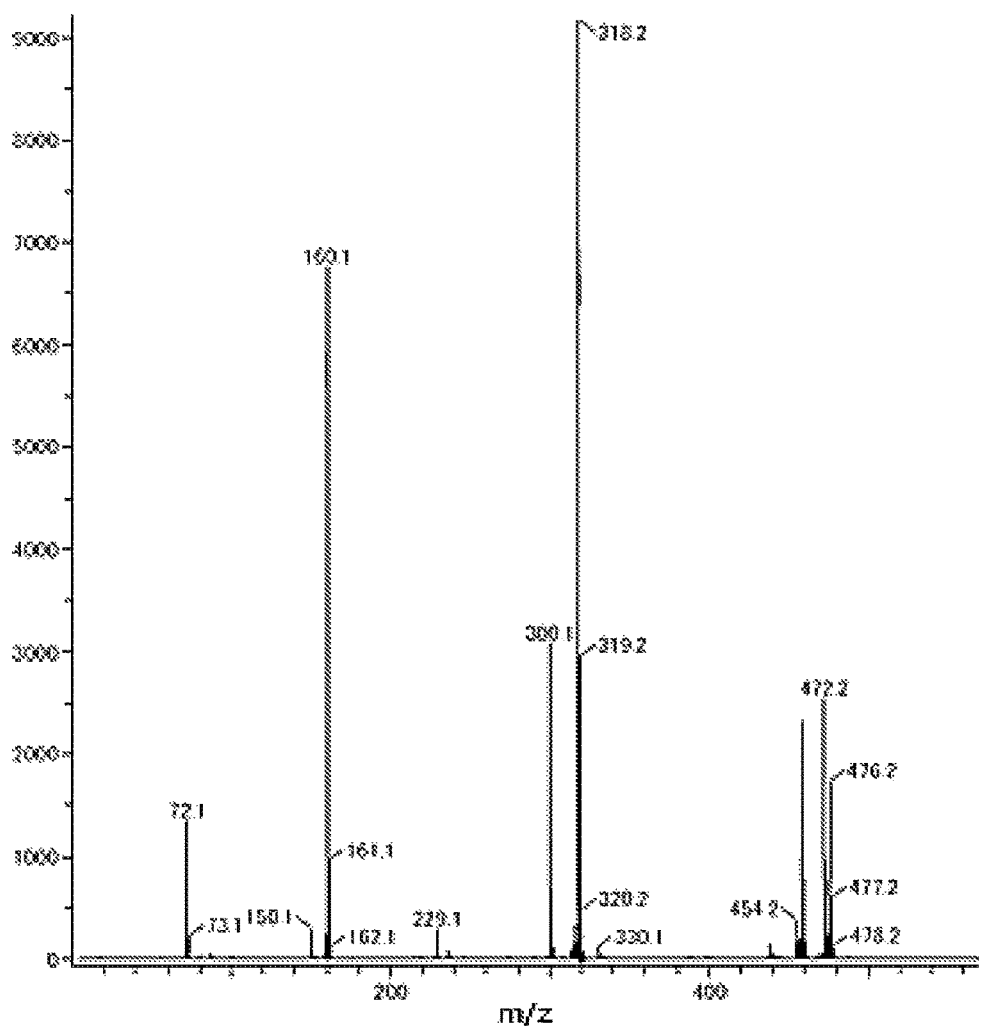
[Fig.23]

[Fig.24]
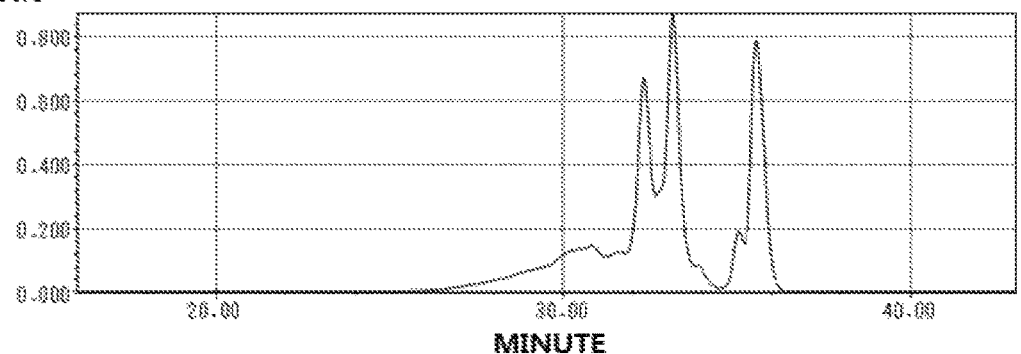
[Fig.25]
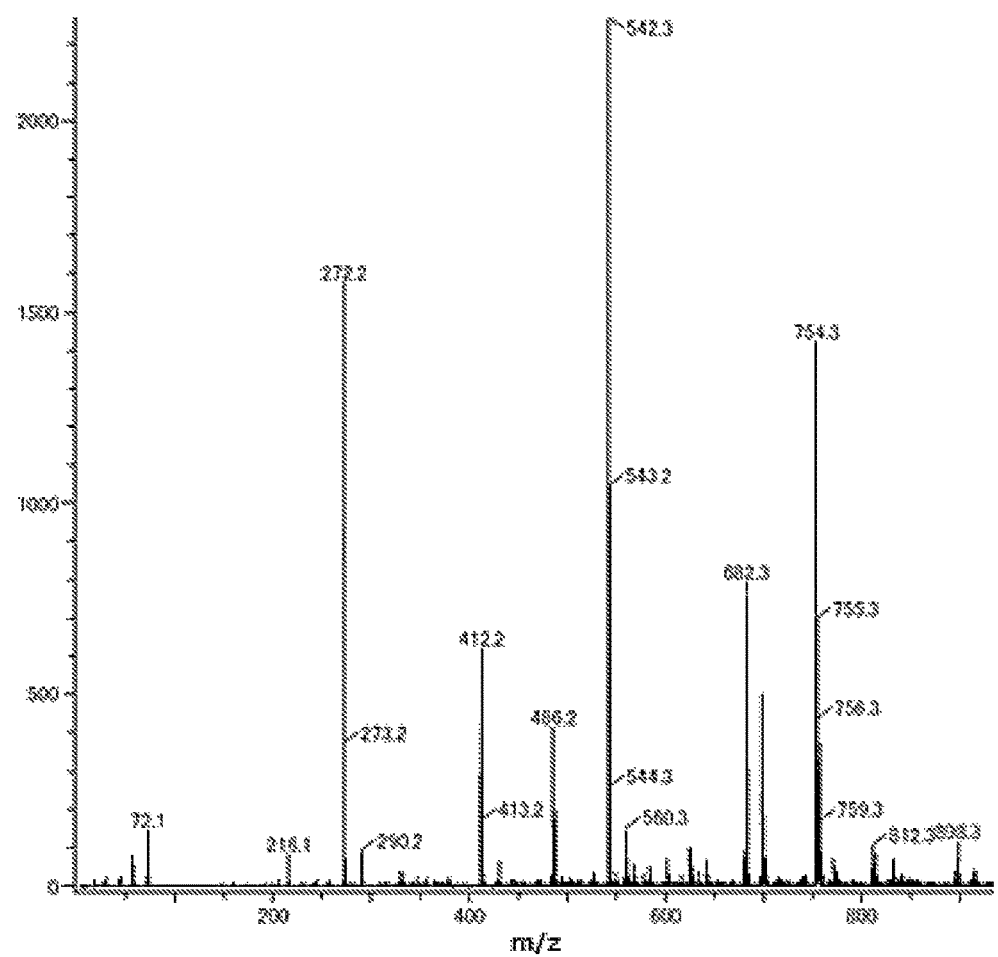

EPOXY COMPOUND, EPOXY RESIN, CURABLE COMPOSITION, CURED PRODUCT THEREOF, SEMICONDUCTOR SEALING MATERIAL, AND PRINTED CIRCUIT BOARD

TECHNICAL FIELD

The present invention relates to an epoxy compound whose melt viscosity is low and which exhibits excellent heat resistance and flame retardancy in terms of a cured product thereof; an epoxy resin which includes the same; a curable composition and a cured product thereof; a semiconductor sealing material; and a printed circuit board.

BACKGROUND ART

An epoxy resin has been used for materials such as adhesives, molding materials, and coating materials and also has been widely used in the electrical and electronic fields of semiconductor sealing materials or insulating materials for a printed circuit board in terms that an obtained cured product has excellent heat resistance or moisture resistance.

In the electrical and electronic fields, a power semiconductor typified by an automotive power module is an important technology that holds the key to energy savings in electrical and electronic devices. With further enlargement of the current, miniaturization, and an increase in efficiency of the power semiconductor, transition from a silicon (Si) semiconductor of the related art to a silicon carbide (SiC) semiconductor has proceeded. The advantage of the SiC semiconductor is that the semiconductor can be operated under a higher temperature condition, and therefore higher heat resistance is required for a semiconductor sealing material more than before. In addition, it is important for the required performance of a resin for a semiconductor sealing material to exhibit high flame retardancy even when a halogen-based flame retardant is not used and to be provided with a filler which has a low viscosity and excellent fluidity and can be highly filled, and a resin material having all these properties has been demanded.

As the resin material compatible with these various required characteristics, for example, an epoxy resin containing an epoxy compound represented by the following structural formula is known (see PTL 1).

[Chem. 1]

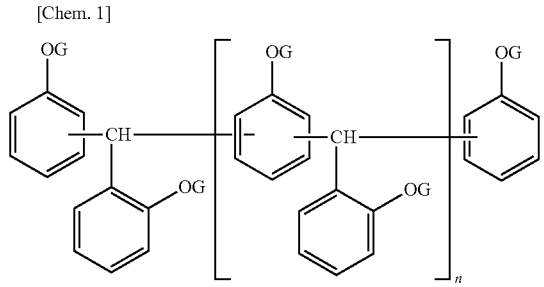

In the formula, G represents a glycidyl group.

Such an epoxy resin exhibits excellent heat resistance in terms of a cured product thereof, but flame retardancy is not sufficient and melt viscosity is high.

CITATION LIST

Patent Literature

[PTL 1] JP-A-2004-339371

SUMMARY OF INVENTION

Technical Problem

Accordingly, an object of the present invention is to provide an epoxy compound whose melt viscosity is low and which exhibits excellent heat resistance and flame retardancy in terms of a cured product thereof; an epoxy resin which includes the same; a curable composition and a cured product thereof; a semiconductor sealing material; and a printed circuit board.

Solution to Problem

As a result of intensive research for solving the above-described problem, the present inventors found that an epoxy compound obtained through polyglycidyl etherification of a reaction product which is generated by reacting a compound including a quinone skeleton with a compound including a phenolic hydroxyl group has a structure in which aromatic nuclei are bonded to each other without interposing a methylene group, and whose molecular weight is low and concentration of an epoxy group is high, and reactivity of the epoxy group is high and thus the epoxy compound has a low melt viscosity and is excellent in heat resistance and flame retardancy of a cured product thereof, thereby completing the present invention.

In other words, the present invention relates to an epoxy resin which has a molecular structure represented by the following Formula (I):

[Chem. 2]

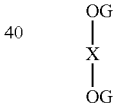  (I)

wherein, in the formula, G represents a glycidyl group, and X represents a structural site represented by the following Structural Formula (x1) or (x2);

[Chem. 3]

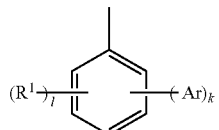 (x1)

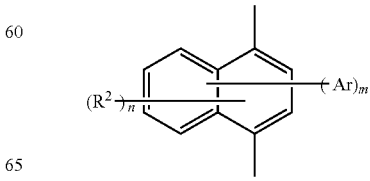 (x2)

wherein, in Formula (x1) or (x2), $R^1$ and $R^2$ each independently represent any of an alkyl group having 1 to 4 carbon atoms, an alkoxy group having 1 to 4 carbon atoms, an aryl group, or an aralkyl group, 1 represents an integer of 0 to 3, n represents an integer of 0 to 4, when 1 or n represents 2 or greater, a plurality of $R^1$'s or $R^2$'s may be the same as or different from each other, k represents an integer of 1 to 3, m represents 1 or 2, Ar represents a structural site represented by the following Structural Formula (Ar1) or (Ar2), and when k or m represents 2 or greater, a plurality of Ar's may be the same as or different from each other;

[Chem. 4]

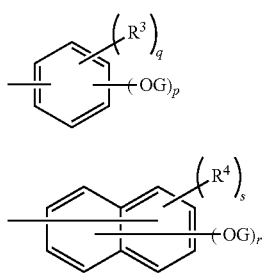

(Ar1)

(Ar2)

wherein, in Formula (Ar1) or (Ar2), G represents a glycidyl group, p and r each independently represent any of 1 or 2, $R^3$ and $R^4$ each independently represent an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s represents 2 or greater, a plurality of $R^3$'s or $R^4$'s may be the same as or different from each other.

The present invention further relates to an epoxy resin containing the epoxy compound.

The present invention further relates to a method of producing an epoxy resin including: reacting a compound (Q) which has a quinone structure in a molecular structure with a compound (P) which has a phenolic hydroxyl group in a molecular structure to obtain a phenol intermediate; and reacting the obtained phenol intermediate with epihalohydrin.

The present invention further relates to an epoxy resin which is produced by the production method.

The present invention further relates to a curable composition including, as essential components: the epoxy compound or the epoxy resin; and a curing agent.

The present invention further relates to a cured product which is obtained by performing a curing reaction on the curable composition.

The present invention further relates to a semiconductor sealing material including, besides the curable composition, an inorganic filler.

The present invention further relates to a printed circuit board which is obtained by impregnating a reinforcement basic material with a resin composition varnished by blending the curable composition with an organic solvent, superposing a copper foil on the resulting material, followed by heat-pressing.

Advantageous Effects of Invention

According to the present invention, it is possible to provide an epoxy compound whose melt viscosity is low and which exhibits excellent heat resistance and flame retardancy in terms of a cured product thereof; an epoxy resin which includes the same; a curable composition and a cured product thereof; a semiconductor sealing material; and a printed circuit board.

BRIEF DESCRIPTION OF DRAWINGS

FIG. 1 is a GPC chart of a phenol intermediate (1) obtained in Example 1.
FIG. 2 is a 13C-NMR chart of the phenol intermediate (1) obtained in Example 1.
FIG. 3 shows an MS spectrum of the phenol intermediate (1) obtained in Example 1.
FIG. 4 is a GPC chart of an epoxy resin (1) obtained in Example 1.
FIG. 5 is a GPC chart of a phenol intermediate (2) obtained in Example 2.
FIG. 6 is a 13C-NMR chart of the phenol intermediate (2) obtained in Example 2.
FIG. 7 shows an MS spectrum of the phenol intermediate (2) obtained in Example 2.
FIG. 8 is a GPC chart of an epoxy resin (2) obtained in Example 2.
FIG. 9 is a 13C-NMR chart of the epoxy resin (2) obtained in Example 2.
FIG. 10 shows an MS spectrum of the epoxy resin (2) obtained in Example 2.
FIG. 11 is a GPC chart of a phenol intermediate (3) obtained in Example 3.
FIG. 12 is a GPC chart of an epoxy resin (3) obtained in Example 3.
FIG. 13 is a GPC chart of a phenol intermediate (4) obtained in Example 4.
FIG. 14 shows an MS spectrum of the phenol intermediate (4) obtained in Example 4.
FIG. 15 is a GPC chart of an epoxy resin (4) obtained in Example 4.
FIG. 16 is a GPC chart of a phenol intermediate (5) obtained in Example 5.
FIG. 17 is a 13C-NMR chart of the phenol intermediate (5) obtained in Example 5.
FIG. 18 shows an MS spectrum of the phenol intermediate (5) obtained in Example 5.
FIG. 19 is a GPC chart of an epoxy resin (5) obtained in Example 5.
FIG. 20 is a 13C-NMR chart of the epoxy resin (5) obtained in Example 5.
FIG. 21 shows an MS spectrum of the epoxy resin (5) obtained in Example 5.
FIG. 22 is a GPC chart of a phenol intermediate (6) obtained in Example 6.
FIG. 23 shows an MS spectrum of the phenol intermediate (6) obtained in Example 6.
FIG. 24 is a GPC chart of an epoxy resin (6) obtained in Example 6.
FIG. 25 shows an MS spectrum of the epoxy resin (6) obtained in Example 6.

DESCRIPTION OF EMBODIMENTS

Hereinafter, the present invention will be described in detail.
An epoxy resin of the present invention has a molecular structure represented by the following Formula (I):

[Chem. 5]

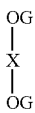

(I)

in the formula, G represents a glycidyl group, and X represents a structural site represented by the following Structural Formula (x1) or (x2);

[Chem. 6]

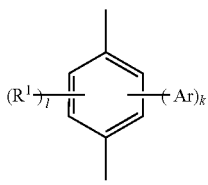

(x1)

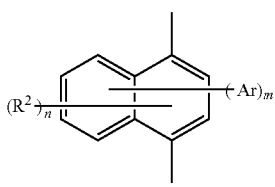

(x2)

in Formula (x1) or (x2), $R^1$ and $R^2$ each independently represent any of an alkyl group having 1 to 4 carbon atoms, an alkoxy group having 1 to 4 carbon atoms, an aryl group, or an aralkyl group, l represents an integer of 0 to 3, and n represents an integer of 0 to 4, when l or n represents 2 or greater, a plurality of $R^1$'s or $R^2$'s may be the same as or different from each other, k represents an integer of 1 to 3, m represents 1 or 2, and Ar represents a structural site represented by the following Structural Formula (Ar1) or (Ar2), and when k or m represents 2 or greater, a plurality of Ar's may be the same as or different from each other;

[Chem. 7]

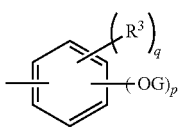

(Ar1)

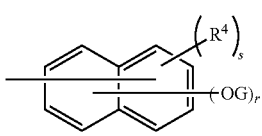

(Ar2)

in Formula (Ar1) or (Ar2), G represents a glycidyl group, p and r each independently represent 1 or 2, $R^3$ and $R^4$ each independently represent any of an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s represents 2 or greater, a plurality of $R^3$'s or $R^4$'s may be the same as or different from each other.

In the epoxy compound of the present invention represented by Formula (I), because the epoxy compound has a structure in which aromatic nuclei are bonded to each other without interposing a methylene chain, the molecular weight thereof is low and the concentration of an aromatic ring and an epoxy group is high. In general, a compound whose molecular weight is low and concentration of an epoxy group is high has a low melt viscosity, but there is a tendency that flame retardancy of a cured product thereof is poor since the concentration of a flammable epoxy group becomes higher and plural epoxy groups are present in a state of being adjacent to each other. Meanwhile, because the epoxy compound has a biphenyl skeleton or a terphenyl skeleton and two epoxy groups positioned at a para position of an aromatic nucleus in Structural Formula (x1) or (x2) have excellent reactivity, the epoxy compound of the invention of the present application is a compound whose molecular weight is low and melt viscosity is low and exhibits excellent heat resistance or flame retardancy in terms of a cured product thereof.

In Structural Formula (x1) or (x2), k represents an integer of 1 to 3 and m represents 1 or 2. A compound when k or m represents 1 (hereinafter, abbreviated as a "dinuclear compound (x1)") has a low molecular weight, has a low viscosity, and exhibits excellent heat resistance and flame retardancy in terms of a cured product thereof. Meanwhile, a compound when k or m represents 2 (hereinafter, abbreviated as a "trinuclear compound (x2)") or a compound when k represents 3 (hereinafter, abbreviated as a "tetranuclear compound (x3)") exhibits more excellent heat resistance and flame retardancy in terms of a cured product thereof since the rigidity of a molecular skeleton is higher and the concentration of an aromatic ring is high.

As a compound represented by Formula (I), a compound produced by a method of reacting a compound (Q) which has a quinone structure in a molecular structure with a compound (P) which has a phenolic hydroxyl group in a molecular structure in a temperature range of 40° C. to 180° C. in the absence of a catalyst or under the condition of an acid catalyst to obtain a phenol intermediate and reacting the obtained phenol intermediate with epihalohydrin to be glycidyl-etherificated is exemplified. In a case where the epoxy compound of the present invention is produced by such a method, an arbitrary component can be selectively produced under the reaction conditions or an epoxy resin which is a mixture of plural kinds of epoxy compounds can be produced. In addition, only an arbitrary component may be isolated from the epoxy resin which is a mixture and then be used.

As the compound (Q) having a quinone structure in a molecular structure, a compound represented by the following Structural Formula (Q1) or (Q2) is exemplified.

[Chem. 8]

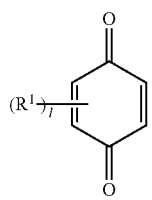

(Q1)

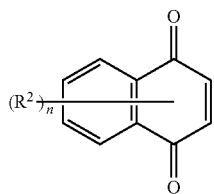

(Q2)

In Formula (Q1) or (Q2), $R^1$ and $R^2$ each independently represent any of an alkyl group having 1 to 4 carbon atoms, an alkoxy group having 1 to 4 carbon atoms, an aryl group, or an aralkyl group, 1 represents an integer of 0 to 3, and n represents an integer of 0 to 4. When 1 or n represents 2 or greater, a plurality of $R^1$'s or $R^2$'s may be the same as or different from each other.

Specific examples thereof include parabenzoquinone, 2-methylbenzoquinone, 2,3,5-trimethyl-benzoquinone, and naphthoquinone. These may be used alone or in combination of two or more kinds thereof.

As the compound (P) having a phenolic hydroxyl group in a molecular structure, a compound represented by the following Structural Formula (P1) or (P2) is exemplified.

[Chem. 9]

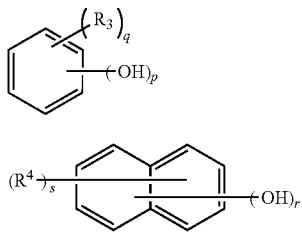

In Formula (P1) or (P2), $R^3$ and $R^4$ each independently represent any of an alkyl group having 1 to 4 carbon atoms, an alkoxy group having 1 to 4 carbon atoms, an aryl group, or an aralkyl group, q represents an integer of 0 to 4, and s represents an integer of 0 to 6. When q or s represents 2 or greater, a plurality of $R^3$'s or $R^4$'s may be the same as or different from each other. Further, p and r each independently represent 1 or 2.

Specific examples thereof include phenol, ortho-cresol, meta-cresol, para-cresol, 2,6-dimethylphenol, 2,5-dimethylphenol, 2,4-dimethylphenol, 3,5-dimethylphenol, 2,3,4-trimethylphenol, 2,3,5-trimethylphenol, 2,3,6-trimethylphenol, 2,4,5-trimethylphenol, 3,4,5-trimethylphenol, 4-isopropylphenol, 4-tert-butylphenol, 2-methoxyphenol, 3-methoxyphenol, 4-methoxyphenol, 2-methoxy-4-methylphenol, 2-tert-butyl-4-methoxyphenol, 2,6-dimethoxyphenol, 3,5-dimethoxyphenol, 2-ethoxyphenol, 3-ethoxyphenol, 4-ethoxyphenol, 2-phenylphenol, 3-phenylphenol, 4-phenylphenol, 4-benzylphenol, 1,2-dihydroxybenzene, 1,3-dihydroxybenzene, 1,4-dihydroxybenzene, 1-naphthol, 2-naphthol, 1,4-dihydroxynaphthalene, 1,5-dihydroxynaphthalene, 1,6-dihydroxynaphthalene, 2,6-dihydroxynaphthalene, and 2,7-dihydroxynaphthalene. These may be used alone or in combination of two or more kinds thereof.

The reaction of the compound (Q) having a quinone structure in a molecular structure with the compound (P) having a phenolic hydroxyl group in a molecular structure proceeds in the absence of a catalyst because of high reactivity, but the reaction may be appropriately carried out using an acid catalyst. As the acid catalyst used here, an inorganic acid such as hydrochloric acid, sulfuric acid, or phosphoric acid; an organic acid such as methanesulfonic acid, p-toluenesulfonic acid, or oxalic acid; and Lewis acid such as boron trifluoride, anhydrous aluminum chloride, or zinc chloride are exemplified. In a case of using these acid catalysts, it is preferable that the amount of the catalysts to be used is 5.0% by mass or less with respect to the total mass of the compound (Q) having a quinone structure and the compound (P) having a phenolic hydroxyl group in a molecular structure.

Moreover, it is preferable that the reaction is carried out in the absence of a solvent, but the reaction may proceed in an organic solvent as needed. As the organic solvent used here, methyl cellosolve, isopropyl alcohol, ethyl cellosolve, toluene, xylene, and methyl isobutyl ketone are exemplified. In a case of using these organic solvents, from a viewpoint of improving the reaction efficiency, it is preferable that the amount of the organic solvent to be used is in the range of 50 parts by mass to 200 parts by mass with respect to 100 parts by mass which is the total amount of the compound (Q) having a quinone structure and the compound (P) having a phenolic hydroxyl group in a molecular structure.

After the reaction of the compound (Q) having a quinone structure in a molecular structure with the compound (P) having a phenolic hydroxyl group in a molecular structure is finished, a phenol intermediate can be obtained by drying the reaction mixture under a reduced pressure.

Next, as the method of reacting a phenol intermediate with epihalohydrin, a method of carrying out a reaction by adding 0.9 mol to 2.0 mol of a basic catalyst collectively or dividedly with respect to 1 mol of a phenolic hydroxyl group in a temperature range of 20° C. to 120° C. for 0.5 hours to 10 hours using 2 mol to 10 mol of epihalohydrin per 1 mol of a phenolic hydroxyl group in the phenol intermediate is exemplified. The basic catalyst used here may be in the solid form or an aqueous solution thereof may be used. In a case of using an aqueous solution, a method of continuously adding the aqueous solution and continuously distilling water and epihalohydrins from the reaction mixture under a reduced or normal pressure condition, separating the solution to remove water, and continuously returning epihalohydrin to the reaction mixture may be used.

In addition, at the time of industrial production, the entire epihalohydrins to be used for preparation are new in the first batch of production of an epoxy resin, but it is preferable that epihalohydrin recovered from a crude reaction product and new epihalohydrin corresponding to epihalohydrin which is lost by being consumed in the reaction are used in combination after the subsequent batch. At this time, the epihalohydrin to be used is not particularly limited and examples thereof include epichlorohydrin, epibromohydrin, and β-methylepichlorohydrin. Among these, epichlorohydrin is preferable from a viewpoint of ease of industrial availability.

Moreover, specific examples of the basic catalyst include an alkaline-earth metal hydroxide, alkali metal carbonate, and an alkali metal hydroxide. Particularly, an alkali metal hydroxide is preferable in terms of excellent catalyst activity of an epoxy resin synthesis reaction, and specific examples thereof include sodium hydroxide and potassium hydroxide. The basic catalyst may be used in the form of approximately 10% by mass to 55% by mass of an aqueous solution or in the form of a solid. In addition, the reaction rate of the reaction between the phenol intermediate and the epihalohydrin can be increased by using an organic solvent together. The organic solvent to be used here is not particularly limited and examples thereof include a ketone solvent such as acetone or methyl ethyl ketone; an alcohol solvent such as methanol, ethanol, 1-propyl alcohol, isopropyl alcohol, 1-butanol, secondary butanol, or tertiary butanol; a cellosolve solvent such as methyl cellosolve or ethyl cellosolve; an ether solvent such as tetrahydrofuran, 1,4-dioxane, 1,3-dioxane, or diethoxyethane; and an aprotic polar solvent such as acetonitrile, dimethyl sulfoxide, or dimethyl formamide. These organic solvents may be used alone or in combination of two or more kinds appropriately for the purpose of adjusting polarity.

After the reaction is finished, the reaction mixture is washed with water, and unreacted epihalohydrin or an organic solvent to be used together is distilled off through distillation of the reacted mixture by being heated under a reduced pressure. Further, in order to allow the epoxy resin to have further less hydrolysable halogen, the obtained epoxy resin is dissolved again in an organic solvent such as toluene, methyl isobutyl ketone, or methyl ethyl ketone, and an aqueous solution of an alkali metal hydroxide such as sodium hydroxide or potassium hydroxide can be added thereto to be further reacted. At this time, for the purpose of improving the reaction rate, a phase transfer catalyst such as quaternary ammonium salts or crown ether may be allowed to be present. In a case of using the phase transfer catalyst, it is preferable that the amount thereof to be used is in the range of 0.1 parts by mass to 3.0 parts by mass with respect to 100 parts by mass of the epoxy resin. After the reaction is finished, generated salts are filtered and removed by being washed with water, and a solvent such as toluene or methyl isobutyl ketone is distilled off by being heated under a reduced pressure, whereby the target epoxy compound or epoxy resin of the present invention can be obtained.

The effects of the invention of the present application, in which the epoxy compound of the present invention has a low melt viscosity and heat resistance and flame retardancy of a cured product thereof are excellent, are exhibited as long as the epoxy compound has a structure represented by Formula (I). Hereinafter, more preferable examples of the epoxy compound having the structure represented by Formula (I) will be described in detail below.

As a representative example of the epoxy compound represented by Formula (I), an epoxy compound represented by any one of the following Structural Formulae (I-1) to (I-3) is exemplified.

[Chem. 10]

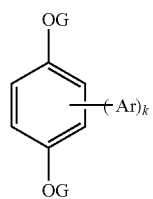
(I-1)

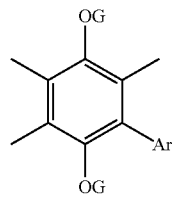
(I-2)

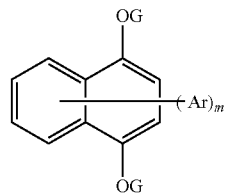
(I-3)

In Formulae (I-1) to (I-3), G represents a glycidyl group, k represents an integer of 1 to 3, m represents 1 or 2, and Ar represents a structural site represented by the following Structural Formula (Ar1) or (Ar2), and when k or m represents 2 or greater, a plurality of Ar's may be the same as or different from each other.

[Chem. 11]

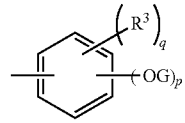
(Ar1)

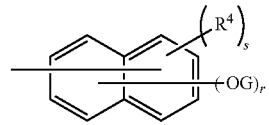
(Ar2)

In Formula (Ar1) or (Ar2), G represents a glycidyl group, p and r each independently represent 1 or 2, $R^3$ and $R^4$ each independently represent any of an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s is 2 or greater, a plurality of $R^3$'s or $R^4$'s may be the same as or different from each other.

As the epoxy compound represented by Structural Formula (I-1), more specifically, an epoxy compound represented by any one of the following Structural Formulae (1) to (7) is exemplified.

[Chem. 12]

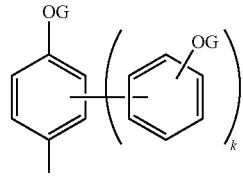
(1)

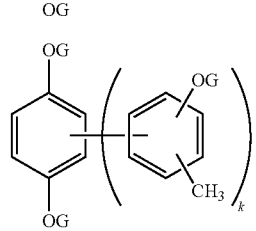
(2)

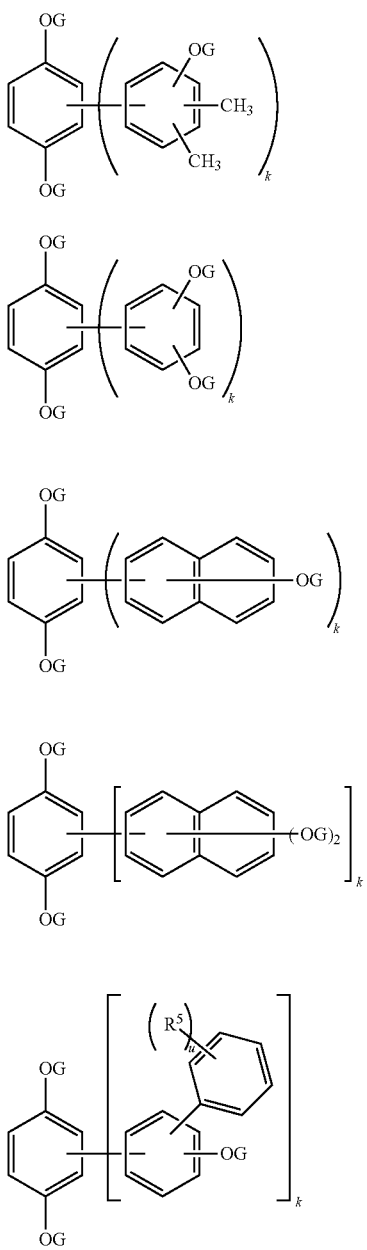

(3)
(4)
(5)
(6)
(7)

In Formulae (1) to (7), G represents a glycidyl group and k represents an integer of 1 to 3. $R^5$ represents any of an alkyl group having 1 to 4 carbon atoms, an alkoxy group having 1 to 4 carbon atoms, an aryl group, or an aralkyl group, and u represents an integer of 1 to 4. When u represents 2 or greater, a plurality of $R^5$'s may be the same as or different from each other.

Hereinafter, the respective epoxy compounds will be described in detail.

An epoxy compound represented by the following Structural Formula (1) is particularly excellent in the balance of the melt viscosity, and the heat resistance and flame retardancy of a cured product thereof among the epoxy compounds of the present invention which are represented by Formula (I).

[Chem. 13]

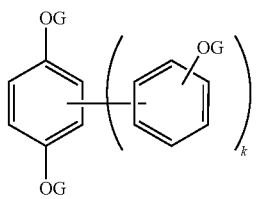

(1)

Since the epoxy compound has a low melt viscosity and is more excellent in the heat resistance and flame retardancy of a cured product thereof, it is preferable that the epoxy compound is used as an epoxy resin containing a dinuclear compound (x1) in which k in Structural Formula (1) represents 1 and a trinuclear compound (x2) in which k represents 2 and more preferable that the content ratio of the dinuclear compound (x1) in the epoxy resin is in the range of 10% to 50% in terms of the area ratio in GPC measurement and the content ratio of the trinuclear compound (x2) is in the range of 10% to 50% in terms of the area ratio in GPC measurement.

Further, in terms that a cured product which is more excellent in heat resistance and flame retardancy can be obtained, it is preferable that the epoxy compound is used as an epoxy resin containing a tetranuclear compound (x3) in which k represents 3 or a tetranuclear compound (x3') represented by the following Formula (1') in addition to the dinuclear compound (x1) and the trinuclear compound (x2). At this time, it is preferable that the total content of the tetranuclear compound (x3) and the tetranuclear compound (x3') in the epoxy resin is in the range of 2% to 20% in terms of the area ratio in the GPC measurement.

[Chem. 14]

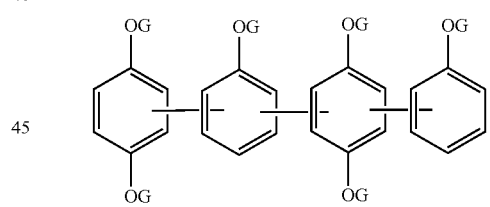

(1')

Moreover, in the present invention, the content ratio of the dinuclear compound (x1), the trinuclear compound (x2), the tetranuclear compound (x3), and the tetranuclear compound (x3') in the epoxy resin is a ratio of the peak area of the respective components to the entire peak area of the epoxy resin, which is calculated from the GPC measurement data under the following conditions.

<GPC Measurement Conditions>
Measuring device: "HLC-8220 GPC" manufactured by TOSOH CORPORATION
Column: Guard column "HXL-L" manufactured by TOSOH CORPORATION
+"TSK-GEL G2000HXL" manufactured by TOSOH CORPORATION
+"TSK-GEL G2000HXL" manufactured by TOSOH CORPORATION
+"TSK-GEL G3000HXL" manufactured by TOSOH CORPORATION +"TSK-GEL G4000HXL" manufactured by TOSOH CORPORATION
Detector: RI (Differential Refractometer)
Data treatment: "GPC-8020 model II version 4.10" manufactured by TOSOH CORPORATION
Measurement conditions: temperature of column: 40° C.
Developing solvent: tetrahydrofuran
Flow rate: 1.0 mL/min
Standard: monodisperse polystyrene whose molecular weight is known is used in conformity with measurement manual "GPC-8020 model II version 4.10" described above.

(Polystyrene to be Used)
"A-500" manufactured by TOSOH CORPORATION
"A-1000" manufactured by TOSOH CORPORATION
"A-2500" manufactured by TOSOH CORPORATION
"A-5000" manufactured by TOSOH CORPORATION
"F-1" manufactured by TOSOH CORPORATION
"F-2" manufactured by TOSOH CORPORATION
"F-4" manufactured by TOSOH CORPORATION
"F-10" manufactured by TOSOH CORPORATION
"F-20" manufactured by TOSOH CORPORATION
"F-40" manufactured by TOSOH CORPORATION
"F-80" manufactured by TOSOH CORPORATION
"F-128" manufactured by TOSOH CORPORATION Sample: 1.0% by mass of a tetrahydrofuran solution being filtered (50 μl) using a microfilter in terms of the solid content of a resin The epoxy compound represented by Structural Formula (1) can be produced by the above-described method, for example, using parabenzoquinone as the compound (Q) having a quinone structure in the molecular structure and using phenol as the compound (P) having a phenolic hydroxyl group in the molecular structure. Because the content of the dinuclear compound (x1) and the trinuclear compound (x2) in the obtained epoxy resin is easily adjusted to be in the above-described preferred range, it is preferable that the reaction ratio of phenol to parabenzoquinone at this time is set so that the content of phenol to 1 mol of parabenzoquinone is in the range of 0.1 mol to 10.0 mol.

As the compound represented by Structural Formula (1), an epoxy compound represented by any one of the following Structural Formulae (1-1) to (1-9) is exemplified.

[Chem. 15]

(1-1)
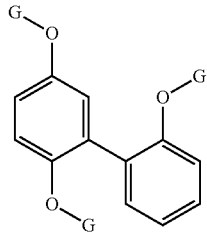

(1-2)
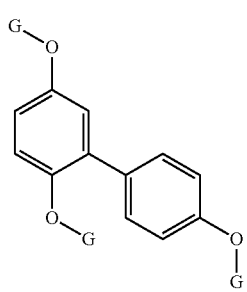

(1-3)
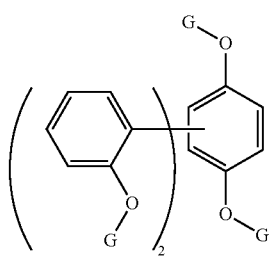

(1-4)
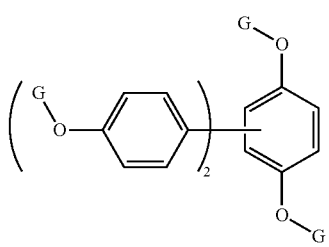

(1-5)
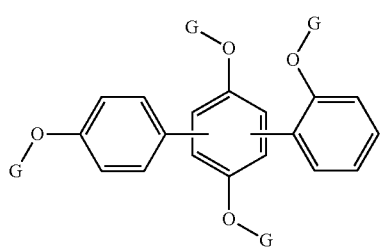

(1-6)
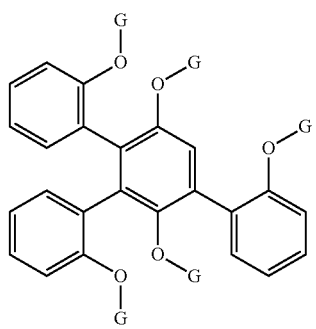

(1-7)
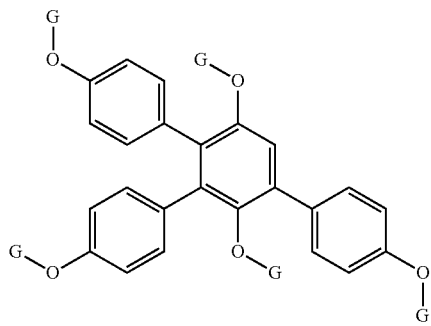

-continued (1-8)

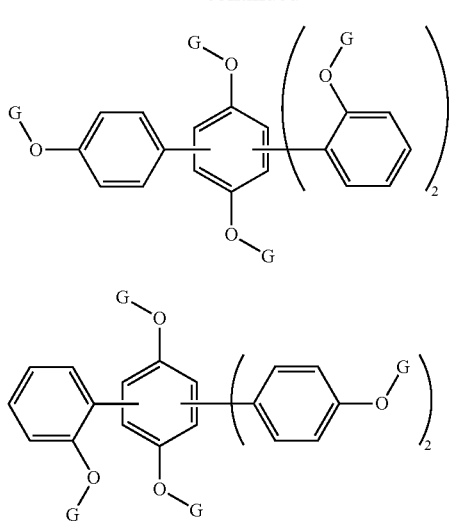

(1-9)

The epoxy compound represented by the following Structural Formula (2) has a particularly low melt viscosity and is excellent in the heat resistance and flame retardancy of a cured product thereof among the epoxy compounds of the present invention which are represented by Formula (I).

[Chem. 16]

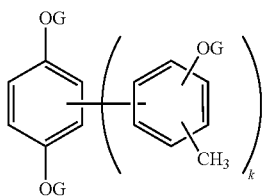

(2)

Since the epoxy compound has a low melt viscosity and is more excellent in the heat resistance and flame retardancy of a cured product thereof, it is preferable that the epoxy compound is used as an epoxy resin containing a dinuclear compound (x1) in which k in Structural Formula (2) represents 1 and a trinuclear compound (x2) in which k in Structural Formula (2) represents 2 and more preferable that the content ratio of the dinuclear compound (x1) in the epoxy resin is in the range of 2% to 50% in terms of the area ratio in the GPC measurement and the content ratio of the trinuclear compound (x2) is in the range of 10% to 90% in terms of the area ratio in the GPC measurement. Further, it is particularly preferable that the content ratio of the dinuclear compound (x1) in the epoxy resin is in the range of 2% to 25% in terms of the area ratio in the GPC measurement and the content ratio of the trinuclear compound (x2) is in the range of 25% to 90% in terms of the area ratio in the GPC measurement.

Further, in terms that a cured product which is more excellent in heat resistance can be obtained, it is preferable that the epoxy compound is used as an epoxy resin containing a tetranuclear compound (x3) in which k in Structural Formula (2) represents 3 or a tetranuclear compound (x3') represented by the following Structural Formula (2') in addition to the dinuclear compound (x1) and the trinuclear compound (x2). At this time, it is preferable that the total content of the tetranuclear compound (x3) and the tetranuclear compound (x3') in the epoxy resin is in the range of 2% to 20% in terms of the area ratio in the GPC measurement.

[Chem. 17]

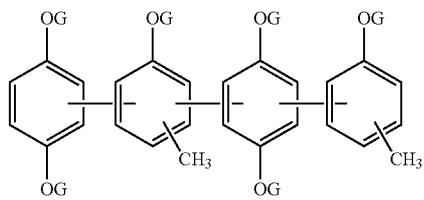

(2')

The epoxy compound represented by Structural Formula (2) can be produced by the above-described method, for example, using parabenzoquinone as the compound (Q) having a quinone structure in the molecular structure and using cresol as the compound (P) having a phenolic hydroxyl group in the molecular structure. Because the content of the dinuclear compound (x1) and the trinuclear compound (x2) in the obtained epoxy resin is easily adjusted to be in the above-described preferred range, it is preferable that the reaction ratio of cresol to parabenzoquinone at this time is set so that the content of cresol to 1 mol of parabenzoquinone is in the range of 0.1 mol to 10.0 mol.

The cresol used here may be any one of ortho-cresol, meta-cresol, and para-cresol and may be used in combination of plural kinds thereof. Among these, since an epoxy resin whose melt viscosity is low and which is excellent in heat resistance and flame retardancy of a cured product thereof can be obtained, ortho-cresol is preferable.

As the compound represented by Structural Formula (2), an epoxy compound represented by any one of the following Structural Formulae (2-1) to (2-31) is exemplified.

[Chem. 18]

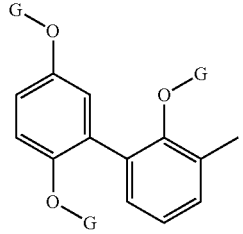

(2-1)

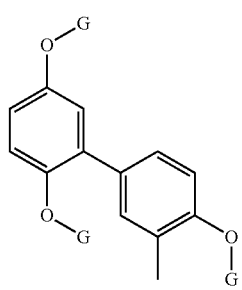

(2-2)

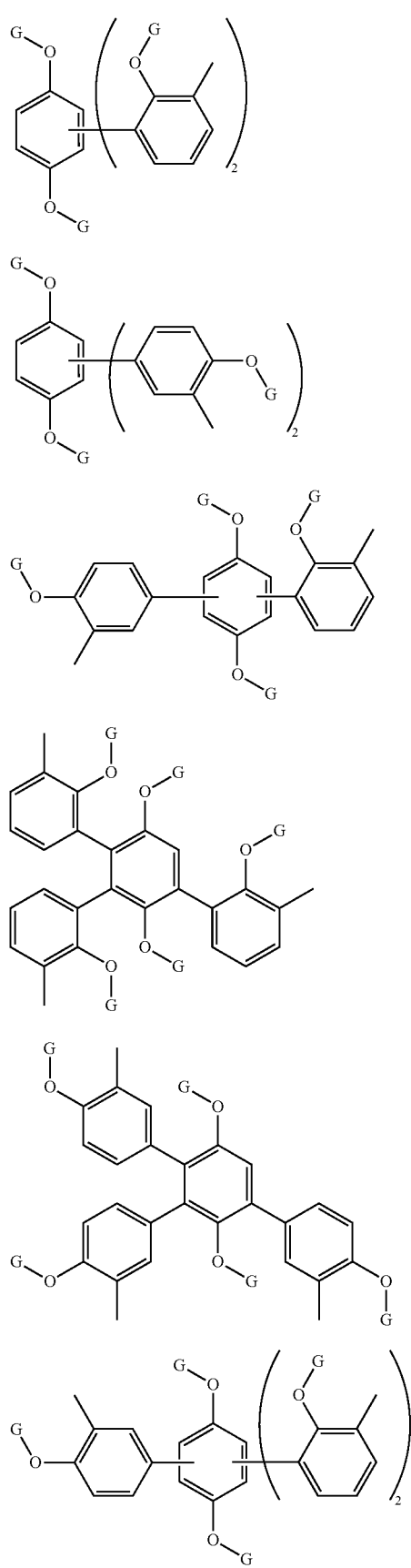

(2-15)
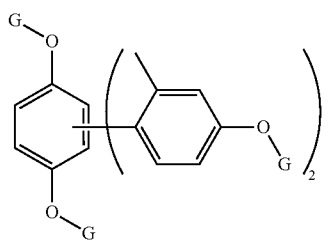
(2-16)
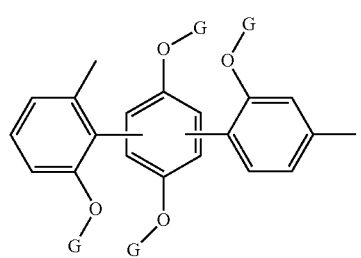
(2-17)
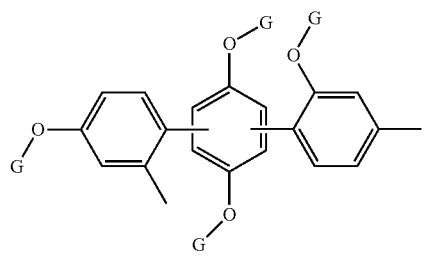
(2-18)
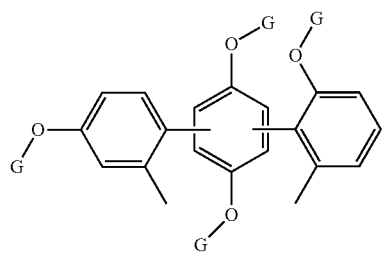
(2-19)
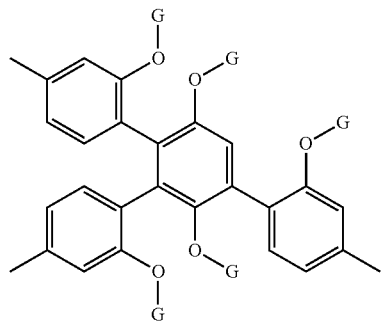
(2-20)
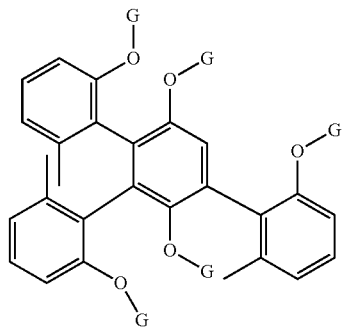
(2-21)
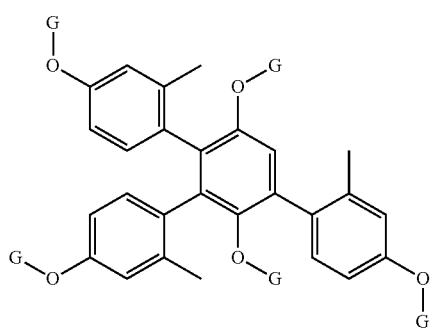
(2-22)
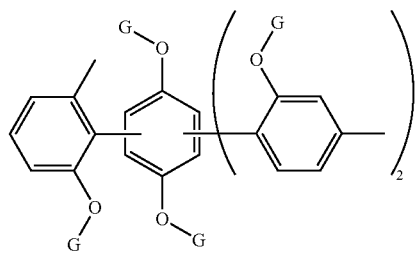
(2-23)
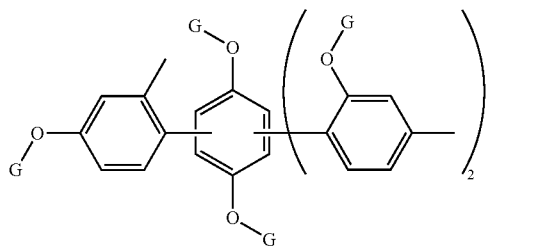
(2-24)
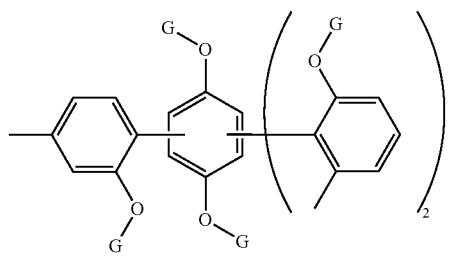

-continued (2-25)
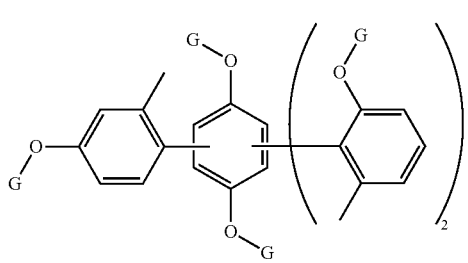

(2-26)
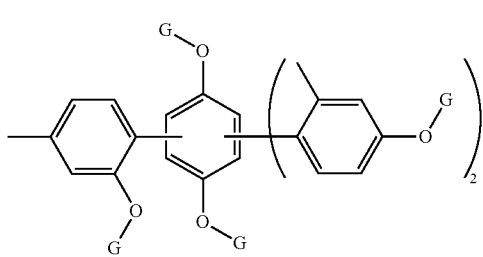

(2-27)
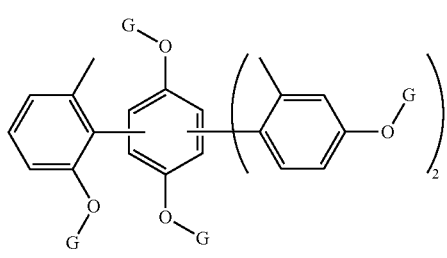

(2-28)
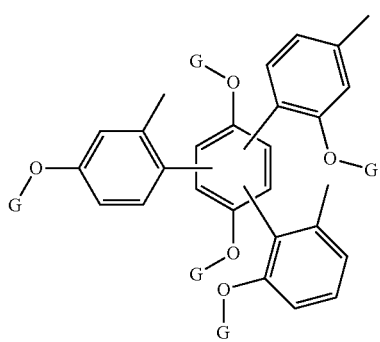

[Chem. 20]

(2-29)
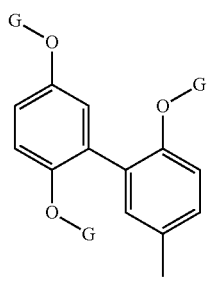

-continued (2-30)
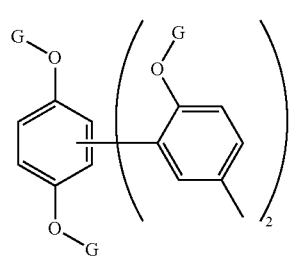

(2-31)
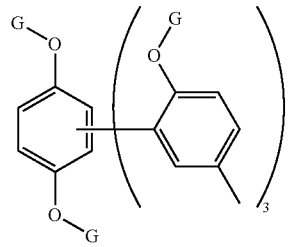

The epoxy compound represented by the following Structural Formula (3) has a particularly low melt viscosity and is excellent in the heat resistance and flame retardancy of a cured product thereof among the epoxy compounds of the present invention which are represented by Formula (I).

[Chem. 21]

(3)
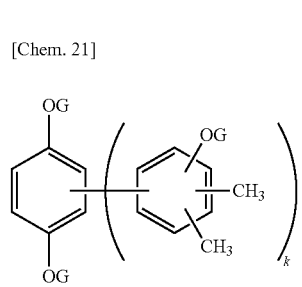

Since the epoxy compound has a low melt viscosity and is more excellent in the heat resistance and flame retardancy of a cured product thereof, it is preferable that the epoxy compound is used as an epoxy resin containing a dinuclear compound (x1) in which k in Structural Formula (3) represents 1 and a trinuclear compound (x2) in which k in Structural Formula (3) represents 2 and more preferable that the content ratio of the dinuclear compound (x1) in the epoxy resin is in the range of 2% to 50% in terms of the area ratio in the GPC measurement and the content ratio of the trinuclear compound (x2) is in the range of 10% to 95% in terms of the area ratio in the GPC measurement. Further, it is particularly preferable that the content ratio of the dinuclear compound (x1) in the epoxy resin is in the range of 2% to 25% in terms of the area ratio in the GPC measurement and the content ratio of the trinuclear compound (x2) is in the range of 50% to 95% in terms of the area ratio in the GPC measurement.

Further, in terms that a cured product which is more excellent in heat resistance can be obtained, it is preferable that the epoxy compound is used as an epoxy resin containing a tetranuclear compound (x3) in which k in Structural Formula (3) represents 3 or a tetranuclear compound (x3') represented by the following Structural Formula (3') in addition to the dinuclear compound (x1) and the trinuclear compound (x2). At this time, it is preferable that the total content of the tetranuclear compound (x3) and the tetranuclear compound (x3') in the epoxy resin is in the range of 0.5% to 10% in terms of the area ratio in the GPC measurement.

[Chem. 22]

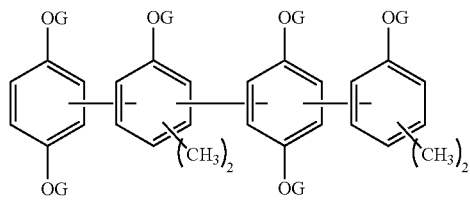

(3')

The epoxy compound represented by Structural Formula (3) can be produced by the above-described method, for example, using parabenzoquinone as the compound (Q) having a quinone structure in the molecular structure and using dimethylphenol as the compound (P) having a phenolic hydroxyl group in the molecular structure. Because the content of the dinuclear compound (x1) and the trinuclear compound (x2) in the obtained epoxy resin is easily adjusted to be in the above-described preferred range, it is preferable that the reaction ratio of dimethylphenol to parabenzoquinone at this time is set so that the content of dimethylphenol to 1 mol of parabenzoquinone is in the range of 0.1 mol to 10.0 mol.

The dimethylphenol used here may be any position isomer, for example, 2,6-dimethylphenol, 2,5-dimethylphenol, 2,4-dimethylphenol, or 3,5-dimethylphenol. Among these, since an epoxy resin whose melt viscosity is low and which is excellent in heat resistance and flame retardancy of a cured product thereof can be obtained, 2,6-dimethylphenol is preferable.

As the compound represented by Structural Formula (3), an epoxy compound represented by any one of the following Structural Formulae (3-1) to (3-3) is exemplified.

[Chem. 23]

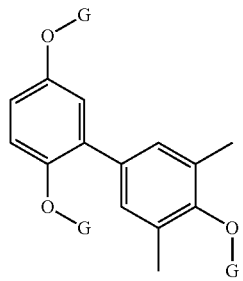

(3-1)

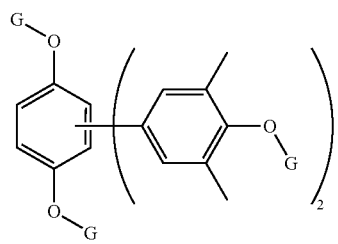

(3-2)

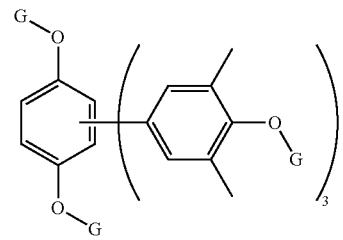

(3-3)

An epoxy compound represented by the following Structural Formula (4) can be produced by the above-described method, for example, using parabenzoquinone as the compound (Q) having a quinone structure in the molecular structure and using dihydroxybenzene as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of dihydroxybenzene to parabenzoquinone at this time is set so that the content of dihydroxybenzene to 1 mol of parabenzoquinone is in the range of 0.1 mol to 10.0 mol.

[Chem. 24]

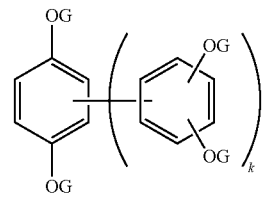

(4)

The dihydroxybenzene used here may be any position isomer, for example, 1,2-dihydroxybenzene, 1,3-dihydroxybenzene, or 1,4-dihydroxybenzene. Among these, since an epoxy resin whose melt viscosity is low and which is excellent in heat resistance and flame retardancy of a cured product thereof can be obtained, 1,3-dihydroxybenzene is preferable.

As the compound represented by Structural Formula (4), an epoxy compound represented by any one of the following Structural Formulae (4-1) to (4-3) is exemplified.

[Chem. 25]

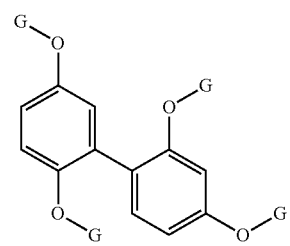

(4-1)

(4-2)
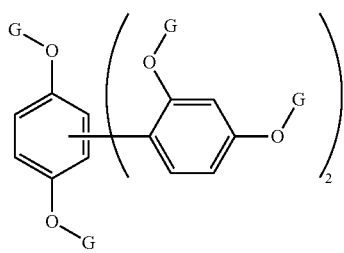

(4-3)
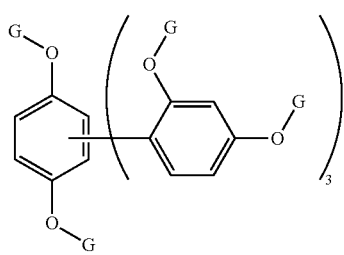

An epoxy resin containing the epoxy compound represented by Structural Formula (4) may further contain an epoxy compound other than these. As another epoxy compound, an epoxy compound represented by any one of the following Structural Formulae (1-10) to (1-12) or (4'-1) to (4'-5) is exemplified.

[Chem. 26]

(1-10)
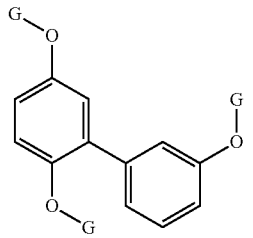

(1-11)
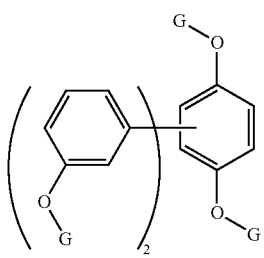

(1-12)
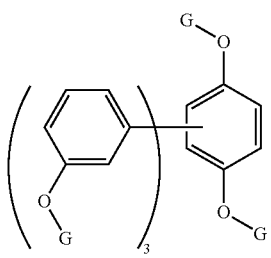

(4'-1)
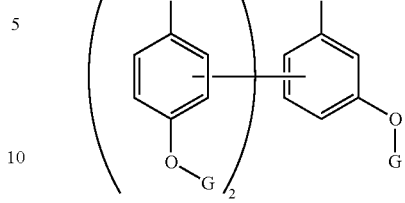

(4'-2)
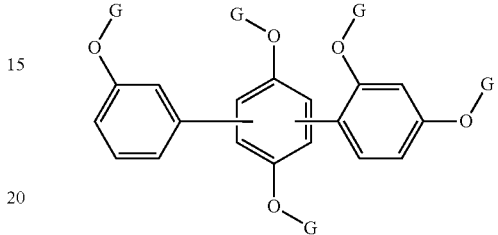

(4'-3)
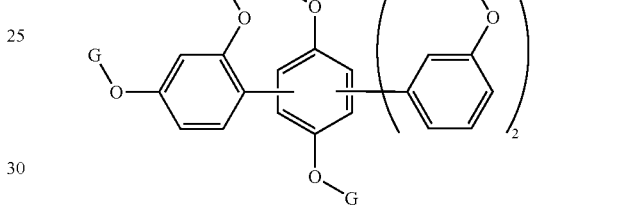

(4'-4)
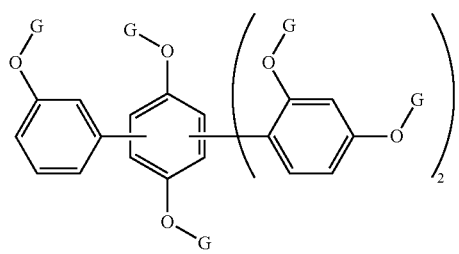

(4'-5)
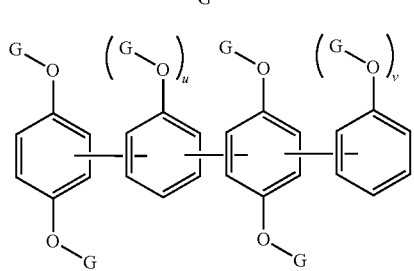

In the formulae, u and v each independently represent 1 or 2.

In a case where the epoxy resin contains another epoxy compound along with the compound represented by Structural Formula (4), since an epoxy resin whose melt viscosity is low and which is excellent in the heat resistance and flame retardancy of a cured product thereof can be obtained, it is preferable that the content ratio of the respective components in the epoxy resin is adjusted such that the total content ratio of the dinuclear compound (x1) in which k in Structural Formula (4) represents 1 and the compound represented by Structural Formula (1-10) is in the range of 5% to 40% in terms of the area ratio in the GPC measurement and the total content ratio of the trinuclear compound (x2) in which k in Structural Formula (4) represents 2, the compound represented by Structural Formula (1-11), the compound represented by Structural Formula (4'-1) or (4'-2) is in the range of 10% to 60%.

An epoxy compound represented by the following Structural Formula (5) can be produced by the above-described method, for example, using parabenzoquinone as the compound (Q) having a quinone structure in the molecular structure and using naphthol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of naphthol to parabenzoquinone at this time is set so that the content of naphthol to 1 mol of parabenzoquinone is in the range of 0.1 mol to 10.0 mol.

[Chem. 27]

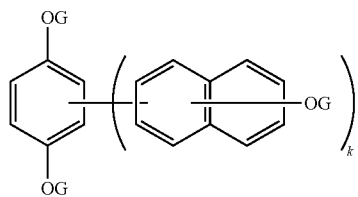

(5)

Among the epoxy compounds represented by Structural Formula (5), since the epoxy compound is particularly excellent in the heat resistance and flame retardancy of a cured product thereof, it is preferable that the epoxy compound is used as an epoxy resin containing a dinuclear compound (x1) in which k in Structural Formula (5) represents 1 and a trinuclear compound (x2) in which k in Structural Formula (5) represents 2 and more preferable that the content ratio of the dinuclear compound (x1) in the epoxy resin is in the range of 5% to 60% in terms of the area ratio in the GPC measurement and the content ratio of the trinuclear compound (x2) is in the range of 5% to 50% in terms of the area ratio in the GPC measurement.

As the compound represented by Structural Formula (5), an epoxy compound represented by any one of the following Structural Formulae (5-1) to (5-10) is exemplified.

[Chem. 28]

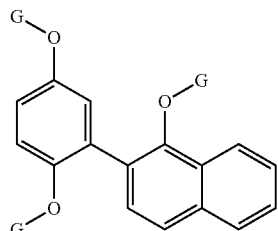

(5-1)

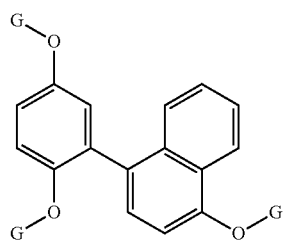

(5-2)

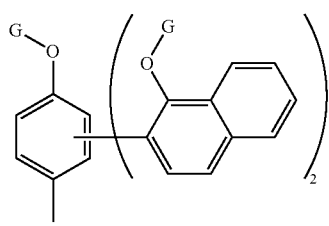

(5-3)

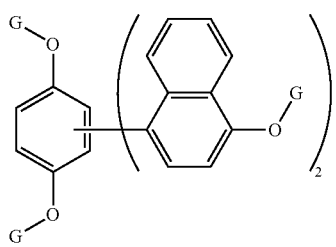

(5-4)

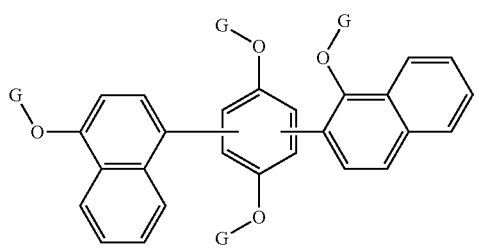

(5-5)

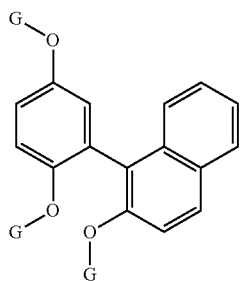

(5-6)

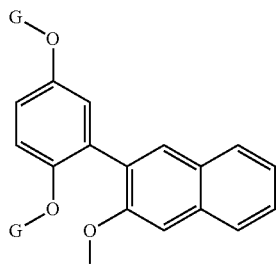

(5-7)

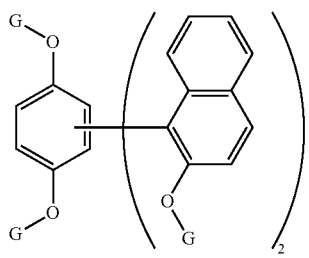

(5-8)

(5-9)

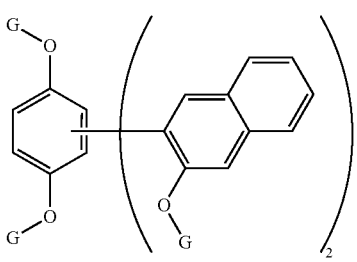

(5-10)

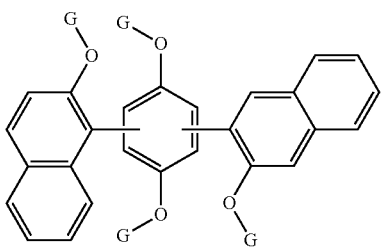

An epoxy compound represented by the following Structural Formula (6) is particularly excellent in the heat resistance and flame retardancy of a cured product thereof among the epoxy compounds represented by Formula (I).

[Chem. 29]

(6)

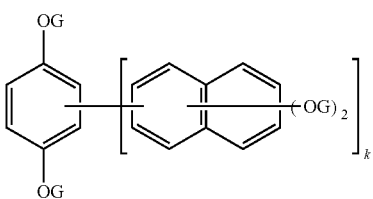

Since the epoxy compound has a low melt viscosity and is more excellent in the heat resistance and flame retardancy of a cured product thereof, it is preferable that the epoxy compound is used as an epoxy resin containing a dinuclear compound (x1) in which k in Structural Formula (6) represents 1 and a trinuclear compound (x2) in which k in Structural Formula (6) represents 2 and more preferable that the content ratio of the dinuclear compound (x1) in the epoxy resin is in the range of 5% to 60% in terms of the area ratio in GPC measurement and the content ratio of the trinuclear compound (x2) is in the range of 5% to 50% in terms of the area ratio in GPC measurement.

The epoxy compound represented by any of Structural Formula (6) can be produced by the above-described method, for example, using parabenzoquinone as the compound (Q) having a quinone structure in the molecular structure and using dihydroxynaphthalene as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of dihydroxynaphthalene to parabenzoquinone at this time is set so that the content of dihydroxynaphthalene to 1 mol of parabenzoquinone is in the range of 0.1 mol to 10.0 mol.

The dihydroxynaphthalene used here may be any position isomer, for example, 1,4-dihydroxynaphthalene, 1,5-dihydroxynaphthalene, 1,6-dihydroxynaphthalene, 2,6-dihydroxynaphthalene, or 2,7-dihydroxynaphthalene. Among these, since an epoxy resin whose melt viscosity is low and which is excellent in heat resistance and flame retardancy of a cured product thereof can be obtained, 2,7-dihydroxynaphthalene is preferable.

As the compound represented by Structural Formula (6), an epoxy compound represented by any one of the following Structural Formulae (6-1) to (6-30) is exemplified.

[Chem. 30]

(6-1)

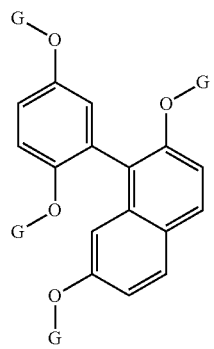

(6-2)

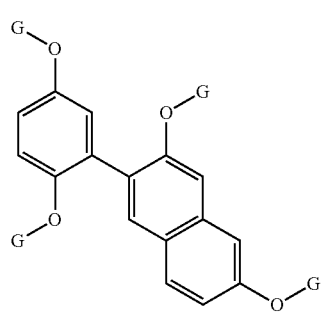

(6-3)

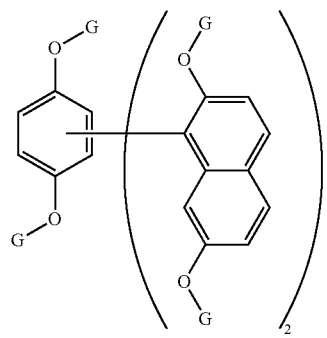

(6-4)

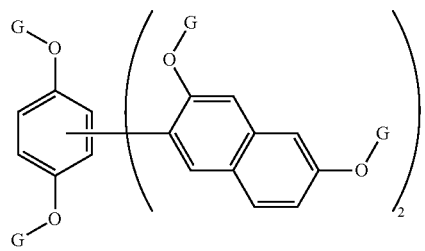

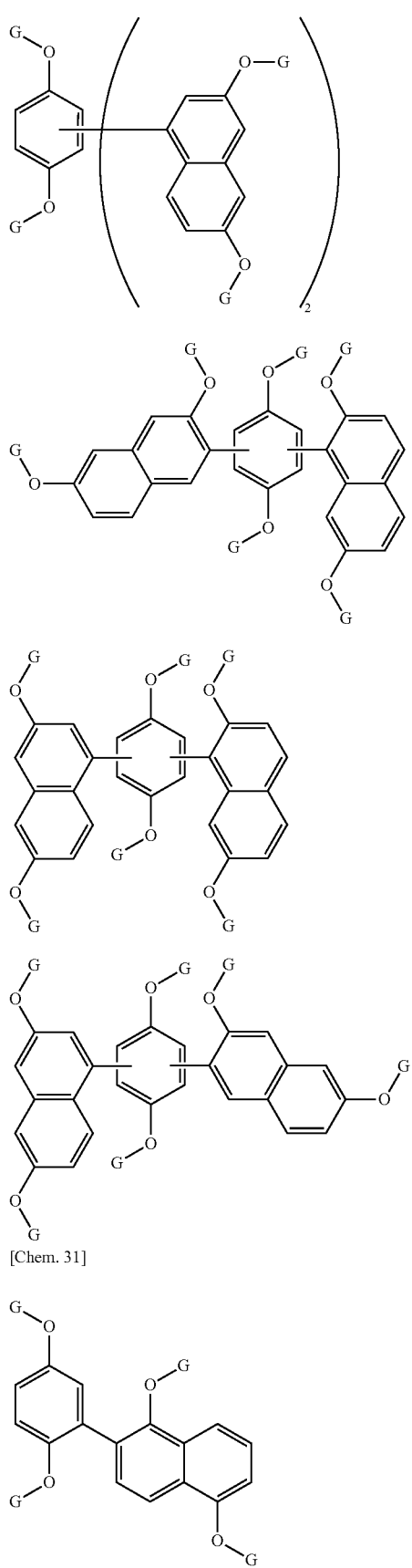
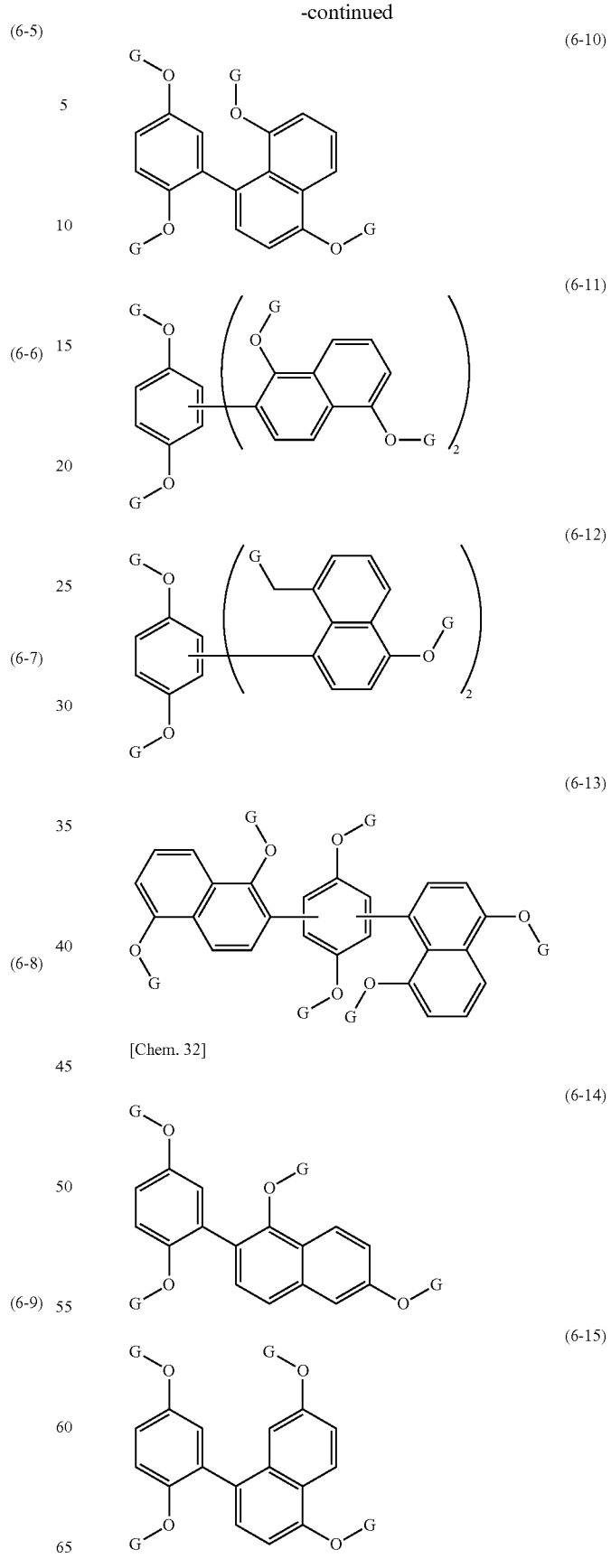
[Chem. 31]
[Chem. 32]

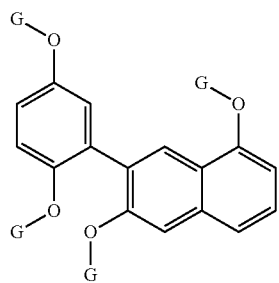
(6-16)
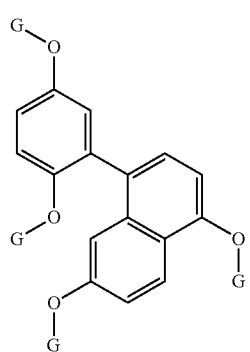
(6-17)
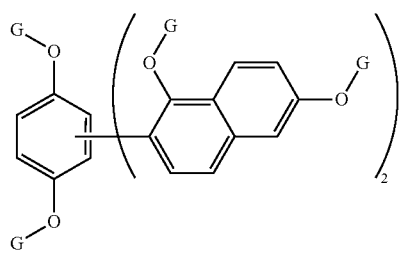
(6-18)
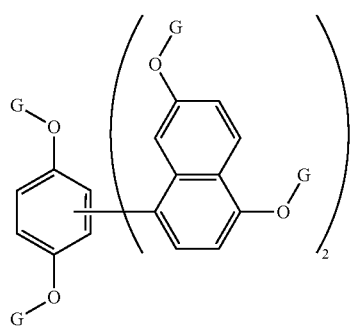
(6-19)
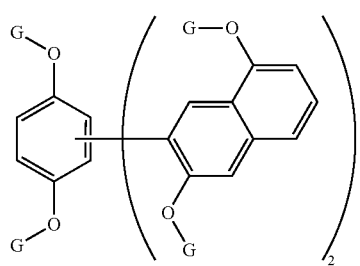
(6-20)
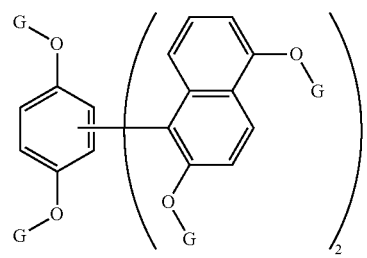
(6-21)
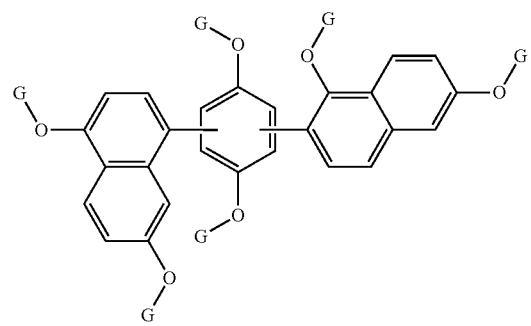
(6-22)
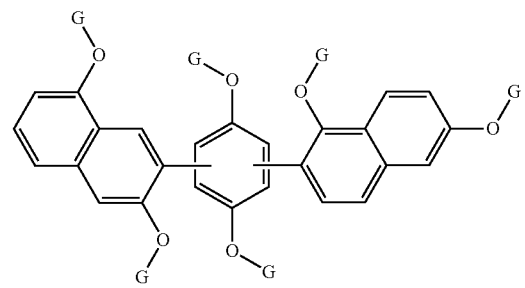
(6-23)
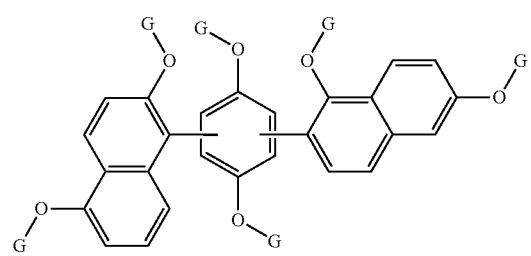
(6-24)
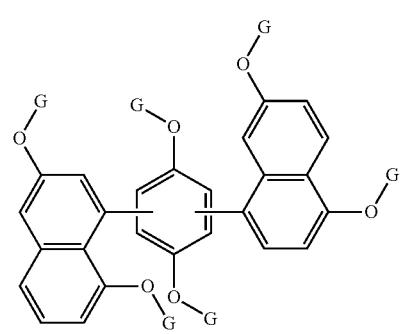
(6-25)

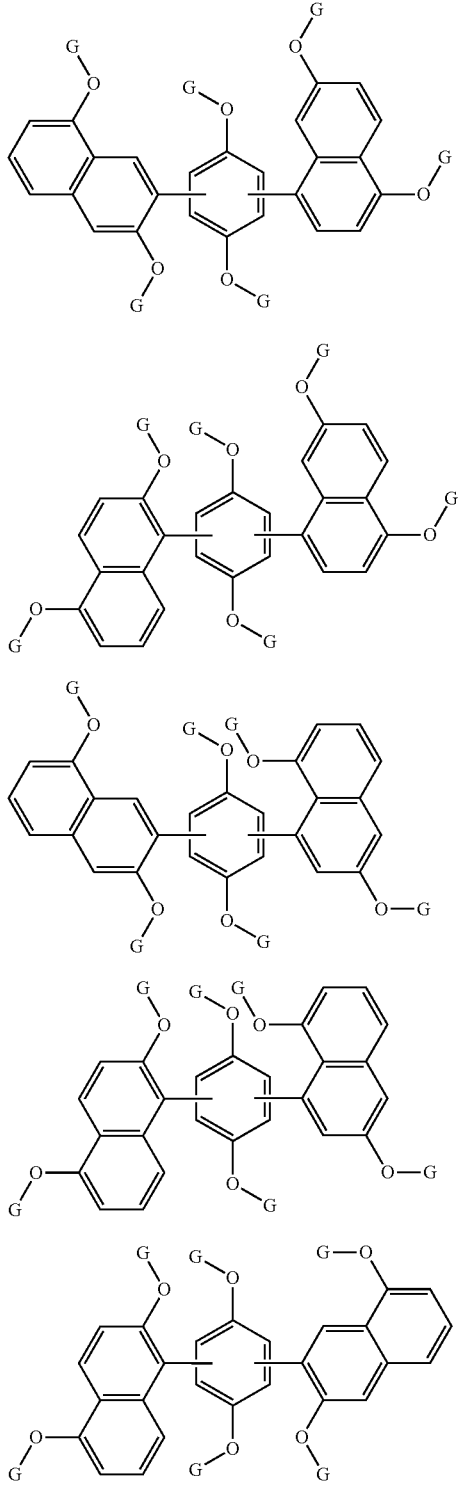

(6-26)
(6-27)
(6-28)
(6-29)
(6-30)

An epoxy compound represented by the following Structural Formula (7) can be produced by the above-described method, for example, using parabenzoquinone as the compound (Q) having a quinone structure in the molecular structure and using phenylphenol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of phenylphenol to parabenzoquinone at this time is set so that the content of phenylphenol to 1 mol of parabenzoquinone is in the range of 0.1 mol to 10.0 mol.

[Chem. 33]

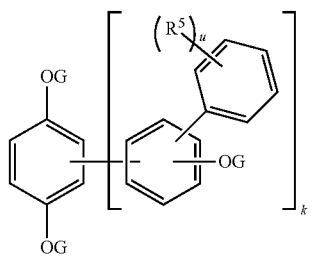

(7)

As the compound represented by Structural Formula (7), an epoxy compound represented by any one of the following Structural Formulae (7-1) to (7-12) is exemplified.

[Chem. 34]

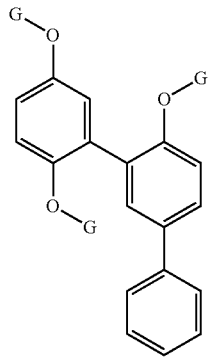

(7-1)

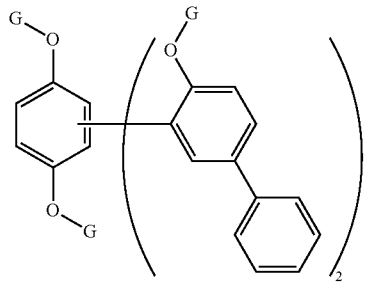

(7-2)

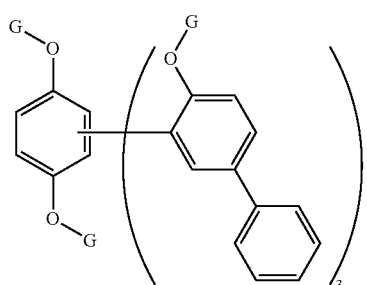

(7-3)

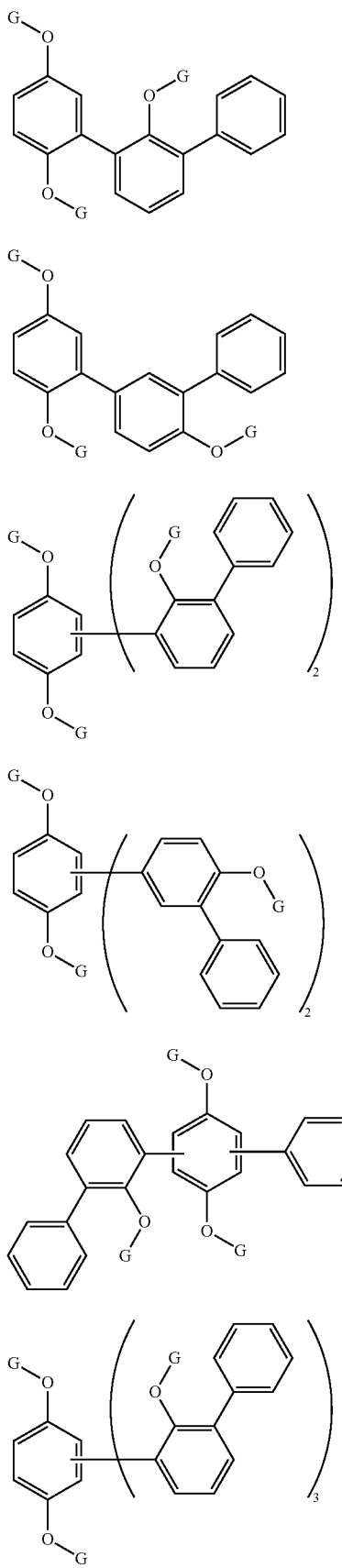
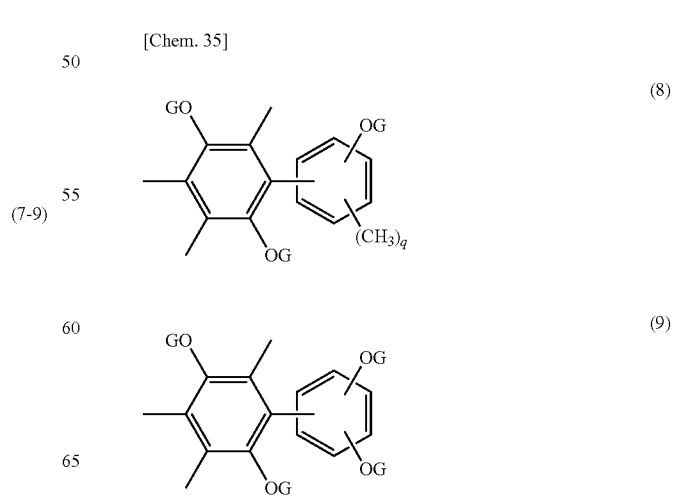
As the epoxy compound represented by Structural Formula (I-2), more specifically, an epoxy compound represented by any one of the following Structural Formulae (8) to (11) is exemplified.
[Chem. 35]

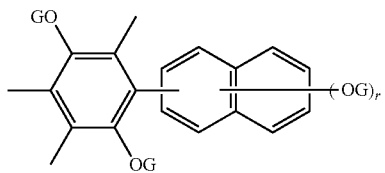 (10)

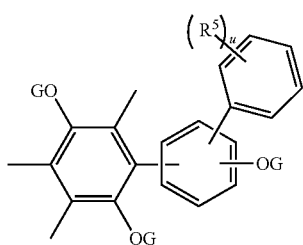 (11)

In Formulae (8) to (11), G represents a glycidyl group, q represents an integer of 0 to 4, and r represents 1 or 2. $R^5$ represents any of an alkyl group having 1 to 4 carbon atoms, an alkoxy group having 1 to 4 carbon atoms, an aryl group, or an aralkyl group, and u represents an integer of 1 to 4. When u represents 2 or greater, a plurality of $R^5$'s may be the same as or different from each other.

Hereinafter, respective epoxy compounds will be described in detail.

An epoxy compound represented by the following Structural Formula (8) can be produced by the above-described method, for example, using 2,4,6-trimethyl-parabenzoquinone as the compound (Q) having a quinone structure in the molecular structure and using phenol, cresol, or dimethylphenol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of the compound (P) having a phenolic hydroxyl group in the molecular structure to 2,4,6-trimethyl-parabenzoquinone at this time is set so that the content of the compound (P) having a phenolic hydroxyl group in the molecular structure to 1 mol of 2,4,6-trimethyl-parabenzoquinone is in the range of 0.1 mol to 10.0 mol.

[Chem. 36]

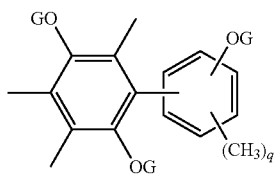 (8)

As the compound represented by Structural Formula (8), an epoxy compound represented by any one of the following Structural Formulae (8-1) to (8-9) is exemplified.

[Chem. 37]

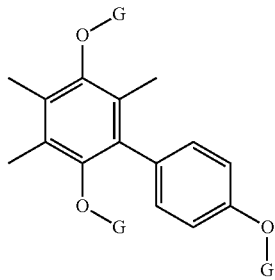 (8-1)

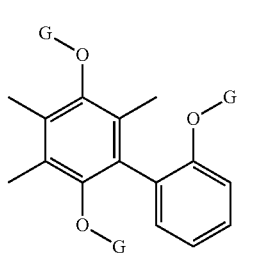 (8-2)

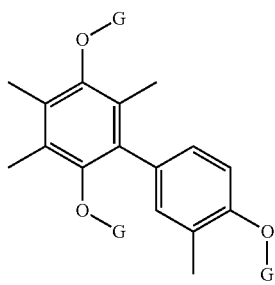 (8-3)

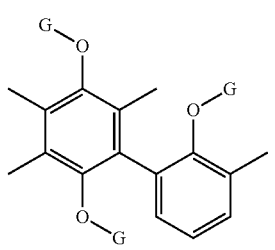 (8-4)

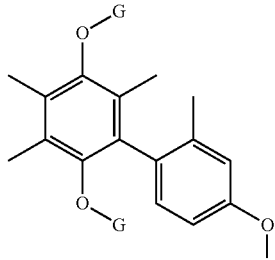 (8-5)

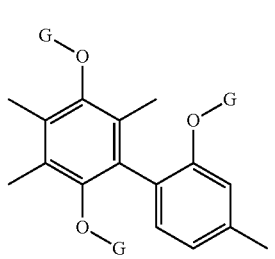 (8-6)

(8-7)

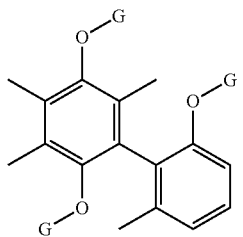

(8-8)

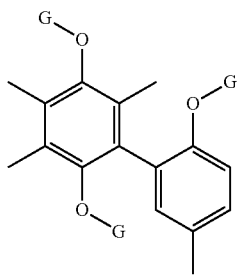

(8-9)

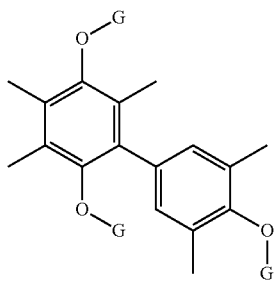

An epoxy compound represented by the following Structural Formula (9) can be produced by the above-described method, for example, using 2,4,6-trimethyl-parabenzoquinone as the compound (Q) having a quinone structure in the molecular structure and using dihydroxybenzene as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of dihydroxybenzene to 2,4,6-trimethyl-parabenzoquinone at this time is set so that the content of dihydroxybenzene to 1 mol of 2,4,6-trimethyl-parabenzoquinone is in the range of 0.1 mol to 10.0 mol.

[Chem. 38]

(9)

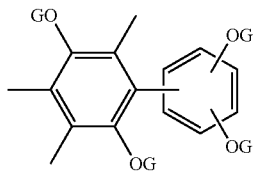

As the compound represented by Structural Formula (9), an epoxy compound represented by the following Formula (9-1) is exemplified.

[Chem. 39]

(9-1)

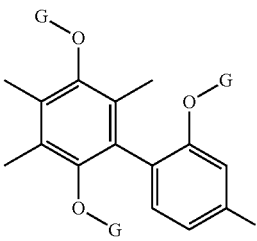

An epoxy compound represented by the following Structural Formula (10) can be produced by the above-described method, for example, using 2,4,6-trimethyl-parabenzoquinone as the compound (Q) having a quinone structure in the molecular structure and using dihydroxynaphthalene or naphthol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of the compound (P) having a phenolic hydroxyl group in the molecular structure to 2,4,6-trimethyl-parabenzoquinone at this time is set so that the content of the compound (P) having a phenolic hydroxyl group in the molecular structure to 1 mol of 2,4,6-trimethyl-parabenzoquinone is in the range of 0.1 mol to 10.0 mol.

[Chem. 40]

(10)

GO
[structure with naphthalene]—(OG)$_r$
OG

As the compound represented by Structural Formula (10), an epoxy compound represented by any one of the following Structural Formulae (10-1) to (10-12) is exemplified.

[Chem. 41]

(10-1)

[structure]

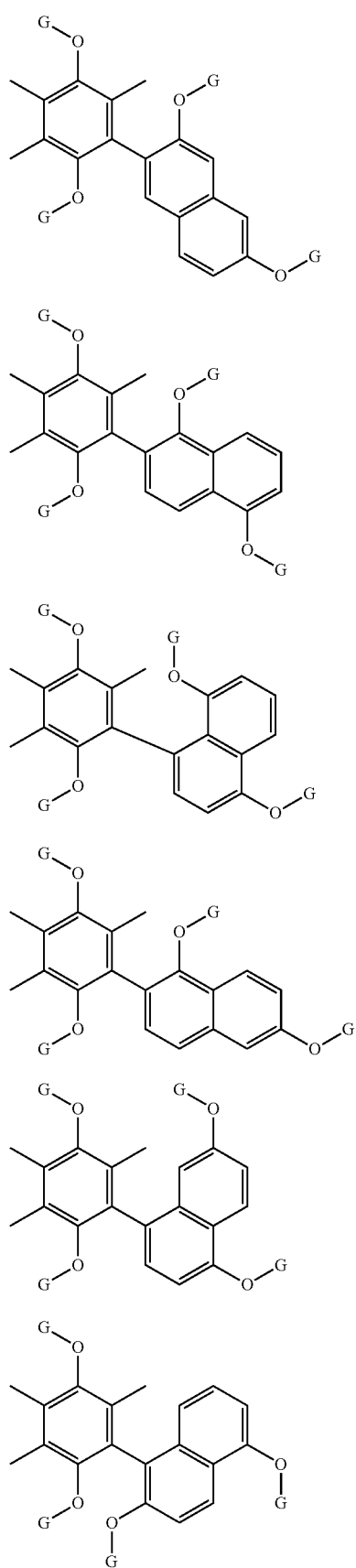

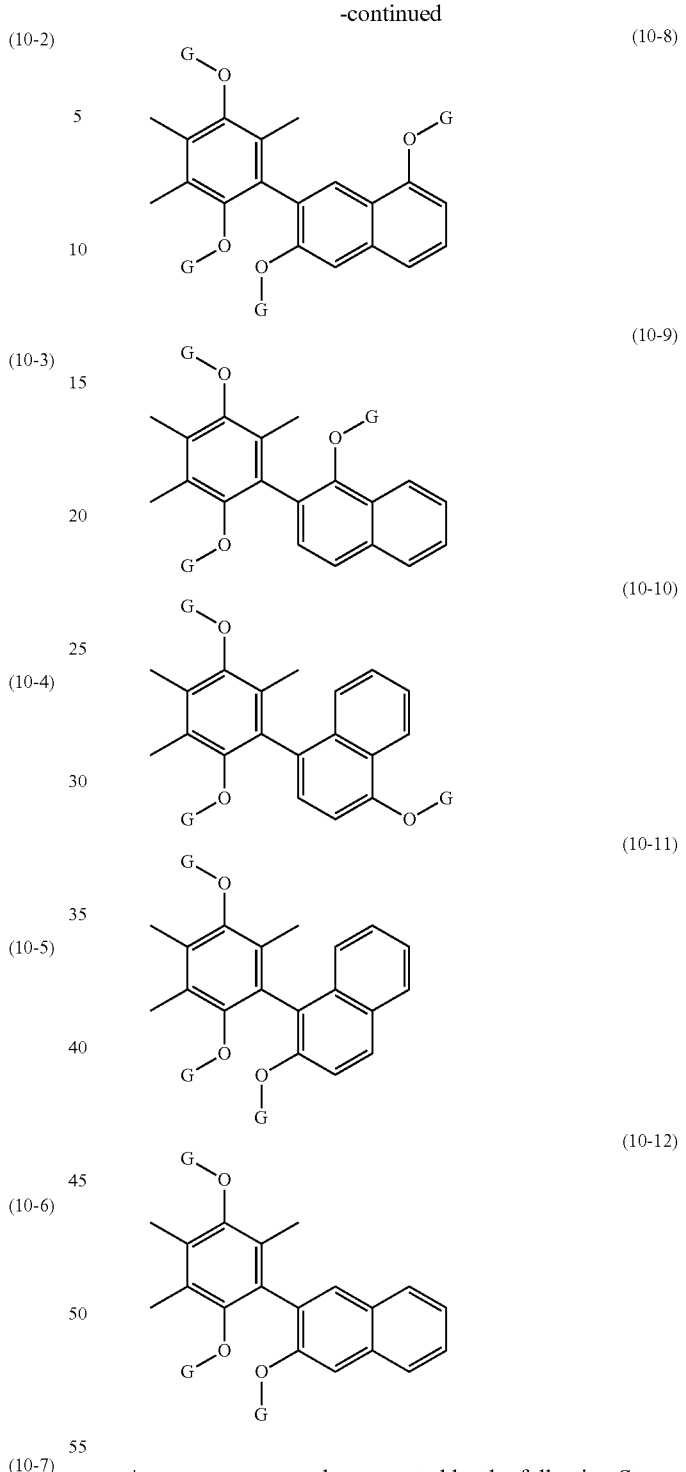

An epoxy compound represented by the following Structural Formula (11) can be produced by the above-described method, for example, using 2,4,6-trimethyl-parabenzoquinone as the compound (Q) having a quinone structure in the molecular structure and using a phenylphenol compound as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of the phenylphenol compound to 2,4,6-trimethyl-parabenzoquinone at this time is set so that the content of the phenylphenol compound in the molecular structure to 1 mol of 2,4,6-trimethyl-parabenzoquinone is in the range of 0.1 mol to 10.0 mol.

[Chem. 42]

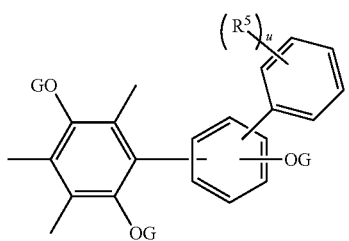
(11)

As the compound represented by Structural Formula (11), an epoxy compound represented by any one of the following Structural Formulae (11-1) to (11-3) is exemplified.

[Chem. 43]

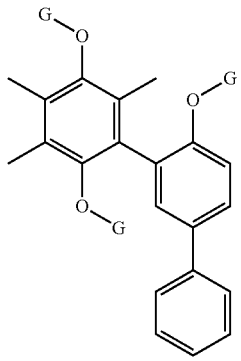
(11-1)

(11-2)

(11-3)

As the epoxy compound represented by Structural Formula (I-3), more specifically, an epoxy compound represented by any one of the following Formulae (12) to (16) is exemplified.

[Chem. 44]

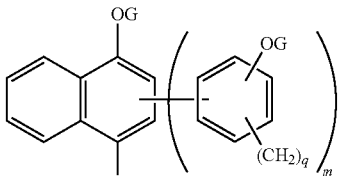
(12)

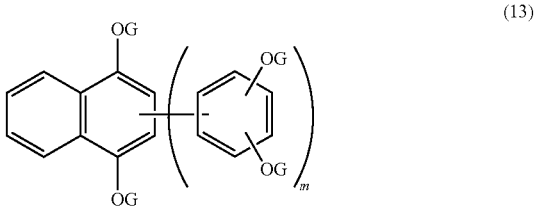
(13)

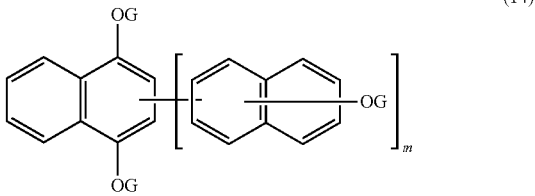
(14)

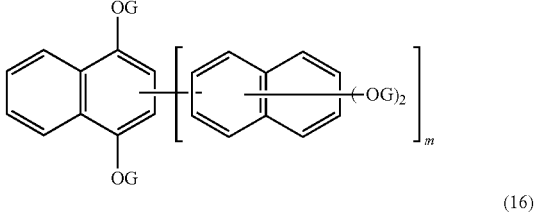
(15)

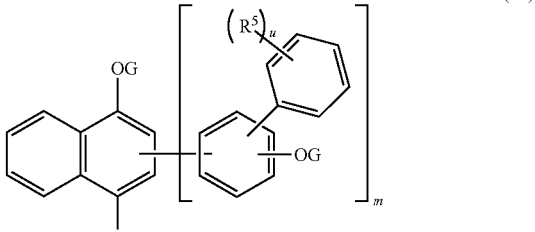
(16)

In Formulae (12) to (16), G represents a glycidyl group, q represents an integer of 0 to 4, and m represents 1 or 2. $R^5$ represents any of an alkyl group having 1 to 4 carbon atoms, an alkoxy group having 1 to 4 carbon atoms, an aryl group, or an aralkyl group, and u represents an integer of 1 to 4. When u represents 2 or greater, a plurality of $R^5$'s may be the same as or different from each other.

Hereinafter, respective epoxy compounds will be described in detail.

An epoxy compound represented by the following Structural Formula (12) can be produced by the above-described method, for example, using naphthoquinone as the compound (Q) having a quinone structure in the molecular structure and using phenol, cresol, or dimethylphenol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of the compound (P) having a phenolic hydroxyl group in the molecular structure to naphthoquinone at this time is set so that the content of the compound (P) having a phenolic hydroxyl group in the molecular structure to 1 mol of naphthoquinone is in the range of 0.1 mol to 10.0 mol.

[Chem. 45]

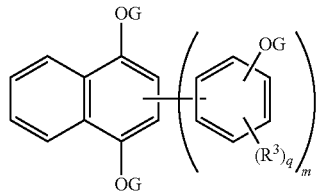

(12)

As the compound represented by Structural Formula (12), an epoxy compound represented by any one of the following Structural Formulae (12-1) to (12-9) is exemplified.

[Chem. 46]

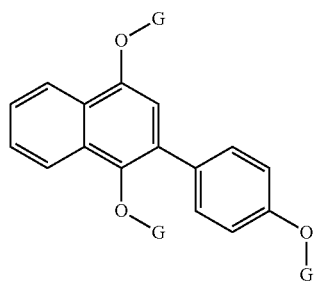

(12-1)

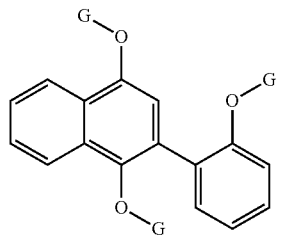

(12-2)

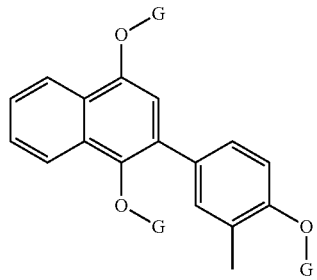

(12-3)

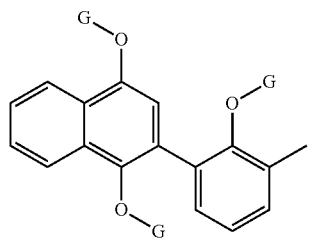

(12-4)

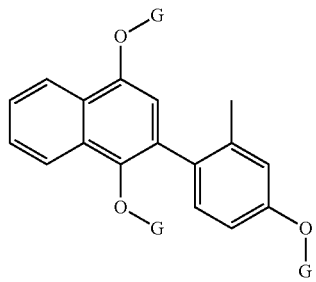

(12-5)

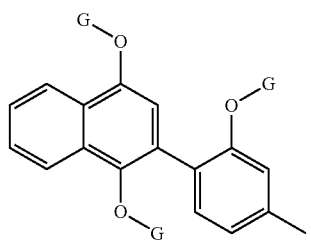

(12-6)

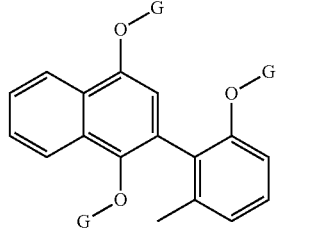

(12-7)

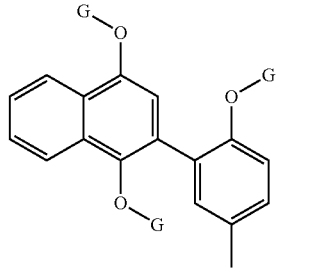

(12-8)

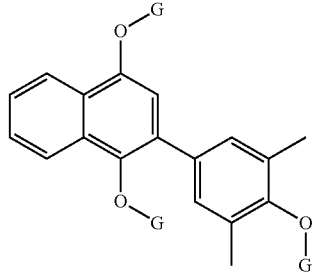

(12-9)

An epoxy compound represented by the following Structural Formula (13) can be produced by the above-described method, for example, using naphthoquinone as the compound (Q) having a quinone structure in the molecular structure and using dihydroxybenzene as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of 1,3-dihydroxybenzene to 2,4,6-trimethyl-parabenzoquinone at this time is set so that the content of dihydroxybenzene to 1 mol of 2,4,6-trimethyl-parabenzoquinone is in the range of 0.1 mol to 10.0 mol.

[Chem. 47]

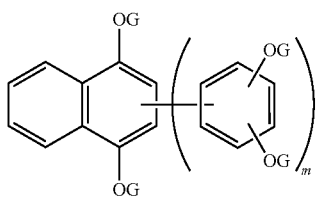

(13)

As the compound represented by Structural Formula (13), an epoxy compound represented by the following Structural Formula (13-1) is exemplified.

[Chem. 48]

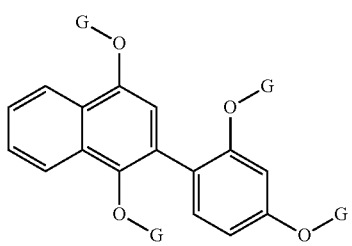

(13-1)

An epoxy compound represented by the following Structural Formula (14) can be produced by the above-described method, for example, using naphthoquinone as the compound (Q) having a quinone structure in the molecular structure and using naphthol as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of naphthol to naphthoquinone at this time is set so that the content of naphthol to 1 mol of naphthoquinone is in the range of 0.1 mol to 10.0 mol.

[Chem. 49]

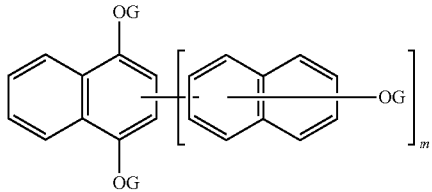

(14)

As the compound represented by Structural Formula (14), an epoxy compound represented by any one of the following Structural Formulae (14-1) to (14-4) is exemplified.

[Chem. 50]

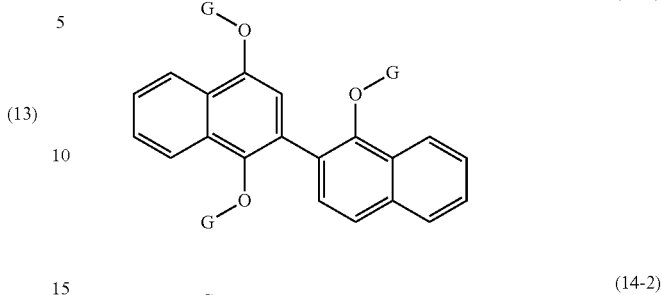

(14-1)

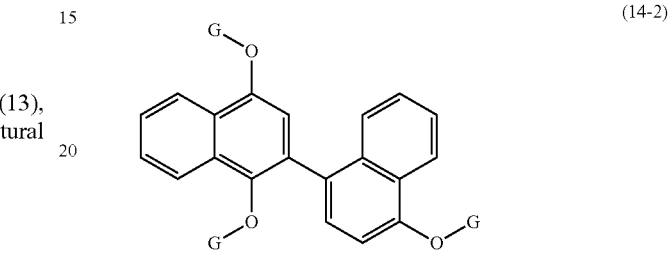

(14-2)

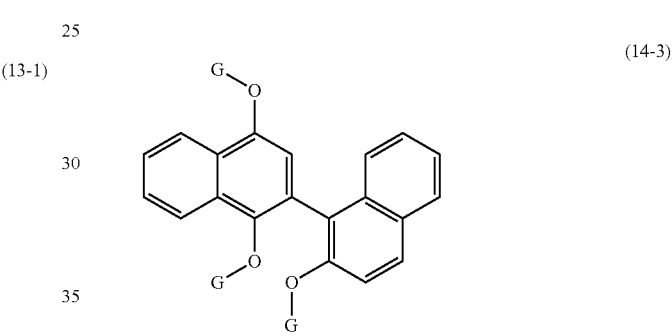

(14-3)

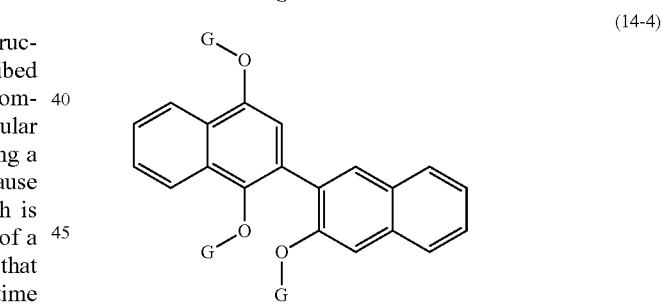

(14-4)

An epoxy compound represented by the following Structural Formula (15) is particularly excellent in heat resistance and flame retardancy of a cured product thereof among the epoxy compounds represented by Formula (I). The epoxy compound represented by the following Structural Formula (15) can be produced by the above-described method, for example, using naphthoquinone as the compound (Q) having a quinone structure in the molecular structure and using dihydroxynaphthalene as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of dihydroxynaphthalene to naphthoquinone at this time is set so that the content of dihydroxynaphthalene to 1 mol of naphthoquinone is in the range of 0.1 mol to 10.0 mol.

[Chem. 51]

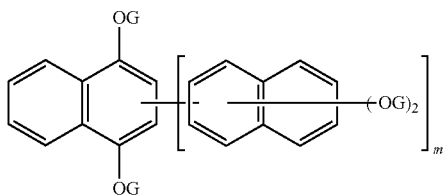 (15)

The dihydroxynaphthalene used here may be any position isomer, for example, 1,4-dihydroxynaphthalene, 1,5-dihydroxynaphthalene, 1,6-dihydroxynaphthalene, 2,6-dihydroxynaphthalene, or 2,7-dihydroxynaphthalene. Among these, since an epoxy resin whose melt viscosity is low and which is excellent in heat resistance and flame retardancy of a cured product thereof can be obtained, 2,7-dihydroxynaphthalene is preferable.

As the compound represented by Structural Formula (15), an epoxy compound represented by any one of the following Structural Formulae (15-1) to (15-8) is exemplified.

[Chem. 52]

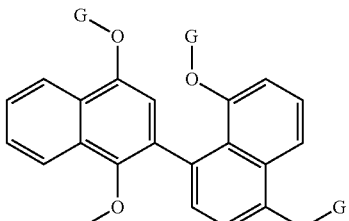 (15-4)

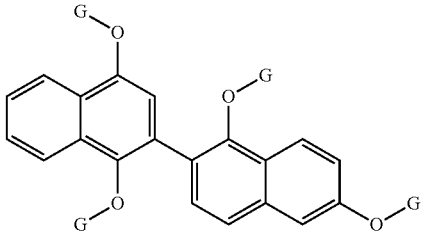 (15-5)

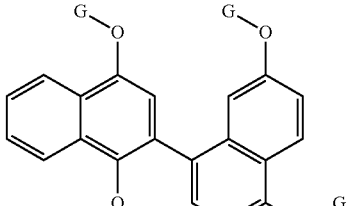 (15-6)

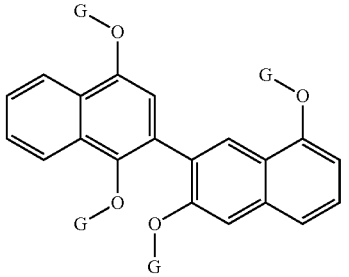 (15-7)

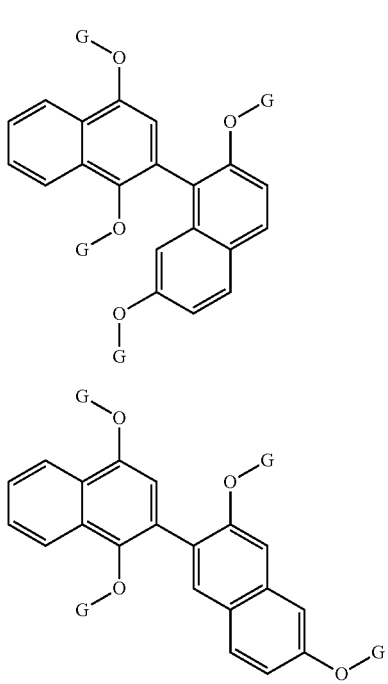 (15-1) (15-2) (15-3)

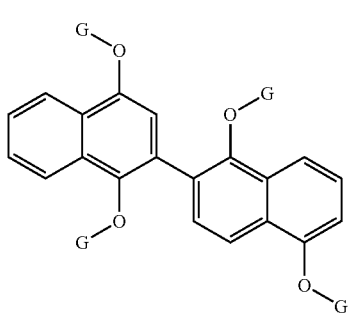 (15-8)

An epoxy resin containing the epoxy compound represented by Structural Formula (15) may further contain an epoxy compound other than these. Among other epoxy compounds, it is preferable that a dinaphthofuran compound represented by the following Structural Formula (15') is contained because of excellent flame retardancy of a cured product thereof. In this case, it is preferable that the content ratio of the respective components in the epoxy resin is adjusted such that the content ratio of the dinuclear compound (x1) in which m in Structural Formula (15) represents 1 is in the range of 2% to 60% in terms of the area ratio in the GPC measurement and the content ratio of the dinaphthofuran compound is in the range of 1% to 60%.

[Chem. 53]

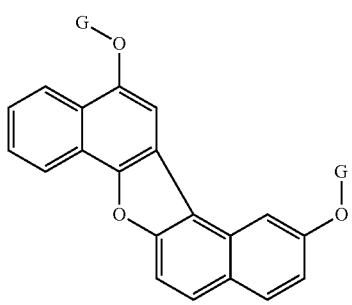
(15′)

An epoxy compound represented by the following Structural Formula (16) can be produced by the above-described method, for example, using naphthoquinone as the compound (Q) having a quinone structure in the molecular structure and using a phenylphenol compound as the compound (P) having a phenolic hydroxyl group in the molecular structure. Because an epoxy resin whose melt viscosity is low and which is more excellent in heat resistance and flame retardancy of a cured product thereof can be obtained, it is preferable that the reaction ratio of the phenylphenol compound to naphthoquinone at this time is set so that the content of the phenylphenol compound to 1 mol of naphthoquinone is in the range of 0.1 mol to 10.0 mol.

[Chem. 54]

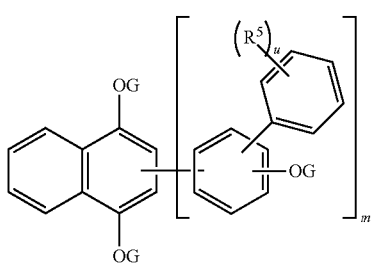
(16)

As the compound represented by Structural Formula (16), an epoxy compound represented by any one of the following Structural Formulae (16-1) to (16-7) is exemplified.

[Chem. 55]

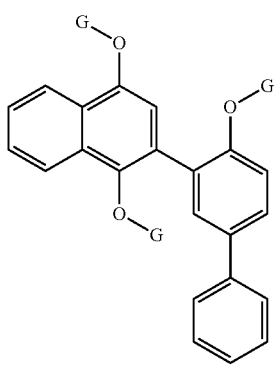
(16-1)

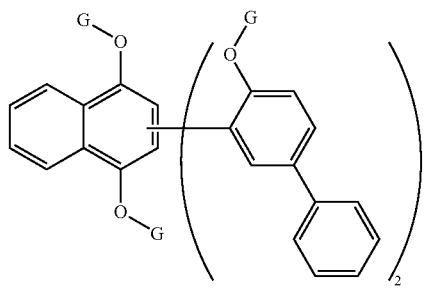
(16-2)

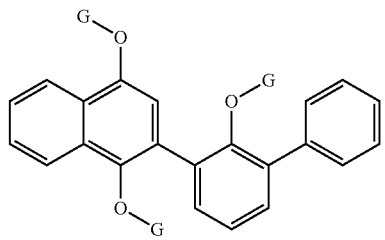
(16-3)

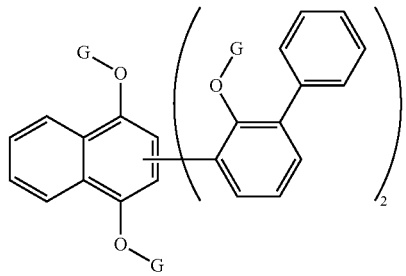
(16-4)

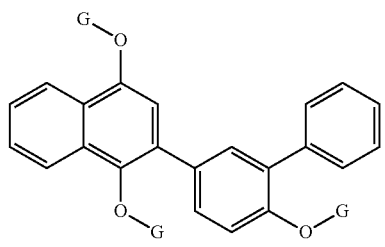
(16-5)

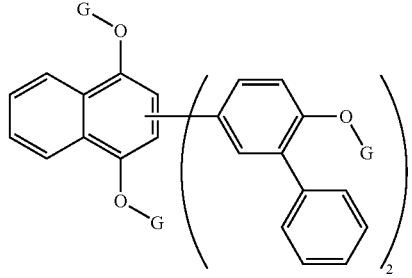
(16-6)

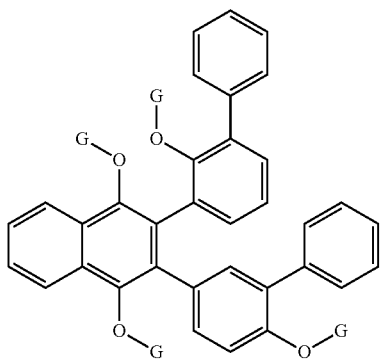 (16-7)

From among the epoxy compounds exemplified above, the epoxy compound represented by any one of Structural Formulae (1) to (3) is preferable in terms of low melt viscosity and excellent balance between heat resistance and flame retardancy of a cured product thereof and the epoxy compound represented by Structural Formula (1) is more preferable in terms of particularly low melt viscosity.

In addition, the epoxy compound represented by Structural Formula (6) or (15) is preferable in terms of particularly excellent heat resistance and flame retardancy of a cured product thereof and the epoxy compound represented by Structural Formula (15-1) or (15-2) is more preferable in terms of particularly excellent flame retardancy.

It is preferable that the epoxy equivalent of the epoxy resin containing the epoxy compound of the present invention is in the range of 125 g/eq to 300 g/eq in terms of excellent curing properties. Further, it is preferable that the melt viscosity to be measured under a temperature condition of 150° C. is in the range of 0.1 dPa·s to 4.0 dPa·s.

The curable composition of the present invention includes the epoxy compound described above or the epoxy resin containing the epoxy compound and a curing agent as essential components.

Examples of the curing agent used here include various known curing agents such as an amine-based compound, an amide-based compound, an acid anhydride-based compound, and a phenol-based compound. Specific examples of the amine-based compound include diaminodiphenylmethane, diethylenetriamine, triethylenetetramine, diaminodiphenylsulfone, isophoronediamine, imidazole, a $BF_3$-amine complex, and a guanidine derivative; specific examples of the amide-based compound include dicyandiamide and a polyamide resin synthesized by a dimer of linolenic acid and ethylenediamine; specific examples of the acid anhydride-based compound include phthalic anhydride, trimellitic anhydride, pyromellitic anhydride, maleic anhydride, tetrahydrophthalic anhydride, methyltetrahydrophthalic anhydride, methyl nadic anhydride, hexahydrophthalic anhydride, and methylhexahydrophthalic anhydride; and specific examples of the phenol-based compound include polyhydric phenol compounds such as a phenol novolac resin, a cresol novolac resin, an aromatic hydrocarbon formaldehyde resin-modified phenol resin, a dicyclopentadienephenol addition type resin, a phenol aralkyl resin (xylok resin), a naphthol aralkyl resin, a trimethylol methane resin, a tetraphenylolethane resin, a naphthol novolac resin, a naphthol-phenol co-condensed novolac resin, a naphthol-cresol co-condensed novolac resin, a biphenyl-modified phenol resin (a polyhydric phenol compound to which a phenol nucleus is linked by a bismethylene group), a biphenyl-modified naphthol resin (a polyhydric naphthol compound to which a phenol nucleus is linked by a bismethylene group), an aminotriazine-modified phenol resin (a polyhydric phenol compound to which a phenol nucleus is linked by melamine or benzoguanamine), and an alkoxy group-containing aromatic ring-modified novolac resin (a polyhydric phenol compound to which a phenol nucleus and an alkoxy group-containing aromatic ring are linked by formaldehyde).

In the curable composition of the present invention, because a curable composition which has high curing properties and is excellent in heat resistance and flame retardancy of a cured product thereof can be obtained, it is preferable that the mixing ratio of an epoxy compound or an epoxy resin and a curing agent is adjusted such that the equivalent ratio (epoxy group/active hydrogen atom) of an epoxy group in the epoxy compound or the epoxy resin to an active hydrogen atom in the curing agent is in the range of 1/0.5 to 1/1.5.

The curable composition of the present invention may include other epoxy resins in addition to the epoxy compound of the present invention.

Specific examples of other epoxy resins used here include a naphthalene skeleton-containing epoxy resin such as 2,7-diglycidyloxynaphthalene, an α-naphthol novolac type epoxy resin, a β-naphthol novolac type epoxy resin, polyglycidyl ether of α-naphthol/β-naphthol co-condensed novolac, a naphthol aralkyl type epoxy resin, or 1,1-bis(2,7-diglycidyloxy-1-naphthyl)alkane; a bisphenol type epoxy resin such as a bisphenol A type epoxy resin or a bisphenol F type epoxy resin; a biphenyl type epoxy resin such as a biphenyl type epoxy resin or a tetramethyl biphenyl type epoxy resin; a novolac type epoxy resin such as a phenol novolac type epoxy resin, a cresol novolac type epoxy resin, a bisphenol A novolac type epoxy resin, an epoxide of a condensate of a phenol-based compound and aromatic aldehyde including a phenolic hydroxyl group, or a biphenyl novolac type epoxy resin; a triphenyl methane type epoxy resin; a tetraphenyl ethane type epoxy resin; a dicyclopentadiene-phenol addition reaction type epoxy resin; a phenol aralkyl type epoxy resin; and a phosphorus atom-containing epoxy resin.

Here, examples of the phosphorus atom-containing epoxy resin include an epoxide of 9,10-dihydro-9-oxa-10-phosphaphenanthrene-10-oxide (hereinafter, abbreviated as "HCA"), an epoxide of a phenol resin obtained by reacting HCA and quinones, an epoxy resin obtained by modifying a phenol novolac type epoxy resin using HCA, an epoxy resin obtained by modifying a cresol novolac type epoxy resin using HCA, and an epoxy resin obtained by modifying a bisphenol A type epoxy resin using a phenol resin obtained by reacting HCA with quinones.

In a case of using other epoxy resins described above, because the effects, which are the characteristics of the epoxy compound of the present invention, that is, low melt viscosity and excellent heat resistance and flame retardancy of a cured product thereof, are sufficiently exhibited, it is preferable the epoxy resins are used so that the content of the epoxy compound of the present invention is 50% by mass or greater based on all the epoxy resin components.

Moreover, in a case of using other epoxy resins described above, because a curable composition which has high curing properties and is excellent in heat resistance and flame retardancy of a cured product thereof can be obtained, it is preferable that the mixing ratio of the curable composition is adjusted such that the equivalent ratio (epoxy group/active hydrogen atom) of an epoxy group in all the epoxy components to an active hydrogen atom in the curing agent is in the range of 1/0.5 to 1/1.5.

A curing accelerator can be appropriately used together with the curable composition of the present invention as needed. Various kinds of curing accelerators can be used as the curing accelerator described above and examples thereof include a phosphorus-based compound, tertiary amine, imidazole, an organic acid metal salt, Lewis acid, and an amine complex salt. Particularly, in a case where the curable composition is used for a semiconductor sealing material, 2-ethyl-4-methylimidazole is preferable for an imidazole compound, triphenylphosphine is preferable for a phosphorus-based compound, and 1,8-diazabicyclo-[5,4,0]-undecene (DBU) is preferable for a tertiary amine in terms of excellent curing properties, heat resistance, electrical characteristics, moisture resistance reliability, and the like.

The curable composition of the present invention described above may further contain other additive components depending on the applications or desired performance. Specifically, for the purpose of further improving the flame retardancy, a non-halogen-based flame retardant which does not substantially contain halogen atoms may be mixed.

Examples of the non-halogen-based flame retardant include a phosphorus-based flame retardant, a nitrogen-based flame retardant, a silicone-based flame retardant, an inorganic flame retardant, and an organic metal salt-based flame retardant, and the use thereof is not particularly limited and these may be used alone, in the plural of the same kind of flame retardants, or in combination of different kinds of flame retardants.

As the phosphorus-based flame retardant, any of an inorganic flame retardant and an organic flame retardant can be used. Examples of the inorganic compound include red phosphorus and an inorganic nitrogene-containing phosphorus compound such as ammonium phosphates, e.g., monoammonium phosphate, diammonium phosphate, triammonium phosphate or ammonium polyphosphate; and amide phosphate.

Moreover, it is preferable that the red phosphorus is subjected to a surface treatment for the purpose of prevention of hydrolysis or the like, and examples of the surface treatment method include (i) a method of carrying out a treatment of coating the surface with an inorganic compound such as magnesium hydroxide, aluminum hydroxide, zinc hydroxide, titanium hydroxide, bismuth oxide, bismuth hydroxide, bismuth nitrate, or a mixture of these; (ii) a method of carrying out a treatment of coating the surface with a mixture of an inorganic compound such as magnesium hydroxide, aluminum hydroxide, zinc hydroxide, or titanium hydroxide, and thermosetting resins such as a phenol resin; (iii) a method of carrying out a treatment of coating the surface with an inorganic compound such as magnesium hydroxide, aluminum hydroxide, zinc hydroxide, or titanium hydroxide and then doubly coating with a thermosetting resin such as a phenol resin.

Examples of the organic phosphorus compound include a cyclic organic phosphorus compound such as 9,10-dihydro-9-oxa-10-phosphaphenanthrene-10-oxide, 10-(2,5-dihydroxyphenyl)-10H-9-oxa-10-phosphaphenanthrene-10-oxide, or 10-(2,7-dihydroxynaphthyl)-10H-9-oxa-10-phosphaphenanthrene-10-oxide; and a derivative obtained by reacting the cyclic organic phosphorus compound with a compound such as an epoxy resin or a phenol resin in addition to a general-purpose organic phosphorus-based compound such as a phosphoric ester compound, a phosphonic acid compound, a phosphinic acid compound, a phosphine oxide compound, a phosphorane compound, and an organic nitrogen-containing phosphorus compound.

The mixing amount thereof is appropriately selected according to the kind of a phosphorus-based flame retardant, other components of the curable composition, and the degree of desired flame retardancy, but it is preferable that the mixing amount of red phosphorus is in the range of 0.1 parts by mass to 2.0 parts by mass in a case where red phosphorus is used as a non-halogen-based flame retardant, and it is preferable that the mixing amount of an organic phosphorus compound is in the range of 0.1 parts by mass to 10.0 parts by mass and particularly preferable that the mixing amount thereof is in the range of 0.5 parts by mass to 6.0 parts by mass in a case of using an organic phosphorus compound, based on 100 parts by mass of the curable composition obtained by mixing all of the epoxy components, a curing agent, and other additives or a filler.

Further, in a case of using the phosphorus-based flame retardant, hydrotalcite, magnesium hydroxide, a boron compound, zirconium oxide, a black dye, calcium carbonate, zeolite, zinc molybdate, or activated carbon may be used together with the phosphorus-based flame retardant.

Examples of the nitrogen-based flame retardant include a triazine compound, a cyanuric acid compound, an isocyanuric acid compound, and phenothiazine, and a triazine compound, a cyanuric acid compound, and an isocyanuric acid compound are preferable.

Examples of the triazine compound include (i) an aminotriazine sulfate compound such as guanyl melamine sulfate, melem sulfate, or melam sulfate; (ii) a co-condensate of a phenol-based compound such as phenol, cresol, xylenol, butylphenol or nonylphenol, a melamine such as melamine, benzoguanamine, acetoguanamine or formguanamine, and formaldehyde; (iii) a mixture of the co-condensate of the above (ii) and a phenol resin such as a phenolformaldehyde condensate; (iv) a compound obtained by modifying (ii) and (iii) using tung oil, isomerized linseed oil, and the like, in addition to melamine, acetoguanamine, benzoguanamine, melon, melam, succinoguanamine, ethylene dimelamine, melamine polyphosphate, and triguanamine.

Specific examples of the cyanuric acid compound include cyanuric acid and melamine cyanurate.

The mixing amount of the nitrogen-based flame retardant is appropriately selected according to the kind of the nitrogen-based flame retardant, other components of the curable resin composition, and the degree of desired flame retardancy, but it is preferable that the content of the nitrogen-based flame retardant is in the range of 0.05 parts by mass to 10 parts by mass and particularly preferable that the content thereof is in the range of 0.1 parts by mass to 5 parts by mass based on 100 parts by mass of the curable composition obtained by mixing all of the epoxy components, a curing agent, other additives, and a filler.

Moreover, when the nitrogen-based flame retardant is used, a metal hydroxide or a molybdenum compound may be used together with the nitrogen-based flame retardant.

The silicone-based flame retardant can be used without particular limitation as long as the silicone-based flame retardant is an organic compound containing silicon atoms, and examples thereof include silicone oil, silicone rubber, and a silicone resin.

The mixing amount of the silicone-based flame retardant is appropriately selected according to the kind of the silicone-based flame retardant, other components of the curable composition, and the degree of desired flame retardancy, but it is preferable that the content of the silicone-based flame retardant is in the range of 0.05 parts by mass to 20 parts by mass based on 100 parts by mass of the curable composition obtained by mixing all of the epoxy components, a curing agent, other additives, and a filler. In addition, when the silicone-based flame retardant is used, a molybdenum compound or alumina may be used together with the silicone-based flame retardant.

Examples of the inorganic flame retardant include a metal hydroxide, a metal oxide, a metal carbonate compound, metal powder, a boron compound, low melting point glass.

Specific examples of the metal hydroxide include aluminum hydroxide, magnesium hydroxide, dolomite, hydrotalcite, calcium hydroxide, barium hydroxide, and zirconium hydroxide.

Specific examples of the metal oxide include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Specific examples of the metal carbonate compound include zinc carbonate, magnesium carbonate, calcium carbonate, barium carbonate, basic magnesium carbonate, aluminum carbonate, iron carbonate, cobalt carbonate, and titanium carbonate.

Specific examples of the metal powder include aluminum, iron, titanium, manganese, zinc, molybdenum, cobalt, bismuth, chromium, nickel, copper, tungsten, and tin.

Specific examples of the boron compound include zinc borate, zinc metaborate, barium metaborate, boric acid, and borax.

Specific examples of the low melting point glass include glass-like compounds such as CEEPREE (ARBROWN CO., LTD), hydrated glass $SiO_2$—$MgO$—$H_2O$, a $PbO$—$B_2O_3$-based compound, a $ZnO$—$P_2O_5$—$MgO$-based compound, a $P_2O_5$—$B_2O_3$—$PbO$—$MgO$-based compound, a $P$—$Sn$—$O$—$F$-based compound, a $PbO$—$V_2O_5$—$TeO_2$-based compound, a $Al_2O_3$—$H_2O$-based compound, a lead borosilicate-based compound.

The mixing amount of the inorganic flame retardant is appropriately selected according to the kind of the inorganic flame retardant, other components of the curable composition, and the degree of desired flame retardancy, but it is preferable that the content of the inorganic flame retardant is in the range of 0.5 parts by mass to 50 parts by mass and particularly preferable that the content thereof is in the range of 5 parts by mass to 30 parts by mass based on 100 parts by mass of the curable composition obtained by mixing all of the epoxy components, a curing agent, other additives, and a filler.

Examples of the organic metal salt-based flame retardant include ferrocene, an acetylacetonate metal complex, an organic metal carbonyl compound, an organic cobalt salt compound, an organic sulfonic acid metal salt, and a compound in which a metal atom and an aromatic compound or a heterocyclic compound is ionically or coordinately bonded.

The mixing amount of the organic metal salt-based flame retardant is appropriately selected according to the kind of the organic metal salt-based flame retardant, other components of the curable composition, and the degree of desired flame retardancy, but it is preferable that the content of the organic metal salt-based flame retardant is in the range of 0.005 parts by mass to 10 parts by mass based on 100 parts by mass of the curable composition obtained by mixing all of the epoxy components, a curing agent, other additives, and a filler.

In addition, various compounding agents such as a silane coupling agent, a release agent, a pigment, and an emulsifying agent can be added to the curable composition of the present invention as needed.

An inorganic filler can be mixed with the curable composition of the present invention as needed. Since the epoxy compound and the epoxy resin of the present invention have a low melt viscosity, the mixing amount of the inorganic filler can be increased and such a curable composition can be suitably used particularly for a semiconductor sealing material.

Examples of the inorganic filler include fused silica, crystalline silica, alumina, silicon nitride, and aluminum hydroxide. Among these, the fused silica is preferable from a viewpoint that a larger amount of inorganic filler can be mixed. The fused silica can be used in the form of a fragment or a sphere, but it is preferable to mainly use spherical fused silica in order to increase the mixing amount of fused silica and to suppress an increase in melt viscosity of the curable composition. Further, for the purpose of increasing the mixing amount of spherical silica, it is preferable to appropriately adjust particle size distribution of the spherical silica. The filling rate thereof is preferably in the range of 0.5 parts by mass to 95 parts by mass based on 100 parts by mass of the curable composition.

In addition, when the curable composition of the present invention is used for conductive paste or the like, a conductive filler such as silver powder or copper powder can be used.

In a case where the curable composition of the present invention is adjusted to a varnish for a printed circuit board, it is preferable to mix an organic solvent. Examples of the organic solvent being used here include methyl ethyl ketone, acetone, dimethylformamide, methyl isobutyl ketone, methoxy propanol, cyclohexanone, methyl cellosolve, ethyl diglycol acetate, and propylene glycol monomethyl ether acetate, and the selection and the appropriate amount to be used can be suitably selected based on the application thereof. For example, when the organic solvent is used for a printed circuit board, a polar solvent whose boiling point is 160° C. or lower, such as methyl ethyl ketone, acetone, or dimethylformamide is preferable and it is preferable that the solvent is used such that the non-volatile content is in the range of 40% by mass to 80% by mass. Meanwhile, when the organic solvent is used for an adhesive film for build-up, as the organic solvent, it is preferable to use ketones such as acetone, methyl ethyl ketone, and cyclohexanone; acetates such as ethyl acetate, butyl acetate, cellosolve acetate, propylene glycol monomethyl ether acetate, and carbitol acetate; carbitols such as cellosolve and butyl carbitol; aromatic hydrocarbons such as toluene and xylene; dimethylformamide, dimethylacetamide, or N-methylpyrrolidone. Further, it is preferable that the solvent is used such that the non-volatile content is in the range of 30% by mass to 60% by mass.

The curable composition of the present invention can be obtained by uniformly mixing the above-described respective components. The curable composition of the present invention in which an epoxy resin component, a curing agent, and optionally a curing accelerator are mixed can be easily made into a cured product by the same method as a known method of the related art. As the cured product, a molded cured product such as a laminate, a cast product, an adhesive layer, a coating film or a film is exemplified.

The epoxy compound of the present invention can be used for various electronic materials because of low melt viscosity and excellent heat resistance and flame retardancy of a cured product. Among the applications, the epoxy compound can be suitably used particularly for a semiconductor sealing material by applying the low melt viscosity.

The semiconductor sealing material can be prepared by a method of sufficiently mixing a mixture of an epoxy component containing the epoxy compound of the present invention, a curing agent, and a filler until the mixture becomes uniform using an extruder, a kneader, or a roller. As the filler used here, the inorganic filler described above is exemplified. Further, as described above, the content of the inorganic filler is preferably in the range of 0.5 parts by mass to 95 parts by mass based on 100 parts by mass of the curable composition. From viewpoints that flame retardancy, moisture resistance, or solder crack resistance is improved and a linear expansion coefficient can be decreased, the content of the filler is preferably in the range of 70 parts by mass to 95 parts by mass and particularly preferably in the range of 80 parts by mass to 95 parts by mass.

As a method of molding a semiconductor package using the obtained semiconductor sealing material, a method of casting or molding the semiconductor sealing material using a transfer molding device or an injection molding device and heating the same under a temperature condition of 50° C. to 200° C. for 2 hours to 10 hours is exemplified, and a semiconductor device which is a molded product can be obtained by the above-described method.

Moreover, as a method of producing a printed circuit board using the epoxy compound of the present invention, a method of impregnating a reinforcement basic material with a varnish-like curable composition containing the epoxy compound of the present invention, a curing agent, an organic solvent, and other additives and overlapping the reinforcement basic material with copper foil to be heated and pressed is exemplified. Examples of the reinforcement basic material being used here include paper, glass fabric, glass non-woven fabric, aramid paper, aramid cloth, glass mat, and glass roving cloth. Specifically, first, the method is a method of heating the above-described varnish-like curable composition at the heating temperature in response to the kind of the solvent to be used, preferably, in a temperature range of 50° C. to 170° C. to obtain a preprag which is a cured product. The mass ratios of the curable composition and the reinforcement basic material used at this time are not particularly limited, but it is preferable that the resin content in the preprag is normally adjusted to be in the range of 20% by mass to 60% by mass. Next, a target printed circuit board can be obtained by laminating the preprag obtained in the above-described manner using a known method, suitably overlapping the laminated preprag with the copper foil, and heating and pressing the resultant in a temperature range of 170° C. to 250° C. under a pressure of 1 MPa to 10 MPa for 10 minutes to 3 hours.

EXAMPLES

Hereinafter, the present invention will be described in detail with reference to Examples and Comparative Examples, and "part" and "%" described below are on a mass basis unless otherwise noted. Further, melt viscosity at 150° C., GPC, NMR, and an MS spectrum are measured under the following conditions.

Melt viscosity measurement method: The melt viscosity was measured using an ICI viscometer in conformity with ASTM D4287.

GPC: Measurement conditions are as follows.
Measuring device: "HLC-8220 GPC" manufactured by TOSOH CORPORATION Column: Guard column "HXL-L" manufactured by TOSOH CORPORATION
+"TSK-GEL G2000HXL" manufactured by TOSOH CORPORATION
+"TSK-GEL G2000HXL" manufactured by TOSOH CORPORATION
+"TSK-GEL G3000HXL" manufactured by TOSOH CORPORATION
+"TSK-GEL G4000HXL" manufactured by TOSOH CORPORATION
Detector: RI (Differential Refractometer)
Data treatment: "GPC-8020 model II version 4.10" manufactured by TOSOH CORPORATION
Measurement conditions: temperature of column: 40° C.
Developing solvent: tetrahydrofuran
Flow rate: 1.0 mL/min
Standard: monodisperse polystyrene whose molecular weight is known is used in conformity with measurement manual "GPC-8020 model II version 4.10" described above.
(Polystyrene to be Used)
"A-500" manufactured by TOSOH CORPORATION
"A-1000" manufactured by TOSOH CORPORATION
"A-2500" manufactured by TOSOH CORPORATION
"A-5000" manufactured by TOSOH CORPORATION
"F-1" manufactured by TOSOH CORPORATION
"F-2" manufactured by TOSOH CORPORATION
"F-4" manufactured by TOSOH CORPORATION
"F-10" manufactured by TOSOH CORPORATION
"F-20" manufactured by TOSOH CORPORATION
"F-40" manufactured by TOSOH CORPORATION
"F-80" manufactured by TOSOH CORPORATION
"F-128" manufactured by TOSOH CORPORATION
Sample: 1.0% by mass of a tetrahydrofuran solution being filtered (50 μL) using a microfilter in terms of the solid content of a resin
$^{13}$C-NMR: Measurement conditions are as follows.
Device: AL-400 manufactured by JEOL Ltd.
Measurement mode: SGNNE (1H complete decoupling method of removing NOE)
Solvent: dimethyl sulfoxide
Pulse angle: 45° pulse
Sample concentration: 30% by weight
Cumulative number: 10,000 times
MS: double focusing mass spectrometer "AX505H (FD505H)" manufactured by JEOL Ltd.

Example 1

Preparation of Epoxy Resin (1)

282 parts by mass (3 mol) of phenol and 3 parts by mass of paratoluene sulfonic acid were added to a flask on which a thermometer, a drop funnel, a cooling tube, a fractionating column, and a stirrer were mounted, and the temperature of the flask was increased to 80° C. from room temperature while the mixture was stirred. After the temperature reached 80° C., 162 parts by mass (1.5 mol) of parabenzoquinone was added thereto over 1 hour, the temperature was further increased to 130° C., and then the mixture was stirred for 1 hour to be reacted. After the reaction was finished, the mixture was dried under a reduced pressure, thereby obtaining 250 parts by mass of a phenol intermediate (1). FIG. 1 shows a GPC chart of the obtained phenol intermediate, FIG. 2 shows a 13CNMR spectrum, and FIG. 3 shows the MS spectrum. The hydroxyl group equivalent of the phenol intermediate (1) was 88 g/eq, and a peak of 202 corresponding to the compound represented by the following Structural Formula (a-1), a peak of 294 corresponding to the compound represented by the following Structural Formula (b-1), and a peak of 386 corresponding to the compound represented by the following Structural Formula (c-1) were detected from the MS spectrum.

Structural Formula (B-1) was 27.0%, and the content of a component corresponding to a tetranuclear compound (x3) represented by the following Structural Formula (C-1) was 9.7% in the epoxy resin calculated from the GPC chart.

[Chem. 56]

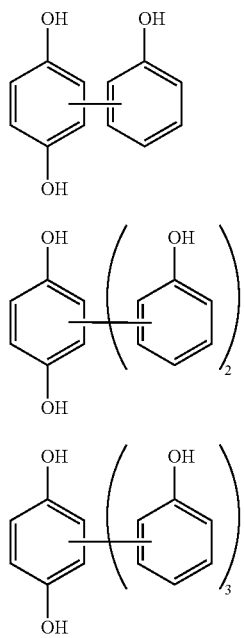

[Chem. 57]

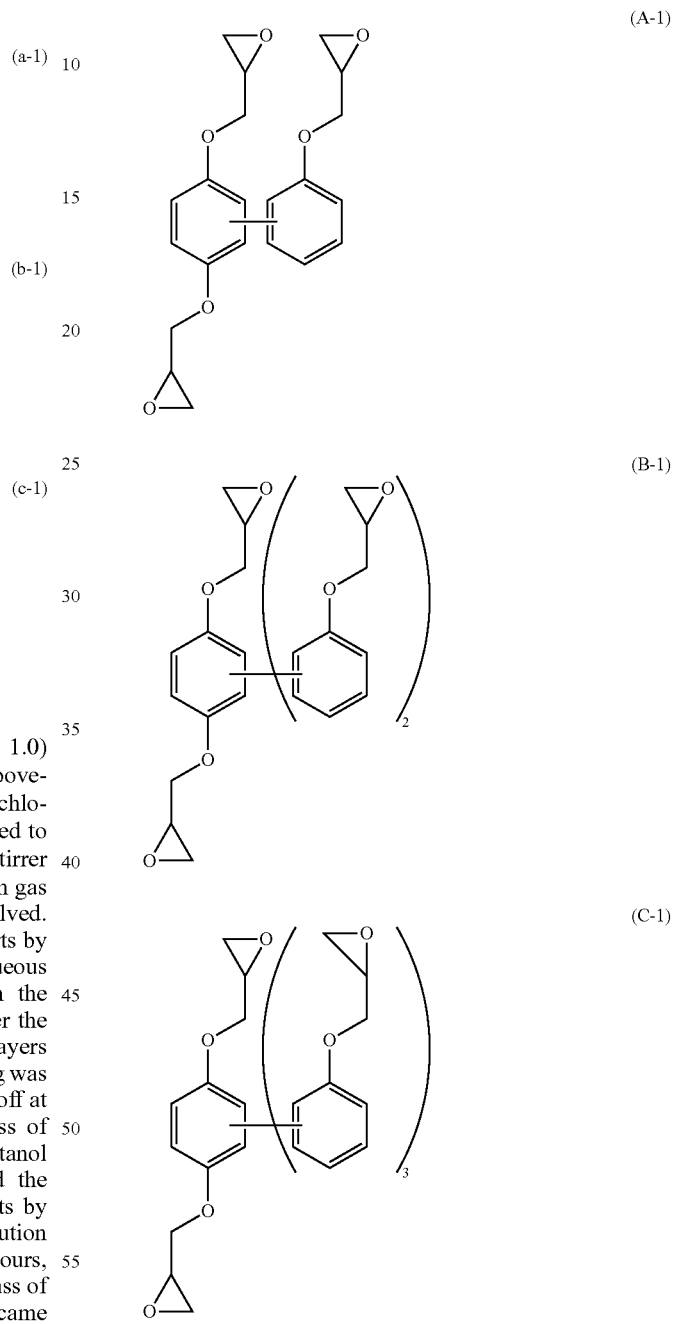

Next, 88 parts by mass (hydroxyl group equivalent: 1.0) of the phenol intermediate (1) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved. After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a lower layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 140 parts by mass of a target epoxy resin (1). FIG. 4 shows a GPC chart of the obtained epoxy resin (1). The epoxy equivalent of the epoxy resin (1) was 160 g/eq, the content of a component corresponding to a dinuclear compound (x1) represented by the following Structural Formula (A-1) was 29.7%, the content of a component corresponding to a trinuclear compound (x2) represented by the following Example 2

Preparation of Epoxy Resin (2)

649 parts by mass (6.0 mol) of ortho-cresol, 162 parts by mass (1.5 mol) of parabenzoquinone, and 8 parts by mass of paratoluene sulfonic acid were added to a flask on which a thermometer, a drop funnel, a cooling tube, a fractionating column, and a stirrer were mounted, and the temperature of the flask was increased to 120° C. from room temperature while the mixture was stirred. After the temperature reached 120° C., the mixture was stirred for 2 hours. After the reaction was finished, a deposited crystal product was filtered and washed with 200 parts by mass of water two times. Next, the mixture was dried by being heated under a reduced pressure, thereby obtaining 117 parts by mass of a phenol intermediate (2). FIG. 5 shows a GPC chart of the obtained phenol intermediate (2), FIG. 6 shows a 13CNMR spectrum, and FIG. 7 shows an MS spectrum. The hydroxyl group equivalent of the phenol intermediate (2) was 81 g/eq, and a peak of 216 corresponding to the compound represented by the following Structural Formula (a-2), a peak of 322 corresponding to the compound represented by the following Structural Formula (b-2), and a peak of 428 corresponding to the following Structural Formula (c-2) were detected from the MS spectrum.

[Chem. 58]

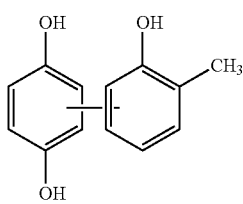
(a-2)

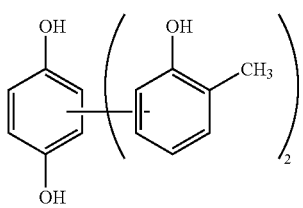
(b-2)

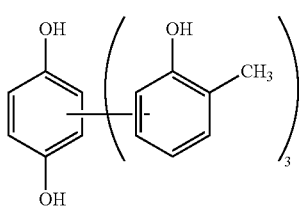
(c-2)

Next, 81 parts by mass (hydroxyl group equivalent: 1.0) of the phenol intermediate (2) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved. After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 130 parts by mass of a target epoxy resin (2). FIG. 8 shows a GPC chart of the obtained epoxy resin (2), FIG. 9 shows a 13CNMR spectrum, and FIG. 10 shows an MS spectrum. The epoxy equivalent of the epoxy resin (2) was 149 g/eq, and a peak of 384 corresponding to a dinuclear compound (x1) represented by the following Structural Formula (A-2), a peak of 546 corresponding to a trinuclear compound (x2) represented by the following Structural Formula (B-2), and a peak of 708 corresponding to a tetranuclear compound (x3) represented by the following Structural Formula (C-2) were detected from the MS spectrum. The content of a component corresponding to the dinuclear compound (x1) was 4.1%, the content of a component corresponding to the trinuclear compound (x2) was 70.7%, and the content of a component corresponding to the tetranuclear compound (x3) was 3.5% in the epoxy resin calculated from the GPC chart.

[Chem. 59]

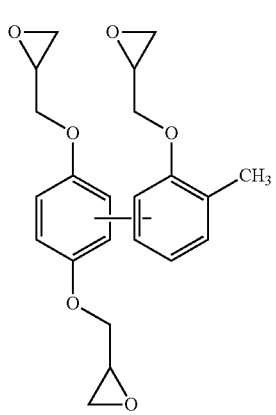
(A-2)

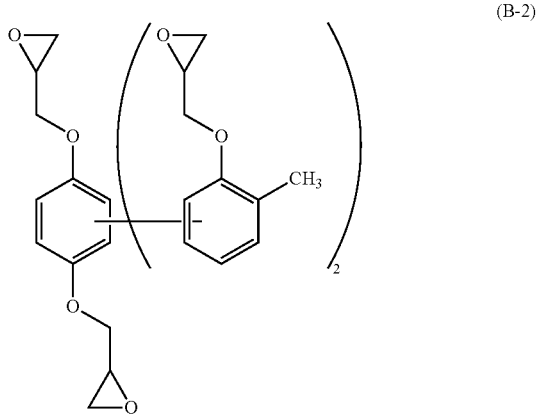
(B-2)

-continued

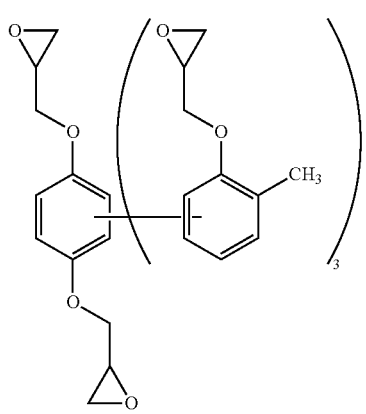

(C-2)

Example 3

Preparation of Epoxy Resin (3)

649 parts by mass (6.0 mol) of ortho-cresol and 3 parts by mass of paratoluene sulfonic acid were added to a flask on which a thermometer, a drop funnel, a cooling tube, a fractionating column, and a stirrer were mounted, and the temperature of the flask was increased to 80° C. from room temperature while the mixture was stirred. After the temperature reached 80° C., 162 parts by mass (1.5 mol) of parabenzoquinone was added thereto over 1 hour, the temperature was further increased to 130° C., and then the mixture was stirred for 1 hour to be reacted. After the reaction was finished, the mixture was dried under a reduced pressure, thereby obtaining 260 parts by mass of a phenol intermediate (3). FIG. 11 shows the GPC chart of the obtained phenol intermediate (3). The hydroxyl group equivalent of the phenol intermediate (3) was 97 g/eq.

Next, 97 parts by mass (hydroxyl group equivalent: 1.0) of the phenol intermediate (3) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved. After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 143 parts by mass of a target epoxy resin (3). FIG. 12 shows a GPC chart of the obtained epoxy resin (3). The epoxy equivalent of the epoxy resin (3) was 160 g/eq, the content of a component corresponding to a dinuclear compound (x1) was 19.4%, the content of a component corresponding to a trinuclear compound (x2) was 35.2%, and the content of a component corresponding to a tetranuclear compound (x3) was 8.0% in the epoxy resin calculated from the GPC chart.

Example 4

Preparation of Epoxy Resin (4)

733 parts by mass (6.0 mol) of 2,6-dimethyl phenol, 216 parts by mass (2.0 mol) of parabenzoquinone, and 9 parts by mass of paratoluene sulfonic acid were added to a flask on which a thermometer, a drop funnel, a cooling tube, a fractionating column, and a stirrer were mounted, and the temperature of the flask was increased to 120° C. from room temperature while the mixture was stirred. After the temperature reached 120° C., the mixture was stirred for 2 hours. After the reaction was finished, a deposited crystal product was filtered and washed with 200 parts by mass of water two times. Next, the mixture was dried by being heated under a reduced pressure, thereby obtaining 123 parts by mass of a phenol intermediate (4). FIG. 13 shows a GPC chart of the obtained phenol intermediate (4) and FIG. 14 shows an MS spectrum. The hydroxyl group equivalent of the phenol intermediate (4) was 88 g/eq, and a peak of 230 corresponding to the compound represented by the following Structural Formula (a-3), a peak of 350 corresponding to the compound represented by the following Structural Formula (b-3), and a peak of 470 corresponding to the compound represented by the following Structural Formula (c-3) were detected from the MS spectrum.

[Chem. 60]

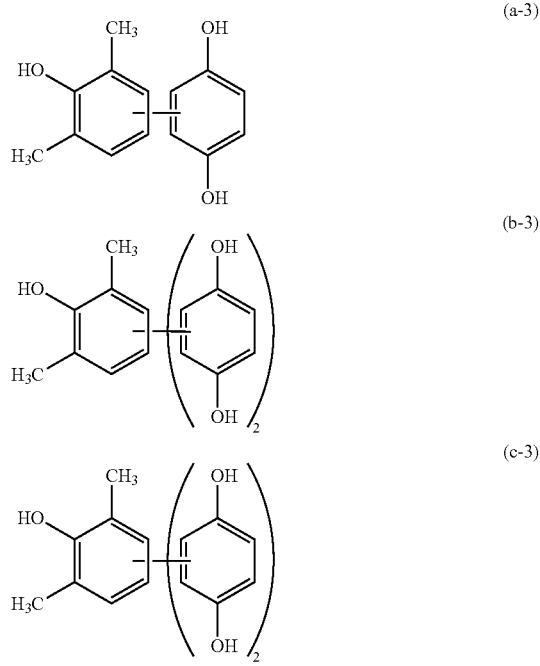

Next, 88 parts by mass (hydroxyl group equivalent: 1.0) of the phenol intermediate (4) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved.

After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 130 parts by mass of a target epoxy resin (4). FIG. 15 shows a GPC chart of the obtained epoxy resin (4). The epoxy equivalent of the epoxy resin (4) was 152 g/eq, the content of a component corresponding to a dinuclear compound (x1) represented by the following Structural Formula (A-3) was 7.0%, the content of a component corresponding to a trinuclear compound (x2) represented by the following Structural Formula (B-3) was 74.3%, and the content of a component corresponding to a tetranuclear compound (x3) represented by the following Structural Formula (C-3) was 1.0% in the epoxy resin calculated from the GPC chart.

[Chem. 61]

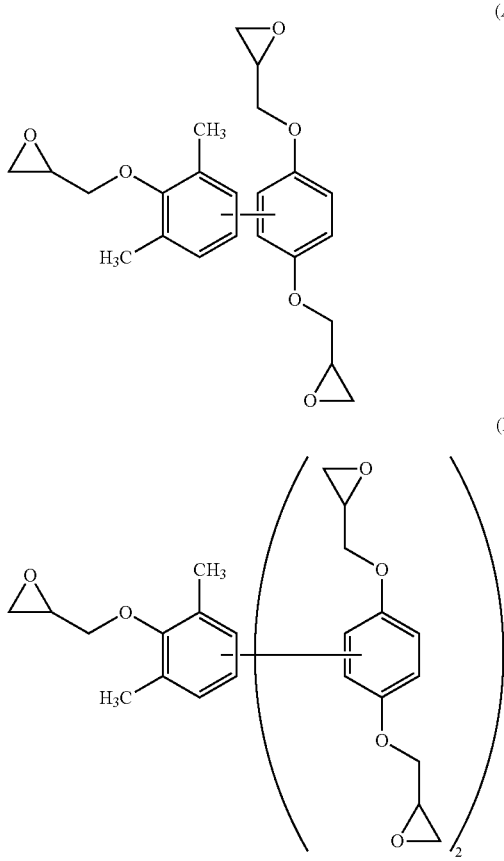

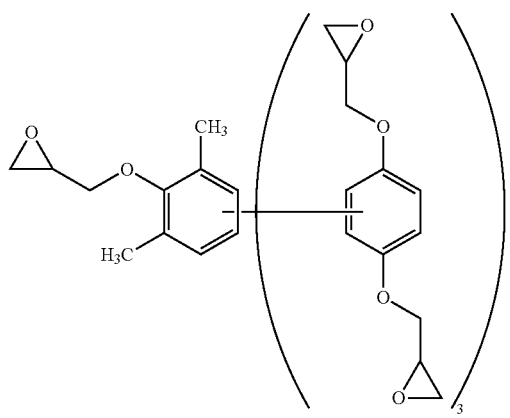

Example 5

Preparation of Epoxy Resin (5)

240 parts by mass (1.5 mol) of 2,7-dihydroxynaphthalene, 162 parts by mass (1.5 mol) of parabenzoquinone, 268 parts by mass of isopropyl alcohol, and 8 parts by mass of oxalic acid were added to a flask on which a thermometer, a drop funnel, a cooling tube, a fractionating column, and a stirrer were mounted, and the temperature of the flask was increased to 120° C. from room temperature while the mixture was stirred. After the temperature reached 120° C., the mixture was stirred and reacted for 2 hours. After the reaction was finished, the mixture was dried by being heated to 180° C. under a reduced pressure, thereby obtaining 359 parts by mass of a phenol intermediate (5). FIG. 16 shows the GPC chart of the obtained phenol intermediate, FIG. 17 shows a 13CNMR spectrum, and FIG. 18 shows an MS spectrum. The hydroxyl group equivalent of the phenol intermediate (5) was 68 g/eq, and a peak of 268 corresponding to the compound represented by the following Structural Formula (a-4) and a peak of 426 corresponding to the compound represented by the following Structural Formula (b-4) were detected from the MS spectrum.

[Chem. 62]

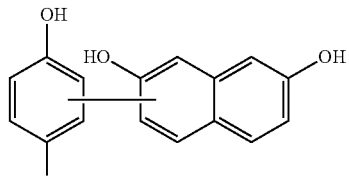

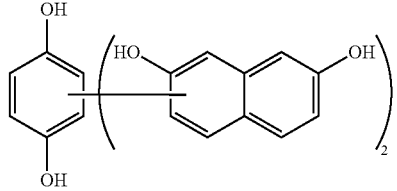

Next, 68 parts by mass (hydroxyl group equivalent: 1.0) of the phenol intermediate (5) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved. After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a lower layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 120 parts by mass of a target epoxy resin (5). FIG. 19 shows a GPC chart of the obtained epoxy resin (5), FIG. 20 shows a 13CNMR spectrum, and FIG. 21 shows an MS spectrum. The epoxy equivalent of the epoxy resin (5) was 155 g/eq, and a peak of 492 corresponding to a dinuclear compound (x1) represented by the following Structural Formula (A-4) and a peak of 762 corresponding to a trinuclear compound (x2) represented by the following Structural Formula (B-4) were detected from the MS spectrum. The content of a component corresponding to the dinuclear compound (x1) to be calculated from the GPC chart was 34.2% and the content of a component corresponding to the trinuclear compound (x2) was 21.7%.

[Chem. 63]

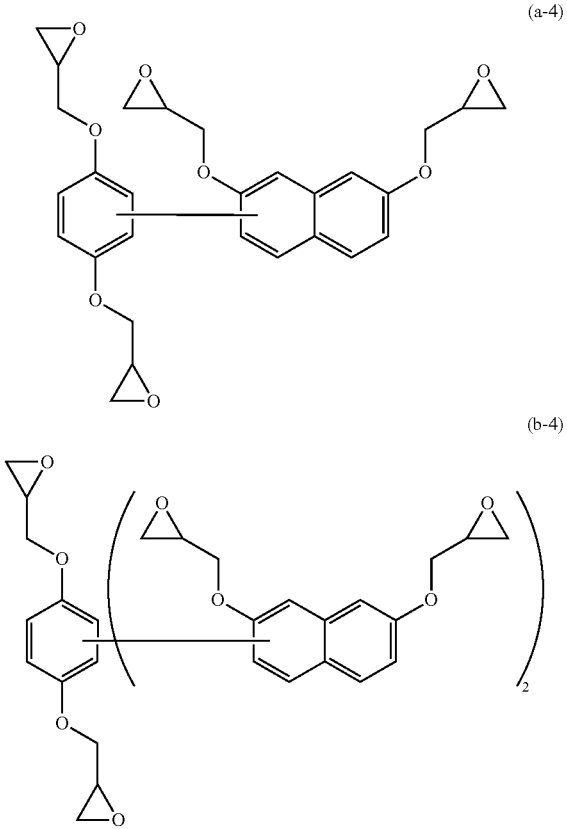

Example 6

Preparation of Epoxy Resin (6)

160 parts by mass (1.0 mol) of 2,7-dihydroxynaphthalene, 158 parts by mass (1.0 mol) of naphthoquinone, and 318 parts by mass of methyl isobutyl ketone were added to a flask on which a thermometer, a drop funnel, a cooling tube, a fractionating column, and a stirrer were mounted, and the temperature of the flask was increased to 150° C. from room temperature while the mixture was stirred. After the temperature reached 150° C., the mixture was stirred and reacted for 3 hours. After the reaction was finished, the mixture was dried by being heated to 180° C. under a reduced pressure, thereby obtaining 300 parts by mass of a phenol intermediate (6). FIG. 22 shows a GPC chart of the obtained phenol intermediate and FIG. 23 shows an MS spectrum. The hydroxyl group equivalent of the phenol intermediate (6) was 101 g/eq, and a peak of 318 corresponding to the compound represented by the following Structural Formula (a-5) and a peak of 300 corresponding to the compound represented by the following Structural Formula (d) were detected from the MS spectrum.

[Chem. 64]

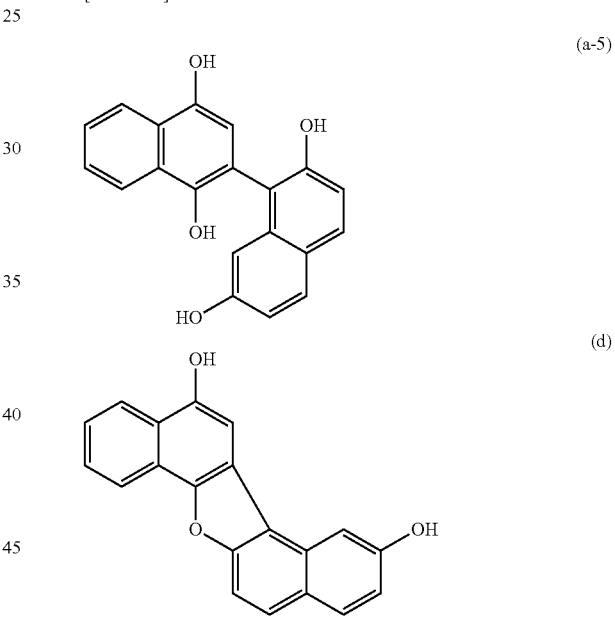

Next, 101 parts by mass (hydroxyl group equivalent: 1.0) of the phenol intermediate (6) obtained by the above-described reaction, 463 parts by mass (5.0 mol) of epichlorohydrin, and 53 parts by mass of n-butanol were added to a flask on which a thermometer, a cooling tube, and a stirrer were mounted while the flask was subjected to nitrogen gas purge. In addition, the mixture was stirred and dissolved. After the temperature was increased to 50° C., 220 parts by mass (1.10 mol) of a 20% sodium hydroxide aqueous solution was added thereto over 3 hours and then the solution was further reacted at 50° C. for 1 hour. After the reaction was finished, the stirring was stopped, water layers accumulated on a lower layer were removed, the stirring was restarted, and unreacted epichlorohydrin was distilled off at 150° C. under a reduced pressure. 300 parts by mass of methyl isobutyl ketone and 50 parts by mass of n-butanol were added to the obtained crude epoxy resin and the mixture was allowed to be dissolved. Further, 15 parts by mass of a 10 mass % sodium hydroxide aqueous solution was added to the solution to be reacted at 80° C. for 2 hours, and then the solution was washed with 100 parts by mass of water three times until the pH of a cleaning solution became neutral. Next, the inside of the system was dehydrated by azeotropy and was subjected to microfiltration, and then a solvent was distilled off under a reduced pressure, thereby obtaining 150 parts by mass of a target epoxy resin (6). FIG. 24 shows the GPC chart of the obtained epoxy resin (6) and FIG. 25 shows an MS spectrum. The epoxy equivalent of the epoxy resin (6) was 173 g/eq, and a peak of 542 corresponding to a dinuclear compound (x1) represented by the following Structural Formula (A-5) and a peak of 412 corresponding to the compound represented by the following Structural Formula (D) were detected, from the MS spectrum. The content of a component corresponding to the dinuclear compound (x1) to be calculated from the GPC chart was 27.0% and the content of a compound represented by the following Structural Formula (D) was 4.2%.

[Chem. 65]

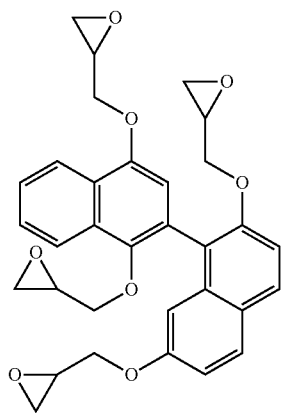

(A-5)

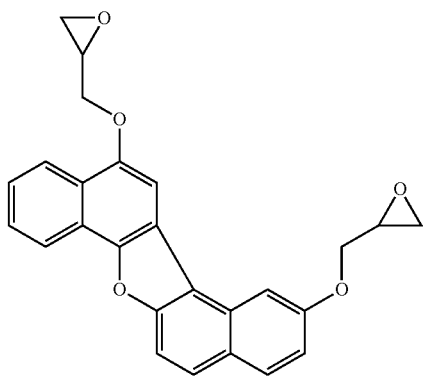

(D)

Examples 7 to 12 and Comparative Example 1

Various evaluation tests were performed on the epoxy resins (1) to (6) obtained before, in the manner described below. Two kinds of epoxy resins described below were used as samples for comparison.

Epoxy resin (1'): triphenylmethane type epoxy resin ("EPPN-502H" manufactured by Nippon Kayaku Co., Ltd., epoxy equivalent 172 g/eq)

<Measurement of Melt Viscosity>

With respect to each of the epoxy resins (1) to (6) and (1'), the melt viscosity at 150° C. was measured in conformity with ASTM D4287. The results are listed in Table 1.

TABLE 1

|  | Epoxy resin (1) | Epoxy resin (2) | Epoxy resin (3) | Epoxy resin (4) |
|---|---|---|---|---|
| Quinone compound (Q) | Parabenzoquinone | Parabenzoquinone | Parabenzoquinone | Parabenzoquinone |
| Phenol compound (P) | Phenol | Ortho-cresol | Ortho-cresol | Xylenol |
| Melt viscosity (dPa · s) | 0.8 | 0.9 | 1.1 | 1.0 |

|  | Epoxy resin (5) | Epoxy resin (6) | Epoxy resin (1') |
|---|---|---|---|
| Quinone compound (Q) | Parabenzoquinone | Naphthoquinone | — |
| Phenol compound (P) | Dihydroxynaphthalene | Dihydroxynaphthalene | — |
| Melt viscosity (dPa · s) | 1.4 | 1.6 | 2.4 |

<Evaluation of Heat Resistance>

1) Creation of Evaluation Sample

A curable composition was obtained by mixing any one of the epoxy resins (1) to (6) and (1'), a phenol novolac type phenol resin ("TD-2131" manufactured by DIC Corporation, hydroxyl group equivalent 104 g/eq) as a curing agent, and triphenylphosphine (hereinafter, abbreviated as "TPP") as a curing accelerator to have a composition listed in Table 2 below. The curable composition was poured into a mold having dimensions of 11 cm×9 cm×2.4 mm and molded by a press at a temperature of 150° C. for 10 minutes, and a molded product was taken out from the mold and postcured for 5 hours at a temperature of 175° C., thereby obtaining an evaluation sample.

2) Measurement of Glass Transition Temperature

The temperature at which a change in elastic modulus of the evaluation sample becomes maximum (tan δ change rate was the highest) was measured using a viscoelasticity measuring device (DMA: solid viscoelasticity measuring device RSAII manufactured by Rheometric Scientific, Inc., rectangular tension method: frequency 1 Hz, temperature rising rate 3° C./min) and was evaluated as the glass transition temperature. The results are listed in Table 2.

length of 127 mm, and a thickness of 1.6 mm was molded using a transfer molding device at a temperature of 175° C. for 90 seconds with the obtained curable composition and was cured after 5 hours at a temperature of 175° C., thereby obtaining a sample for evaluation.

2) Evaluation of Flame Retardancy

A combustion test was carried out in conformity with a UL-94 test method using five samples for evaluation having

TABLE 2

|  | Example 7 | Example 8 | Example 9 | Example 10 | Example 11 | Example 12 | Comparative Example 1 |
|---|---|---|---|---|---|---|---|
| Epoxy resin (1) | 60.6 | | | | | | |
| Epoxy resin (2) | | 58.9 | | | | | |
| Epoxy resin (3) | | | 60.6 | | | | |
| Epoxy resin (4) | | | | 59.4 | | | |
| Epoxy resin (5) | | | | | 59.8 | | |
| Epoxy resin (6) | | | | | | 62.5 | |
| Epoxy resin (1') | | | | | | | 62.3 |
| TD-2131 | 39.4 | 41.1 | 39.4 | 40.6 | 40.2 | 37.5 | 37.7 |
| TPP | 1.0 | 1.0 | 1.0 | 1.0 | 1.0 | 1.0 | 1.0 |
| Heat resistance (° C.) | 228 | 225 | 226 | 235 | 240 | 236 | 220 |

<Evaluation of Flame Retardancy>

1) Creation of Evaluation Sample

A curable composition was obtained by mixing any one of the epoxy resins (1) to (6) and (1'), a phenol novolac type phenol resin ("TD-2131" manufactured by DIC Corporation, hydroxyl group equivalent 104 g/eq) as a curing agent, triphenylphosphine (hereinafter, abbreviated as "TPP") as a curing accelerator, spherical silica ("FB-5604" manufactured by Denka Company Limited) as an inorganic filler, a coupling agent ("KBM-403" manufactured by Shin-Etsu Chemical Co., Ltd.) as a silane coupling agent, carnauba wax ("PEARL WAX No. 1-P" manufactured by CER-ARICA NODA Co., Ltd.), and carbon black to have a composition listed in Table 3 below and melting and kneading the mixture at a temperature of 85° C. for 5 minutes using two rollers. A sample having a width of 12.7 mm, a a thickness of 1.6 mm obtained before. The results are listed in Table 3.

Flame Retardant Test Class

*1: maximum combustion time (sec) in a single flame contact

*2: total combustion time (sec) of five test pieces

TABLE 3

|  | Example 7 | Example 8 | Example 9 | Example 10 | Example 11 | Example 12 | Comparative Example 1 |
|---|---|---|---|---|---|---|---|
| Epoxy resin (1) | 71.5 | | | | | | |
| Epoxy resin (2) | | 69.5 | | | | | |
| Epoxy resin (3) | | | 71.5 | | | | |
| Epoxy resin (4) | | | | 70.1 | | | |
| Epoxy resin (5) | | | | | 70.6 | | |
| Epoxy resin (6) | | | | | | 73.7 | |
| Epoxy resin (1') | | | | | | | 73.5 |
| TD-2131 | 46.5 | 48.5 | 46.5 | 47.9 | 47.4 | 44.3 | 44.5 |
| TPP | 2 | 2 | 2 | 2 | 2 | 2 | 2 |
| Spherical silica | 870 | 870 | 870 | 870 | 870 | 870 | 870 |
| Coupling agent | 4 | 4 | 4 | 4 | 4 | 4 | 4 |
| carnauba wax | 4 | 4 | 4 | 4 | 4 | 4 | 4 |
| Carbon black | 2 | 2 | 2 | 2 | 2 | 2 | 2 |
| Flame retardant test class | V-0 | V-0 | V-0 | V-0 | V-0 | V-0 | Combustion |
| *1 | 7 | 8 | 7 | 5 | 6 | 4 | 34 |
| *2 | 45 | 44 | 40 | 38 | 35 | 28 | 212 |

The invention claimed is:

1. An epoxy compound which has a molecular structure represented by the following Formula (I):

wherein G represents a glycidyl group, and X represents a structural site represented by the following Structural Formula (x1) or (x2);

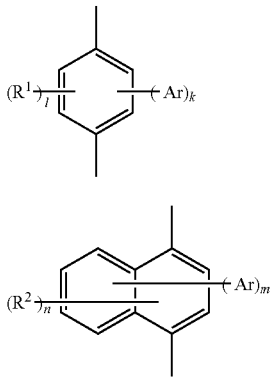

wherein, in Formula (x1) or (x2), $R^1$ and $R^2$ each independently represent any of an alkyl group having 1 to 4 carbon atoms or an alkoxy group having 1 to 4 carbon atoms, l represents an integer of 0 to 3, n represents an integer of 0 to 4, when l or n represents 2 or greater, a plurality of $R^1$'s or $R^2$'s may be the same as or different from each other, k represents an integer of 1 to 3, m represents 1 or 2, Ar represents a structural site represented by the following Structural Formula (Ar1) or (Ar2), and when k or m represents 2 or greater, a plurality of Ar's may be the same as or different from each other;

[Chem. 3]

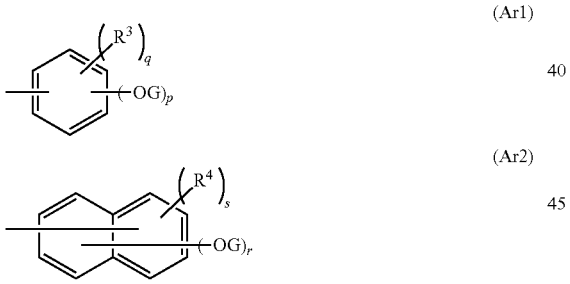

wherein, in Formula (Ar1) or (Ar2), G represents a glycidyl group, p and r each independently represent 1 or 2, $R^3$ and $R^4$ each independently represent any of an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s represents 2 or greater, a plurality of $R^3$'s or $R^4$'s may be the same as or different from each other.

2. An epoxy resin comprising the epoxy compound according to claim 1.

3. A curable composition comprising, as essential components:
the epoxy compound according to claim 1; and
a curing agent.

4. A cured product which is obtained by a curing reaction of the curable composition according to claim 3.

5. A semiconductor sealing material comprising:
the curable composition according to claim 3; and
an inorganic filler.

6. A printed circuit board which is obtained by impregnating a reinforcement basic material with a resin composition varnished by blending a curable composition with an organic solvent, and superposing a copper foil on the resulting material, followed by heat-pressing;
wherein the curable composition comprises, as essential components:
an epoxy compound and a curing agent;
wherein the epoxy compound has a molecular structure represented by the following Formula (I):

wherein G represents a glycidyl group, and X represents a structural site represented by the following Structural Formula (x1) or (x2);

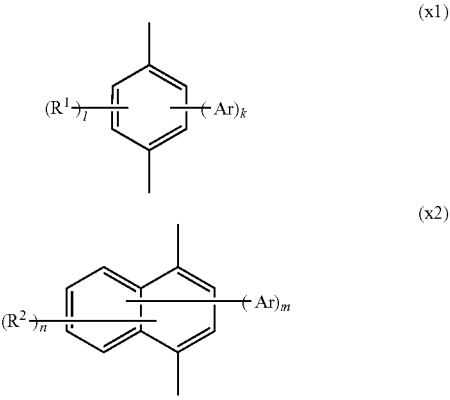

wherein, in Formula (x1) or (x2), $R^1$ and $R^2$ each independently represent any of an alkyl group having 1 to 4 carbon atoms or an alkoxy group having 1 to 4 carbon atoms, l represents an integer of 0 to 3, n represents an integer of 0 to 4, when l or n represents 2 or greater, a plurality of $R^1$'s or $R^2$'s may be the same as or different from each other, k represents an integer of 1 to 3, m represents 1 or 2, Ar represents a structural site represented by the following Structural Formula (Ar1) or (Ar2), and when k or m represents 2 or greater, a plurality of Ar's may be the same as or different from each other;

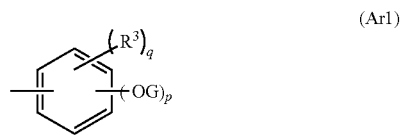

-continued

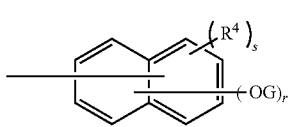
(Ar2)

wherein, in Formula (Ar1) or (Ar2), G represents a glycidyl group, p and r each independently represent 1 or 2, $R^3$ and $R^4$ each independently represent any of an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s represents 2 or greater, a plurality of $R^3$'s or $R^4$'s may be the same as or different from each other.

7. An epoxy resin comprising a mixture of dinuclear, trinuclear and tetranuclear epoxy compounds, wherein the dinuclear, trinuclear and tetranuclear epoxy compounds independently each independently have a molecular structure represented by the following Formula (I):

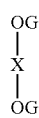
(I)

wherein G represents a glycidyl group, and X represents a structural site represented by the following Structural Formula (x1) or (x2);

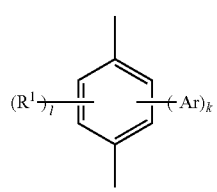
(x1)

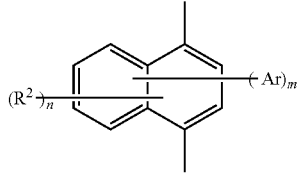
(x2)

wherein, in Formula (x1) or (x2), $R^1$ and $R^2$ each independently represent any of an alkyl group having 1 to 4 carbon atoms, an alkoxy group having 1 to 4 carbon atoms, an aryl group, or an aralkyl group, l represents an integer of 0 to 3, n represents an integer of 0 to 4, when l or n represents 2 or greater, a plurality of $R^1$'s or $R^2$'s may be the same as or different from each other, k represents an integer of 1 to 3, m represents 1 or 2, Ar represents a structural site represented by the following Structural Formula (Ar1) or (Ar2), and when k or m represents 2 or greater, a plurality of Ar's may be the same as or different from each other;

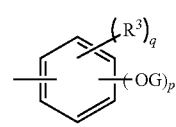
(Ar1)

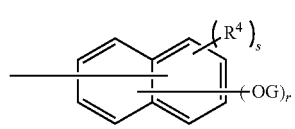
(Ar2)

wherein, in Formula (Ar1) or (Ar2), G represents a glycidyl group, p and r each independently represent 1 or 2, $R^3$ and $R^4$ each independently represent any of an alkyl group having 1 to 4 carbon atoms, an alkoxy group having 1 to 4 carbon atoms, an aryl group, or an aralkyl group, $R^4$ in Formula (Ar2) may be bonded to any one of two aromatic nuclei, q represents an integer of 0 to 4, s represents an integer of 0 to 6, and when q or s represents 2 or greater, a plurality of $R^3$'s or $R^4$'s may be the same as or different from each other;

and wherein:

the content ratio of the dinuclear compound in the epoxy resin is in the range of 2% to 50% in terms of the area ratio in GPC measurement, the content ratio of the trinuclear compound in the epoxy resin is in the range of 10% to 95% in terms of the area ratio in GPC measurement, and the content ratio of the tetranuclear compound in the epoxy resin is in the range of 0.5% to 20% in terms of the area ratio in the GPC measurement.

\* \* \* \* \*